United States Patent
Antle et al.

(10) Patent No.: US 9,751,957 B2
(45) Date of Patent: Sep. 5, 2017

(54) MANUFACTURING PROCESS FOR CYCLODEXTRIN DERIVATIVES

(71) Applicant: Cydex Pharmaceuticals, Inc., La Jolla, CA (US)

(72) Inventors: Vincent D. Antle, Olathe, KS (US); Jose R. Matos, Plano, TX (US)

(73) Assignee: CyDex Pharmaceuticals, Inc., San Diego, CA (US)

( * ) Notice: Subject to any disclaimer, the term of this patent is extended or adjusted under 35 U.S.C. 154(b) by 134 days.

(21) Appl. No.: 14/378,953

(22) PCT Filed: Feb. 14, 2013

(86) PCT No.: PCT/US2013/026218
§ 371 (c)(1),
(2) Date: Aug. 14, 2014

(87) PCT Pub. No.: WO2013/123254
PCT Pub. Date: Aug. 22, 2013

(65) Prior Publication Data
US 2016/0009826 A1 Jan. 14, 2016

Related U.S. Application Data

(60) Provisional application No. 61/599,156, filed on Feb. 15, 2012.

(51) Int. Cl.
*C08B 37/16* (2006.01)
(52) U.S. Cl.
CPC . *C08B 37/0012* (2013.01); *B01J 2219/00164* (2013.01); *B01J 2219/00166* (2013.01)
(58) Field of Classification Search
None
See application file for complete search history.

(56) References Cited

U.S. PATENT DOCUMENTS

| | | |
|---|---|---|
| 2,744,938 A | 7/1952 | Urban |
| 3,426,011 A | 2/1969 | Parmerter et al. |
| 3,453,257 A | 7/1969 | Parmerter et al. |
| 3,453,259 A | 7/1969 | Parmerter et al. |
| 3,459,731 A | 8/1969 | Gramera et al. |
| 4,317,881 A | 3/1982 | Yagi et al. |
| 4,477,568 A | 10/1984 | Hokse et al. |
| 4,597,946 A | 7/1986 | Ward |
| 4,658,058 A | 4/1987 | Umezawa et al. |
| 4,738,923 A | 4/1988 | Ammeraal |
| 4,904,306 A | 2/1990 | Ammeraal |
| 4,920,214 A | 4/1990 | Friedman |
| 5,019,562 A | 5/1991 | Folkman |
| 5,134,127 A | 7/1992 | Stella et al. |
| 5,173,481 A | 12/1992 | Pitha et al. |
| 5,183,809 A | 2/1993 | Weisz et al. |
| 5,241,059 A | 8/1993 | Yoshinaga |
| 5,324,718 A | 6/1994 | Loftsson |
| 5,376,537 A | 12/1994 | Cami et al. |
| 5,376,645 A | 12/1994 | Stella et al. |
| 5,393,880 A | 2/1995 | Shieh et al. |
| 5,472,954 A | 12/1995 | Loftsson |
| 5,479,254 A | 12/1995 | Woskov et al. |
| 5,512,665 A | 4/1996 | Uchiyama et al. |
| 5,536,826 A | 7/1996 | Hirsenkorn |
| 5,550,222 A | 8/1996 | Shieh |
| 5,569,756 A | 10/1996 | Qi et al. |
| 5,578,719 A | 11/1996 | Gadelle et al. |
| 5,594,125 A | 1/1997 | Seyschab |
| 5,620,872 A | 4/1997 | Shieh et al. |
| 5,658,390 A | 8/1997 | Shieh et al. |
| 5,658,894 A | 8/1997 | Weisz et al. |
| 5,710,268 A | 1/1998 | Wimmer |
| 5,756,484 A | 5/1998 | Fuertes et al. |
| 5,760,015 A | 6/1998 | Joullie et al. |
| 5,831,081 A | 11/1998 | Reuscher |
| 5,846,954 A | 12/1998 | Joullie et al. |
| 5,874,418 A | 2/1999 | Stella et al. |
| 5,914,122 A | 6/1999 | Otterbeck et al. |
| 5,935,941 A | 8/1999 | Pitha |
| 6,033,573 A | 3/2000 | Toles et al. |
| 6,046,177 A | 4/2000 | Stella et al. |
| 6,133,248 A | 10/2000 | Stella |
| 6,153,746 A | 11/2000 | Shah et al. |
| 6,235,505 B1 | 5/2001 | Grull et al. |
| 6,337,302 B1 | 1/2002 | Teng et al. |
| 6,407,079 B1 | 6/2002 | Muller et al. |

(Continued)

FOREIGN PATENT DOCUMENTS

| | | |
|---|---|---|
| CN | 102040675 | 5/2011 |
| EP | 0 579 435 | 1/1994 |
| EP | 1067143 | * 8/2000 |
| EP | 1 067 143 | 1/2001 |
| EP | 1 950 227 | 7/2008 |
| EP | 2 018 866 | 1/2009 |
| JP | 04-57801 | 2/1992 |
| JP | 05-001102 | 1/1993 |
| JP | 05-504783 | 7/1993 |
| JP | 07-149801 | 6/1995 |

(Continued)

OTHER PUBLICATIONS

Loftsson et al., "Cyclodextrins in Drug Delivery" Expert Opinion in Drug Delivery (2005) vol. 2 pp. 335-351.*

(Continued)

*Primary Examiner* — Eric Olson
(74) *Attorney, Agent, or Firm* — Knobbe, Martens, Olson & Bear LLP

(57) ABSTRACT

A process and equipment assembly for reacting a substituent precursor with a cyclodextrin starting material to provide a raw product comprising a cyclodextrin derivative and 1% or less of an initial amount of the substituent precursor is provided. The process of the present invention provides cyclodextrin derivatives in substantially shorter time and with fewer side products than previous processes that utilize substantially the same starting materials.

28 Claims, 13 Drawing Sheets

(56) References Cited

U.S. PATENT DOCUMENTS

| | | |
|---|---|---|
| 6,479,467 B1 | 11/2002 | Buchanan et al. |
| 6,524,595 B1 | 2/2003 | Coleman et al. |
| 6,610,671 B2 | 8/2003 | Buchanan et al. |
| 6,869,939 B2 | 3/2005 | Mosher et al. |
| 7,034,013 B2 | 4/2006 | Thompson et al. |
| 7,582,758 B2 | 9/2009 | Martin |
| 7,625,878 B2 | 12/2009 | Stella et al. |
| 7,629,331 B2 | 12/2009 | Pipkin et al. |
| 7,635,773 B2 | 12/2009 | Antle |
| 8,114,438 B2 | 2/2012 | Pipkin et al. |
| 8,236,782 B2 | 8/2012 | Mosher et al. |
| 8,410,077 B2 | 4/2013 | Antle |
| 8,492,538 B1 | 7/2013 | Matos |
| 2003/0055023 A1 | 3/2003 | Rajewski et al. |
| 2005/0164986 A1 | 7/2005 | Mosher et al. |
| 2005/0186267 A1 | 8/2005 | Thompson et al. |
| 2005/0250738 A1 | 11/2005 | Mosher et al. |
| 2006/0258537 A1 | 11/2006 | Stella et al. |
| 2007/0020196 A1 | 1/2007 | Pipkin et al. |
| 2007/0020298 A1 | 1/2007 | Pipkin et al. |
| 2007/0020299 A1 | 1/2007 | Pipkin et al. |
| 2007/0175472 A1 | 8/2007 | Pipkin et al. |
| 2007/0202054 A1 | 8/2007 | Pipkin et al. |
| 2008/0194519 A1 | 8/2008 | Cloyd |
| 2009/0011037 A1 | 1/2009 | Pipkin et al. |
| 2009/0012042 A1 | 1/2009 | Ren et al. |
| 2009/0123540 A1 | 5/2009 | Pipkin et al. |
| 2009/0239942 A1 | 9/2009 | Cloyd |
| 2009/0270348 A1 | 10/2009 | Antle |
| 2009/0270358 A1 | 10/2009 | Lee et al. |
| 2010/0093663 A1 | 4/2010 | Antle |
| 2010/0292268 A1 | 11/2010 | Mosher et al. |
| 2011/0021013 A1 | 1/2011 | Takahashi |
| 2012/0021013 A1 | 1/2012 | Esaki |
| 2012/0136072 A1 | 5/2012 | Mosher et al. |
| 2013/0184357 A1 | 7/2013 | Antle |
| 2013/0331356 A1 | 12/2013 | Olhava et al. |
| 2015/0045311 A1 | 2/2015 | Antle et al. |
| 2015/0284479 A1 | 10/2015 | Antle et al. |
| 2016/0158384 A1 | 6/2016 | Antle |

FOREIGN PATENT DOCUMENTS

| | | |
|---|---|---|
| JP | 07-216002 | 8/1995 |
| JP | 10-504351 | 4/1998 |
| JP | 2001-31703 | 2/2001 |
| WO | WO 90/12035 | 10/1990 |
| WO | WO 91/11172 | 8/1991 |
| WO | WO 99/42111 | 8/1999 |
| WO | WO 01/40316 | 6/2001 |
| WO | WO 02/055562 | 7/2002 |
| WO | WO 2005/042584 | 5/2005 |
| WO | WO 2005/118277 | 5/2005 |
| WO | WO 2006/071491 | 7/2006 |
| WO | WO 2008/005053 | 1/2008 |
| WO | WO 2008/005691 | 1/2008 |
| WO | WO 2008/005692 | 1/2008 |
| WO | WO 2008/005802 | 1/2008 |
| WO | WO 2008/005819 | 1/2008 |
| WO | WO 2008/034040 | 3/2008 |
| WO | WO 2008/135601 | 11/2008 |
| WO | WO 2009/018069 | 2/2009 |
| WO | WO 2009/045497 | 4/2009 |
| WO | WO 2009/134347 | 11/2009 |
| WO | WO 2010/053487 | 5/2010 |
| WO | WO 2013/130666 | 9/2013 |
| WO | WO 2014/066274 | 5/2014 |

OTHER PUBLICATIONS

Hartman et al., "Deciding Whether to Go with the Flow: Evaluating the Merits of Flow Reactors for Synthesis" Angew Chem Int Ed (2011) vol. 50 pp. 7502-7519.*

English machine translation of EP1067143 (dated 2000) above, dwnloaded from worldwide.espacenet.com.*

ISR and WO dated Apr. 19, 2013 in PCT/US13/026218.

Adam et al., 2002, Cyclodextrin-derived host molecules as reversal agents for the neuromuscular blocker rocuronium bromide: synthesis and structure-activity relationships, J. Med. Chem. 45:1806-1816.

Baptista et al., 1996, Near-infrared detection of flow injection analysis by acoustooptic tunable filter-based spectrophotometry, Anal. Chem., 68(6):971-976.

Betadex, Jan.-Feb. 2008, Pharmacopeial Forum, The United States Pharmacopeial Convention, 34(1):127-130.

Comprehensive Supramolecular Chemistry, vol. 3 Cyclodextrins, Szejtli et al., eds., Elsevier Science Inc., Tarrytown, NY, 1996.

Connors et al., eds., Chemical Stability of Pharmaceuticals, 1st Ed., John Wiley & Sons, New York, 1979, pp. 134-135.

Connors et al., eds., Chemical Stability of Pharmaceuticals, 2nd Ed., John Wiley & Sons, New York, 1986, pp. 564-565, 584-565, 770-771, 776-779.

Crowley et al., Drug-Excipient Interactions, Pharmaceutical Technology, Mar. 2001, pp. 1-6, Advanstar Publication.

Cyclodextrins in Pharmacy, Fromming et al., eds., Kluwer Academic Publishiing, Dordrecht, Netherlands, 1994.

Norit Americas Inc., Jul. 2007, DARCO® KB-G Powdered Activated Carbon Product Datasheet, 2 pp.

Fridriksdottir et al., 1997, Formulation and testing of methazolamide cyclodextrin eye drop solutions, Journal of Controlled Release, 44(1):95-99.

Fridriksdottir et al., Jan. 1996, Design and in vivo testing of 17β-estradiol HPβCD sublingual tablets, Die Pharmazie, 51(1):39-42.

Fridriksdottir et al., Mar. 31-Apr. 2, 1996, Solubilization of β-cyclodextrin: the effect of polymers and various drugs on the solubility of β-cyclodextrin, Proceedings of the Eighth International Symposium on Cyclodextrins, eds. Szejtli et al., Budapest, 373-376.

Hughes et al., 2004, Array reactors for parallel synthesis, Journal of Combinatorial Chemistry, 6(3):308.

Jacquet et al., 2004, Liquid chromatography analysis of monosubstituted sulfobutyl ether-β-cyclodextrin isomers on porous graphitic carbon, J. Sep. Sci. 27(14):1221-1228.

Kristinsson et al., 1996, Dexamethasone-cyclodextrin-polymer cσ-complexes in aqueous eye drops, Investigative Ophthalmology & Visual Science, 37(6):1199-1203.

Lammers et al., 1971, Properties of cyclodextrins: Part VI. Water-soluble cyclodextrin-derivatives. Preparation and Analysis, Die Starke, 23(5):167-171.

Lammers et al., 1972, Properties of cyclodextrins, Part VIII Determination of the composition of inclusion complexes of hexane and 2,3-dimethylbutane with cyclodextrin derivatives in aqueous solution, Recl. Trav. Chim. Pays-Bas, 91(6):733-753.

Loftsson et al., 1994, The effect of polyvinylpyrrolidone and hydroxypropyl methylcellulose on HPβCD complexation of hydrocortisone and its permeability through hairless mouse skin, European Journal of Pharmaceutical Sciences, 2:297-301.

Loftsson et al., 1994, The effect of water-soluble polymers on drug-cyclodextrin complexation, International Journal of Pharmaceutics (Netherlands), 110(2):169-177.

Loftsson et al., 1996, Effects of cyclodextrins and polymers on topical drug delivery to the eye—evaluations in humans, Proceedings of the 23rd International Symposium on Controlled Release of Bioactive Materials, pp. 453-454.

Loftsson et al., 1996, The influence of water-soluble polymers and pH on hydroxypropyl-β-cyclodextrin complexation of drugs, Drug Development and Industrial Pharmacy, 22(5):401-405.

Loftsson et al., 1997, Cyclodextrins as pharmaceutical excipients, Pharm. Technol. Eur. 9(5):26-34.

Loftsson et al., 1997, Enhanced complexation efficiency of cyclodextrins, Pharmaceutical Research, 14(11):S203.

Loftsson et al., 1998, Cyclodextrin solubilization of ETH-615, a zwitterionic drug, Drug Development and Industrial Pharmacy, 24(4):365-370.

(56) References Cited

OTHER PUBLICATIONS

Loftsson et al., 1998, The effect of water-soluble polymers on the aqueous solubility and complexing abilities of β-cyclodextrin, International Journal of Pharmaceutics, 163(1-2):115-121.
Loftsson et al., 1999, Methods to enhance the complexation efficiency of cyclodextrins, S.T.P. Pharma Sciences, 9(3):237-242.
Loftsson et al., 2001, Cyclodextrin solubilization of benzodiazepines: formulation of midazolam nasal spray, International Journal of Pharmaceutics, 212(1):29-40.
Loftsson et al., Apr. 11, 1994, The effect of hydroxypropyl methylcellulose on the release of dexamethasone from aqueous 2-hyroxypropyl-β-cyclodextrin formulations, International Journal of Pharmaceutics (Netherlands), 104:181-184.
Loftsson et al., Oct. 1994, Polymer-cyclodextrin-drug complexes, Pharmaceutical Research, 11(10):5225.
Loftsson et al., Oct. 1996, Pharmaceutical applications of cyclodextrins. 1. Drug solubilization and stabilization, Journal of Pharmaceutical Sciences, 85(10):1017-1025.
Loftsson et al., Sep. 16, 1996, Drug-cyclodextrin-polymer ternary complexes, European Journal of Pharmaceutical Sciences, 4(SUPPL):5144.
Loftsson et al., Sep. 1996, Solubilization of β-cyclodextrin, Eur. J. Pharm. Sci, 4(Suppl.):5143.
Loftsson et al., Sep. 2001, Sustained drug delivery system based on a cationic polymer and an anionic drug/cyclodextrin complex, Pharmazie, 56(9):746-747.
Loftsson, 1996, Topically effective acetazolamide eye-drop solution in man, Pharmaceutical Sciences, 2(6):277-279.
Loftsson, 1998, Drug-cyclodextrin complexation in the presence of water soluble polymers: enhanced solubility and percutaneous transport, Abstracts of Papers Part 1, 216th ACS National Meeting, Boston, Aug. 23-27, CELL-016.
Loftsson, Apr. 2-6, 1995, The effect of polymers on cyclodextrin complexation, Book of Abstracts 209th ACS National Meeting, 209(1):33-CELL.
Loftsson, Nov. 1988, Increasing the cyclodextrin complexation of drugs and drug biovailability through addition of water-soluble polymers, Pharmazie, 53(11):733-740.
Luna et al., 1997, Fractionation and characterization of 4-sulfobutyl ether derivatives of cyclomaltoheptaose (62 -cyclodextrin), Carbohydrate Research, 299:103-110.
Malaekeh-Nikouei et al., May 16, 2009, Evaluation the effect of cyclodextrin complexation on aqueous solubility of fluorometholone to achieve ophthalmic solution, J Incl Phemon Macrocycl Chem, 6 pp.
Masson et al., 1999, Drug-cyclodextrin complexation in the presence of water-soluble polymers: enhanced solubility and percutaneous transport, ACS Symposium Series, 737 (Polysaccharide Applications), pp. 24-45.
Modified Cyclodextrins: Scaffolds and Templates for Supramolecular Chemistry, Easton et al. eds., Imperial College Press, London, UK, 1999.
Neunert et al., 2009, Glycosidic moiety changes the spectroscopic properties of DL-α-tocopherol in DMSO/water solution and in organic solvents, Molecular and biomolecular spectroscopy, Spectrochimica Acta Part A, 73:301-308.
New Trends in Cyclodextrins and Derivatives, Duchene ed., Editions de Sante, Parks, France, 1991.
Polymer Science, in Physical Pharmacy. Physical Chemical Principles in Pharmaceutical Sciences, 3rd edition, Martin et al., 1983, pp. 592-638.
Polymers and Macromolecules, in Physicochemical Principles of Pharmacy, 2nd edition, Florence et al., eds. pp. 281-334, 1988.
Qu et al., 2002, Sulfoalkyl ether β-cyclodextrin derivatives: synthesis and characterizations, J. Inclusion Phenom. Macro. Chem, 43:213-221.

Remington's Pharmaceutical Sciences, 18th Edition, Gennaro ed., 1990, Hydrophilic Dispersons, pp. 291-294.
Remington's Pharmaceutical Sciences, 18th Edition, Gennaro ed., 1990, Hydrophilic Dispersons, pp. 436-437.
Sandarusi et al., 1988, An automated flow calrimeter for heat capacity and enthalpy measurements, International Journal of Thermophysics, 9(6):993-1002.
Savolainen et al., 1998, Co-administration of a water-soluble polymer increases the usefulness of cyclodextrins in solid oral dosage forms, Pharmaceutical Research, 15(11):1696-1701.
Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.
Sigurdardottir et al., Dec. 29, 1995, The effect of polyvinylpyrrolidone on cyclodextrin complexation of hydrocortisone and its diffusion through hairless mouse skin, International Journal of Pharmaceutics (Netherlands), 126:73-78.
Sotthivirat et al., 2007, Evaluation of various properties of alternative salt forms of sulfobutylether-β-cyclodextrine, $(SBE)_{7M}$-β-CD, Int. J. Pharm. 330:73-81.
Stella, Mar. 31-Apr. 2, 1996, SBE7-β-CD, a new, novel and safe polyanionic β-cyclodextrin derivative: characterization and biomedical applications, Proceedings of the Eighth International Symposium on Cyclodextrins, Budapest, Hungary, pp. 471-476.
Szente et al., 1999, Highly soluble cyclodextrin derivatives: chemistry, properties, and trends in development, Advanced Drug Delivery Reviews 36:17-28.
Tarver et al., 2002, 2-O-substituted cyclodextrins as reversal agents for the neuromuscular blocker rocuronium bromide, Bioorganic & Medicinal Chemistry, 10:1819-1827.
The Handbook of Pharmaceutical Excipients, 5th Ed., Rowe et al., eds., The Pharmaceutical Press and American Pharmacists Association, London, UK and Washington, DC (2006).
Third European Congress of Pharmaceutical Sciences, Edinburgh, Scotland, UK, Sep. 15-17, 1996.
Tongiani et al., 2005, Sulfoalkyl ether-alkyl ether-cyclodextrin derivatives, their synthesis, NMR characterization, and binding of 6α-methylprednisolone, J. Pharm. Sci., 94(11):2380-2392.
Vegvari et al., 2000, A new easy-to-prepare continuous electrochromatographic bed for enantiomer recogniation, Electrophoresis, 21:3116-3125.
Wenz et al., 1999, Synthesis of highly water-soluble cyclodextrin sulfonates by addition of hydrogen sulfite to cyclodextrin allyl ethers, Carbohydr. Res. 322:153-165.
Wittung et al., 1994, Absorption flattening in the optical spectra of liposome-entrapped substances, FEBS Letters 352:37-40.
Yang et al., 2011, Pharmacokinetics, pharmacodynamics, metabolism, distribution, and excretion of of carfilzomib in rats, Drug Metabolism and Distribution, 39(10):1873-1882.
Extended European Search Report dated Sep. 17, 2015 in patent application No. 13748804.5.
Blanchard et al., 1999, Some important considerations in the use of cyclodextrins, Pharmaceutical Research, 16(12):1796-1798.
Luna et al., 1996 Evaluation of the utility of capillary electrophoresis for the analysis of sulfobutyl ether β-cyclodextrin mixtures, J. Pharmaceutical and Biomedical Analysis 15:63-71.
Luna et al., 1996, Characterization of sulfobutyl ether β-cyclodextrin mixtures, Proceedings of the Eighth International Symposium on Cyclodextrins 133-136.
Mosher et al., 2001, Complexation and Cyclodextrins, in Encyclopedia of Pharmaceutical Technology, Swarbrick et al., eds., Marcel Dekker, Inc., New York, pp. 49-71.

* cited by examiner

FIG. 1A
FIG. 1B
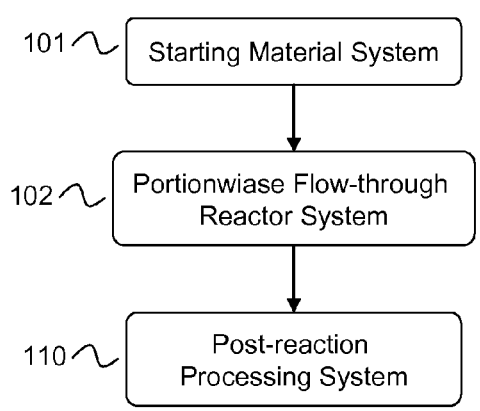
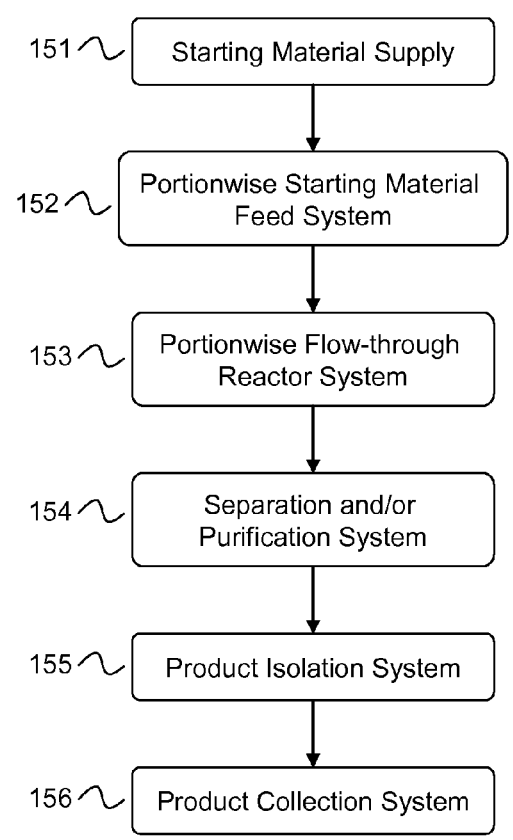

= Mixer

= Liquid/Liquid Extractor

= Heat Exchanger

= Diafilter / Ultrafilter

= Flow-Through Reactor

= Combination Mixer, Heat Exchanger and Flow-through reactor

▮ = Solid-Bed Purification Medium (⌐∿⌐) = Combination Heat Exchanger and Flow-Through Reactor

MANUFACTURING PROCESS FOR CYCLODEXTRIN DERIVATIVES

RELATED APPLICATIONS

This application is the U.S. National Phase under 35 U.S.C. §371 of International Application No. PCT/US2013/026218, filed on Feb. 14, 2013, designating the U.S. and published in English as WO 2013/123254, which claims the benefit of U.S. Provisional Application No. 61/599,156, filed Feb. 15, 2012, both of which are incorporated by reference herein in their entirety, including any drawings.

BACKGROUND OF THE PRESENT INVENTION

Field of the Present Invention

The present invention relates to a process for rapidly preparing a derivatized cyclodextrin with limited amounts of side products. In some embodiments, the process is conducted continuously or semi-continuously using flow-through equipment.

Background Art

Hydrophobic, hydrophilic, polymerized, ionized, non-ionized and many other derivatives of cyclodextrins have been developed, and their use in various industries has been established. Generally, cyclodextrin derivatization proceeds via reactions in which —OH groups at the 2-, 3-, and/or 6-position of the amylose rings of a cyclodextrin are replaced with substituent groups. Substituents include neutral, anionic and/or cationic functional groups.

Known cyclodextrin derivatives include, but are not limited to, sulfoalkyl ether cyclodextrin derivatives, alkylether cyclodextrin derivatives (e.g., methyl, ethyl and propyl ether cyclodextrins), hydroxyalkyl cyclodextrin derivatives, thioalkyl ether cyclodextrin derivatives, carboxylated cyclodextrin derivatives (e.g., succinyl-β-cyclodextrin, and the like), sulfated cyclodextrin derivatives, and the like. Cyclodextrin derivatives having more than one type of functional group are also known, such as sulfoalkyl ether-alkyl ether-cyclodextrin derivatives (see, e.g., WO 2005/042584 and US 2009/0012042, each of which is hereby incorporated by reference in its entirety). In particular, cyclodextrin derivatives having 2-hydroxypropyl groups and/or sulfoalkyl ether groups have found use in pharmaceutical formulations.

A sulfobutyl ether derivative of β-cyclodextrin ("SBE-β-CD") has been commercialized by CyDex Pharmaceuticals, Inc. as CAPTISOL® and ADVASEP®. The anionic sulfobutyl ether substituent improves the aqueous solubility and safety of the parent β-cyclodextrin, which can reversibly form complexes with active pharmaceutical agents, thereby increasing the solubility of active pharmaceutical agents and, in some cases, increase the stability of active pharmaceutical agents in aqueous solution. CAPTISOL® has a chemical structure according to Formula X:

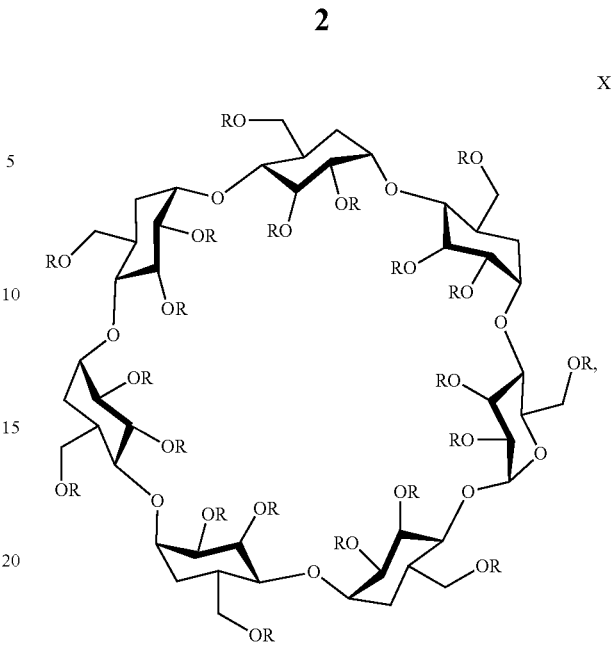

where R is $(-H)_{21-n}$ or $((-CH_2)_4-SO_3^-Na^+)$, and n is 6 to 7.1.

Sulfoalkyl ether derivatized cyclodextrins (such as CAPTISOL®) are typically prepared using batch methods as described in, e.g., U.S. Pat. Nos. 5,134,127, 5,376,645 and 6,153,746, each of which is hereby incorporated by reference in its entirety.

Sulfoalkyl ether cyclodextrins and other derivatized cyclodextrins can also be prepared according to the methods described in the following patents and published patent applications: U.S. Pat. No. 3,426,011, U.S. Pat. No. 3,453,257, U.S. Pat. No. 3,453,259, U.S. Pat. No. 3,459,731, U.S. Pat. No. 4,638,058, U.S. Pat. No. 472,706, U.S. Pat. No. 5,019,562, U.S. Pat. No. 5,173,481, U.S. Pat. No. 5,183,809, U.S. Pat. No. 5,241,059, U.S. Pat. No. 5,536,826, U.S. Pat. No. 5,594,125, U.S. Pat. No. 5,658,894, U.S. Pat. No. 5,710,268, U.S. Pat. No. 5,756,484, U.S. Pat. No. 5,760,015, U.S. Pat. No. 5,846,954, U.S. Pat. No. 6,407,079, U.S. Pat. No. 7,625,878, U.S. Pat. No. 7,629,331, U.S. Pat. No. 7,635,773, US2009/0012042, JP 05001102 and WO 01/40316, as well as in the following non-patent publications: Lammers et al., Red. Trav. Chim. Pays-Bas 91:733 (1972): Staerke 23:167 (1971), Adam et al., J. Med. Chem. 45:1806 (2002), Qu et al., J. Inclusion Phenom. Macrocyclic Chem. 43:213 (2002), Tarver et al., Bioorg. Med. Chem. 10:1819 (2002), Fromming et al., Cyclodextrins in Pharmacy (Kluwer Academic Publishing, Dordrecht, 1994), Modified Cvclodextrins: Scaffolds and Templates for Supramolecular Chemistry (C. J. Easton et al. eds., Imperial College Press, London, UK, 1999), New Trends in Cyclodextrins and Derivatives (Dominique Duchene ed., Editions de Santé, Paris, FR, 1991), Comprehensive Supramolecular Chemistry 3 (Elsevier Science Inc., Tarrytown, N.Y.), the entire disclosures of which are hereby incorporated by reference.

Generally, processes to prepare cyclodextrin derivatives are batch processes, in which a reaction vessel is charged with reagents for a specific amount of time and temperature, and the reaction and purification are performed in a step-wise manner. Process conditions significantly impact the structure and associated properties of a cyclodextrin derivative prepared therefrom. For example, the process conditions can alter the average degree of substitution, the distribution of substitution, the regiochemistry of substitution (i.e., the substitution pattern), and combinations thereof. Process conditions that can be controlled and varied include reaction time, temperature, stoichiometry, pH, rate of agitation, concentration, and the like. In addition to being costly and time-consuming, cyclodextrin derivatives prepared by batch processes also require significant purification due to, e.g., the breakdown of reagents and the formation of side products.

For example, sulfoalkyl ether cyclodextrins as disclosed in, e.g., U.S. Pat. No. 5,134,127 are made by treating an unsubstituted α-, β-, or γ-cyclodextrin with an alkyl sultone in the presence of a base. Because the underivatized cyclodextrin is a nephrotoxin, and alkyl sultones are also toxic, it is desirable that residual alkyl sultone and underivatized cyclodextrin levels be as low as possible in the product. U.S. Pat. No. 6,153,746 provides a batch method for producing sulfoalkyl ether cyclodextrins that contain low amounts of both residual cyclodextrin and alkyl sultone materials. However, the process disclosed therein relies upon both a slow, step-wise addition of alkyl sultone and a lengthy degradation step in which residual alkyl sultone is slowly degraded under basic conditions.

BRIEF SUMMARY OF THE PRESENT INVENTION

What is needed is a process for preparing cyclodextrin derivatives in which the formation of side products is minimized. What is also needed is a process capable of rapidly preparing a cyclodextrin derivative that does not require extensive heating and/or mixing. What is also needed is a more efficient process for preparing cyclodextrin derivatives in which a substituent precursor can be combined with a cyclodextrin starting material in a single step and rapidly reacted to provide a raw product that requires minimal purification. What is also needed is a process that can be operated in a continuous or semi-continuous manner.

The present invention provides a process for preparing a derivatized cyclodextrin, the process comprising: reacting a cyclodextrin starting material, a substituent precursor, and an optional catalyst to provide a raw product comprising a derivatized cyclodextrin, wherein the raw product comprises 1% or less of an initial amount of the substituent precursor.

In some embodiments, a process is run continuously (referred to herein as an "in-line" process) to prepare cyclodextrin derivatives in a period of time that is significantly shorter than comparable batch-type processes that employ substantially similar starting materials. The cyclodextrin derivatives prepared by the processes of the present invention can be water soluble or water insoluble. The cyclodextrin derivatives can be prepared by the processes of the present invention to have a predetermined degree of substitution, such as a low degree of substitution, a moderate degree of substitution, a high degree of substitution, a predetermined regiochemical distribution of substituents, a low span, a moderate span, and/or a high span of substitution.

The process of the present invention excludes a batch-type step of combining, in which the cyclodextrin starting material and the one or more substituent precursors are combined in a batch-type reactor to form a batch of raw product comprising a derivatized cyclodextrin.

In some embodiments, the reacting is performed in a continuous or semi-continuous manner comprising:

providing a feedstock comprising a liquid or gas medium, the cyclodextrin starting material, the substituent precursor, and the optional catalyst; and
continuously or semi-continuously flowing the feedstock into a reactor and flowing out of the reactor the raw product comprising a derivatized cyclodextrin.

In some embodiments, the process does not include after the reacting, adding a reagent to the raw product in order to degrade the substituent precursor.

In some embodiments, the feedstock comprises a medium selected from: water, an alcohol, an ether, a ketone, a sulfoxide, a nitrile, an amide, an ester, an oil, a chlorinated solvent, a water-soluble polymer, and combinations thereof.

In some embodiments, the cyclodextrin starting material comprises an unsubstituted cyclodextrin selected from: an α-cyclodextrin, a β-cyclodextrin, a γ-cyclodextrin, and combinations thereof.

In some embodiments, the substituent precursor and the cyclodextrin starting material are present in a molar ratio of 1:1 to 50:1.

In some embodiments, the substituent precursor is selected from: a sulfoalkylating agent, an alkylating agent, and combinations thereof. In some embodiments, the substituent precursor comprises a mixture of two or more substituent precursors.

In some embodiments, the optional catalyst is present in molar excess relative to the substituent precursor. In some embodiments, the optional catalyst is selected from: an alkalinizing agent, an acidifying agent, a phase transfer agent, an enzyme, a transition metal compound, and combinations thereof. In some embodiments, the optional catalyst comprises an alkalinizing agent, and the substituent precursor is selected from: a sulfoalkylating agent, an alkylating agent, a hydroxyalkylating agent, and combinations thereof.

In some embodiments, the feedstock has a pH of 9 to 14.

In some embodiments, the providing comprises a process selected from:
(i) mixing the cyclodextrin starting material with the optional catalyst to form a mixture, and mixing portions of the mixture with portions of the substituent precursor to form the feedstock;
(ii) mixing the cyclodextrin starting material with the substituent precursor to form a mixture, and mixing portions of the mixture with portions of the optional catalyst to form the feedstock;
(iii) mixing the optional catalyst with the substituent precursor to form a mixture, and mixing the mixture with portions of the cyclodextrin starting material to form the feedstock; and
(iv) mixing portions of the cyclodextrin starting material, the substituent precursor, and the optional catalyst substantially simultaneously to form the feedstock.

In some embodiments, the mixing comprises flowing any of the mixtures through a flow-through mixer.

In some embodiments, a process further comprises preheating at least one of the cyclodextrin starting material and/or the substituent precursor prior to the reacting.

In some embodiments, the feedstock has a residence time in the reactor of 0.5 sec to 4 hours. In some embodiments, the feedstock has a residence time in the reactor of 0.5 sec to 30 minutes, and the reactor temperature is 70° C. to 200° C. In some embodiments, the feedstock has a pH of 9 to 14, the feedstock has a residence time in the reactor of 0.5 sec to 20 minutes, and the temperature of the reactor is 90° C. to 160° C.

In some embodiments, a process of the present invention further comprises quenching any unreacted substituent precursor present in the raw product. In some embodiments, a process of the present invention further comprises neutralizing the raw product.

In some embodiments, a process of the present invention further comprises separating the derivatized cyclodextrin from the raw product, wherein the separating includes at least one of filtering, centrifuging, decanting, and combinations thereof.

In some embodiments, a process of the present invention further comprises isolating the derivatized cyclodextrin, wherein the isolating includes at least one of drying, sterile filtering, concentrating, and combinations thereof.

In some embodiments, a process of the present invention further comprises purifying the derivatized cyclodextrin, wherein the purifying includes at least one of extracting, diafiltrating, dialyzing, treating with a carbon medium, treating with an adsorption medium, treating with a color-removal medium, and combinations thereof.

In some embodiments, the derivatized cyclodextrin is present in a raw product in a yield of 70% or higher based upon the amount of the cyclodextrin starting material.

In some embodiments, a molar ratio of the substituent precursor to the cyclodextrin starting material of 3:1 to 18:1 provides a derivatized cyclodextrin having an average degree of substitution of 2 to 12.

In some embodiments, a molar ratio of the substituent precursor to the cyclodextrin starting material of 1:1 to 5:1 provides a derivatized cyclodextrin having an average degree of substitution of 4 or less.

In some embodiments, a molar ratio of the substituent precursor to the cyclodextrin starting material of 5:1 to 14:1 provides a derivatized cyclodextrin having an average degree of substitution of 3 to 7.

In some embodiments, the derivatized cyclodextrin has a solubility in water of 100 mg/mL or higher. In some embodiments, the derivatized cyclodextrin has a solubility in water of less than 100 mg/mL.

In some embodiments, the derivatized cyclodextrin includes a cationic substituent, an anionic substituent, or a combination thereof.

In some embodiments, the derivatized cyclodextrin includes a substituent selected from: a sulfoalkyl ether group, an ether group, an alkyl ether group, an alkenyl ether group, a hydroxyalkyl ether group, a hydroxyalkenyl ether group, a thioalkyl ether group, an aminoalkyl ether group, a mercapto group, an amino group, an alkylamino group, a carboxyl group, an ester group, a nitro group, a halo group, an aldehyde group, a 2,3-epoxypropyl group, and combinations thereof.

The present invention is also directed to a process for preparing a derivatized cyclodextrin, the process comprising:
combining in a liquid or gas medium a cyclodextrin starting material, a sulfoalkylating agent present in a molar excess relative to the cyclodextrin starting material, and an alkalinizing agent present in a molar excess relative to the one or more sulfoalkylating agents to form a feedstock; and reacting the feedstock by continuously or semi-continuously flowing the feedstock into and out of a reactor for a residence time of 0.5 sec to 4 hours, at a temperature of 30° C. to 200° C., and at a pressure of 1 bar or higher to form a raw product comprising the derivatized cyclodextrin.

The present invention is also directed to products prepared by the above processes.

In some embodiments, the product comprises a cyclodextrin derivative having a degree of substitution of 6 to 7.1. In some embodiments, a product comprises a cyclodextrin having an average degree of substitution of 6.5.

Further embodiments, features, and advantages of the present inventions, as well as the composition, structure and operation of the various embodiments of the present invention, are described in detail below with reference to the accompanying drawings.

BRIEF DESCRIPTION OF THE FIGURES

The accompanying drawings, which are incorporated herein and form a part of the specification, illustrate one or more embodiments of the present invention and, together with the description, further serve to explain the principles of the present invention and to enable a person skilled in the pertinent art to make and use the invention. The following drawings are given by way of illustration only, and thus are not intended to limit the scope of the present invention.

FIGS. 1A-1B provide a flow diagrams for a process of the present invention.

FIG. 11A as a diafiltration system, and FIG. 11B as an ultrafiltration system.

Figure 2:
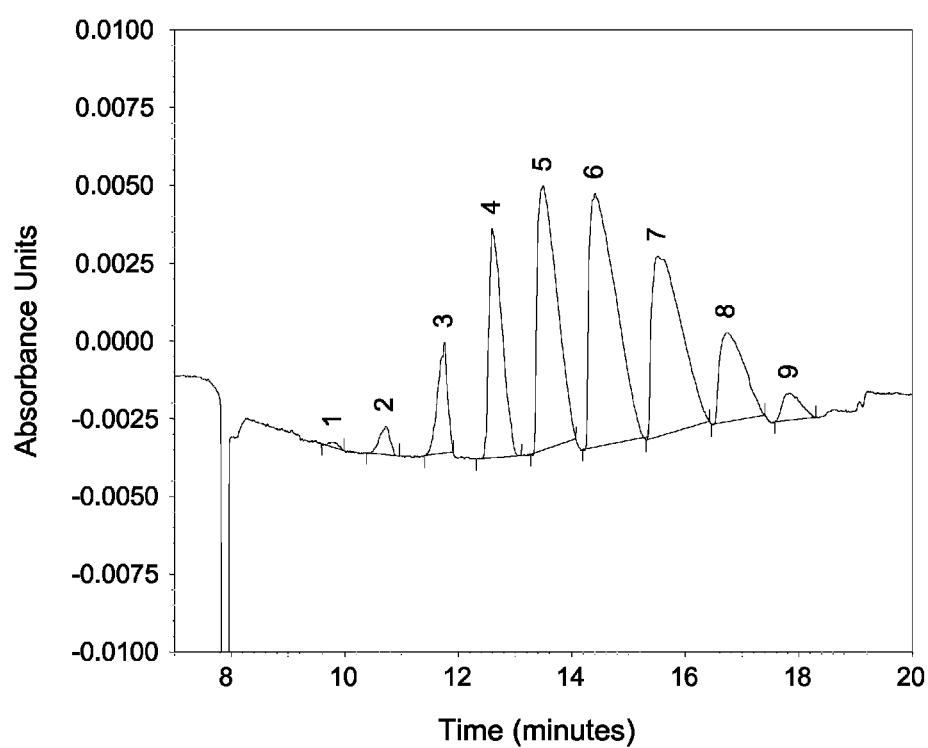
FIG. 2 provides an electropherogram of a cyclodextrin derivative of the present invention having an average degree of substitution of seven.

One or more embodiments of the present invention will now be described with reference to the accompanying drawings. In the drawings, like reference numbers can indicate identical or functionally similar elements. Additionally, the left-most digit(s) of a reference number can identify the drawing in which the reference number first appears.

DETAILED DESCRIPTION OF THE PRESENT INVENTION

This specification discloses one or more embodiments that incorporate the features of this invention. The disclosed embodiment(s) merely exemplify the invention. The scope of the present invention is not limited to the disclosed embodiment(s). The invention is defined by the claims appended hereto.

The invention includes combinations and sub-combinations of the various aspects and embodiments disclosed herein. Further, when a particular feature, structure, or characteristic is described in connection with an embodiment, it is understood that it is within the knowledge of one skilled in the art to effect such feature, structure, or characteristic in connection with other embodiments whether or not explicitly described. These and other aspects of this invention will be apparent upon reference to the following detailed description, examples, claims and attached figures.

As used herein, percentages refer to "% by weight" and/or "w/w" (weight by weight concentration) unless otherwise indicated.

All references to spatial descriptions (e.g., "above," "below," "up," "down," "top," "bottom," etc.) made herein are for purposes of description and illustration only, and should be interpreted as non-limiting upon the compositions, formulations, and methods of making and using the same, which can be spatially arranged in any orientation or manner.

Processes

The present invention provides a process for preparing a derivatized cyclodextrin, the process comprising: reacting a cyclodextrin starting material, a substituent precursor, and an optional catalyst to provide a raw product comprising a derivatized cyclodextrin, wherein the raw product comprises 1% or less of the substituent precursor.

In some embodiments, a process is run continuously (referred to herein as an "in-line" process) to prepare cyclodextrin derivatives in a period of time that is significantly shorter than comparable batch-type processes that employ substantially similar starting materials. The cyclodextrin derivatives prepared by the processes of the present invention can be water soluble or water insoluble. The cyclodextrin derivatives can be prepared by the processes of the present invention to have a predetermined degree of substitution, such as a low degree of substitution, a moderate degree of substitution, a high degree of substitution, a predetermined regiochemical distribution of substituents, a low span, a moderate span, and/or a high span of substitution.

As used herein, a "cyclodextrin starting material" refers to an underivatized parent cyclodextrin or derivatized cyclodextrin that is derivatized according to a process of the present invention. An underivatized parent cyclodextrin can be any type of cyclodextrin (e.g., α-CD, β-CD, γ-CD, and combinations thereof). In some embodiments, a cyclodextrin starting material comprises a single cyclodextrin material. Cyclodextrin starting materials can be obtained from various commercial sources, and/or prepared according to U.S. Pat. Nos. 4,904,306, 4,477,568, 4,317,881, 6,235,505, 5,550,222, 5,658,390, 5,620,872 and 5,376,537, which are hereby incorporated by reference in the entirety.

In some embodiments, a cyclodextrin starting material is protonated (i.e., the hydroxyl groups remain protonated), a partial salt (i.e., at least a portion of the hydroxyl groups are deprotonated), or a salt (i.e., in which all of the hydroxyl groups are deprotonated). A partial salt or a salt of a cyclodextrin can be prepared by treating a cyclodextrin comprising one or more —OH groups with an alkalinizing agent (e.g., a metal oxide, a metal hydroxide, a metal hydride, and the like) to form a metal salt of the cyclodextrin. The degree of salt formation depends largely on the stoichiometric amount of the alkalinizing agent that is used. Metal salts include, but are not limited to, an alkali metal cation (e.g., $K^+$, $Na^+$, $Li^+$, and the like), an alkaline earth metal cation (e.g., $Mg^{+2}$, $Ca^{+2}$, $Sr^{+2}$, and the like), a transition metal cation (e.g., $Cr^{+2}$, $Cr^{+3}$, $Mo^{+2}$, $Mo^{+3}$, $Mo^{+4}$, $Mn^{+2}$, $Mn^{+3}$, $Co^{+2}$, $Co^{+3}$, $Ni^+$, $Ni^{+2}$, $Cu^+$, $Cu^{+2}$, $Zn^{+2}$, $Cd^+$, $Cd^{+2}$, $Ag^+$, and the like), and combinations thereof.

In some embodiments, a partial salt of a cyclodextrin is prepared by mixing an alkalinizing agent comprising a metal with an underivatized cyclodextrin in a ratio provided in the following:

TABLE 1

| Partial Metal Salt of CD (equivalents of metal cations per mole of CD) | Alkalinizing agent (molar ratio of alkalinizing agent:CD required to prepare a metal salt where the alkalinizing agent has one alkaline equivalent per mole) | Alkalinizing agent (molar ratio of alkalinizing agent:CD required to prepare a metal salt where the alkalinizing agent has two alkaline equivalents per mole) |
|---|---|---|
| 1 to 4 | 1:1 to 4:1, respectively | 0.5:1 to 2:1, respectively |
| 4 to 7 | 4:1 to 7:1, respectively | 2:1 to 3.5:1, respectively |
| 7 to 10 | 7:1 to 10:1, respectively | 3.5:1 to 5:1, respectively |
| 10 to 12 | 10:1 to 12:1, respectively | 5:1 to 6:1, respectively |
| 12 to 15 | 12:1 to 15:1, respectively | 6:1 to 7.5:1, respectively |
| Greater than 15 | Greater than 15:1 | Greater than 7.5:1 |
| 1 to 15 | 1:1 to 15:1, respectively | 0.5:1 to 7.5:1, respectively |

In some embodiments, the molar ratio of a monovalent alkalinizing agent to a cyclodextrin is 1:1 to 100:1, 1:1 to 75:1, 1:1 to 50:1, 1:1 to 30:1, 1:1 to 28:1, 1:1 to 25:1, 1:1 to 22:1, 1:1 to 19:1, 1:1 to 16:1, 1:1 to 14:1, 1:1 to 11:1, 1:1 to 8:1, 1:1 to 5:1, 1:1 to 4:1, 4:1 to 7:1, 7:1 to 10:1, 10:1 to 12:1, 12:1 to 15:1, or greater than 15:1.

In some embodiments, the molar ratio of a divalent alkalinizing agent to a cyclodextrin starting material is 0.5:1 to 50:1, 0.5:1 to 38:1, 0.5:1 to 25:1, 0.5:1 to 15:1, 0.5:1 to 14:1, 0.5:1 to 13:1, 0.5:1 to 11:1, 0.5:1 to 10:1, 0.5:1 to 8:1, 0.5:1 to 7:1, 0.5:1 to 6:1, 0.5:1 to 4:1, 0.5:1 to 2.5:1, 0.5:1 to 2:1, 2:1 to 3.5:1, 3.5:1 to 5:1, 5:1 to 6:1, 7:1 to 7.5:1, or greater than 7.5:1.

The cyclodextrin starting material can include an underivatized cyclodextrin (e.g., α-, β-, γ-cyclodextrin, and combinations thereof), or a previously prepared cyclodextrin derivative. The processes of the present invention include alterations in the known sequence of chemical synthetic steps for preparing water soluble cyclodextrin derivatives having a monomodal average degree of substitution or a monomodal substitution profile.

A "substituent precursor" refers to an agent capable of reacting with a hydroxyl group of a cyclodextrin starting material. A substituent precursor will react with the oxygen atom of a hydroxyl moiety of a parent cyclodextrin thereby converting the hydroxyl moiety to a target moiety (substituent) on the cyclodextrin. A substituent precursor can also be referred to herein as an alkylating agent. Exemplary alkylating agents that can be used to derivatize (etherify) the cyclodextrin include, by way of example and without limitation, various alkyl sulfate esters. Specific AE (alkyl ether) precursors include sulfate esters such as diethyl sulfate, dimethyl sulfate, and dipropyl sulfate, or methylating agents such as trimethyloxonium tetrafluoroborate (TMOTFB), trimethyloxonium p-toluenesulfonate, trimethyloxonium hexafluorophosphate, trimethyloxonium hexafluoroantimonate, trimethyloxonium alkane/aryl sulfonate, dimethoxycarbenium tetrafluoroborate, and O-methyldibenzofuranium tetrafluoroborate, or trialkylsulfonium halide agents such as trimethylsulfonium iodide. Exemplary sulfoalkylating agents that can be used to derivatize (etherify) the cyclodextrin include, by way of example and without limitation, alkyl sultone. Specific SAE (sulfoalkyl ether) precursors include 1,4-butane sultone, 1,5-pentane sultone, 1,3-propane sultone, and other sulfoalkylating agents. Exemplary HAE (hydroxyalkyl ether) precursors that can be used to derivatize the cyclodextrin include 2,3-epoxy alcohols or halohydrins and others described in references cited herein. Exemplary HANE (hydroxyalkenyl ether) precursor that can be used to derivatize the cyclodextrin include 3,4-epoxy-1-butene, 4,5-epoxy-1-pentene, 5,6-epoxy-1-hexene and other epoxy alkenyl agents. An exemplary EPPE (epoxyalkyl ether, epoxyalkylating agent) precursor includes epichlorohydrin.

The term "alkanol" as used herein includes linear, cyclic, branched, saturated, and unsaturated alkyl components of the alkanol groups, in which the hydroxyl groups can be situated at any available position on the alkyl moieties. The term "cycloalkanol" includes unsubstituted or substituted (e.g., by methyl or ethyl) cyclic alcohols.

In some embodiments, the cyclodextrin starting material comprises an unsubstituted cyclodextrin selected from: an α-cyclodextrin, a β-cyclodextrin, a γ-cyclodextrin, and combinations thereof.

As used herein, a "substituent precursor" refers to a compound, reagent, moiety, or substance capable of reacting with an —OH group present on a cyclodextrin.

In some embodiments, a substituent precursor is selected from: a sulfoalkylating agent, an alkylating agent, and combinations thereof. In some embodiments, a substituent precursor comprises a mixture of two or more substituent precursors.

As used herein, a "cyclodextrin derivative" is used interchangeably with a "derivatized cyclodextrin" and refers to a cyclodextrin in which one or more —OH groups is replaced with an —O—R group, wherein R is a substituent other than hydrogen.

The concentrations of the reaction components (cyclodextrin starting material, substituent precursor, and an optional catalyst) can be independently or dependently varied as needed to provide a cyclodextrin derivative having a target/desired set of properties. In some embodiments, the concentration of cyclodextrin starting material (as the non-salt or salt form) is within the range of 1% to 95%, 10% to 95%, 10% to 90%, 15% to 85%, 20% to 85%, 25% to 85%, 30% to 85%, 40% to 85%, 50% to 85%, 60% to 85%, 60% to 90%, 65% to 95%, 70% to 95%, or 75% to 95% by weight of the feedstock.

Molar ratios of components can be varied as needed to provide the derivatized cyclodextrin. The substituent precursor is generally present in molar excess relative to the cyclodextrin starting material (i.e., a molar ratio of 1:1 or greater), which ensures an average degree of substitution of at least 1 or more. In some embodiments, the molar ratio of a substituent precursor to a cyclodextrin starting material is 1:1 to 500:1, 1:1 to 400:1, 1:1 to 300:1, 1:1 to 200:1, 1:1 to 150:1, 1:1 to 100:1, 1:1 to 75:1, 1:1 to 50:1, 1:1 to 40:1, 1:1 to 30:1, 1:1 to 25:1, 1:1 to 20:1, 1:1 to 15:1, 9:1 to 15:1, 5:1 to 9:1, 5:1 to 10:1, 6:1 to 12:1, 6:1 to 11:1, 6.5:1 to 10:1, 6.5:1 to 9.5:1, 6.5:1 to 9:1, 6.5:1 to 8.5:1, 6.5:1 to 8:1, 6.5:1 to 7:1, or 7:1 to 8:1, or 1:1 to 5:1.

When determining the molar ratio of substituent precursor to cyclodextrin or of catalyst to cyclodextrin, it may be necessary to account for the number of equivalents of reactive functional groups per molecule of cyclodextrin, substituent precursor and catalyst. A mole of cyclodextrin includes varying equivalents of reactive hydroxyl groups depending upon the ring size of the cyclodextrin. β-cyclodextrin includes 21 equivalents per mole: γ-cyclodextrin includes 24 equivalents per mole; and α-cyclodextrin includes 18 equivalents per mole. A mole of substituent precursor generally includes 1 or 2 equivalents per mole depending upon the identity of the substituent precursor. An optional catalyst generally includes 1, 2 or 3 equivalents per mole depending upon the identity thereof.

The molar ratio of a substituent precursor to a cyclodextrin starting material can be varied as needed to provide the derivatized cyclodextrin having a predetermined average degree of substitution. Table 2 below provides some approximate values for the ranges of the molar ratio of substituent precursor (such as butane sultone) to cyclodextrin starting material in order to achieve a target ADS.

TABLE 2

| Target ADS | Approximate Molar ratio of Substituent Precursor:Cyclodextrin Starting Material |
|---|---|
| <4 | 1:1-5:1 |
| 2 to 12 | 3:1-18:1 |
| 3 to 7 | 5:1-14:1 |
| >7 to 12 | 9:1-15:1 |
| >12 | >15:1 |

In general, the approximate molar ratio ("MR") of a substituent precursor (having a single reaction equivalent per mole) to the molar ratio of a cyclodextrin starting material required to achieve a target ADS ("T-ADS") can be calculated according to formula (1):

$$MR = X(T\text{-}ADS) \quad (1)$$

wherein X≥1. In general, X is 1 to 20, 1.05 to 17, 1.1 to 15, 1.25 to 12.5, 1.5 to 10, 1.75 to 10, 2 to 10, 2.25 to 10, 2.5 to 10, 2.75 to 10, 3 to 10, 1 to 10, 1.1 to 8, 1.1 to 7, 1.1 to 6, 1.1 to 5, 1.1 to 4, 1.1 to 3, 1.1 to 2.75, 1.1 to 2.5, 1.1 to 2.25, 1.1 to 2, 1.1 to 1.9, 1.1 to 1.8, 1.1 to 1.7, 1.1 to 1.6, 1.1 to 1.5, 1.1 to 1.4, 1.1 to 1.3, 1.1 to 1.25, or 1.1 to 1.2.

In some embodiments, a substituent precursor is unstable, e.g., thermolytically, hydrolytically, photolytically, and/or electrolytically unstable, under conditions present before or during the reacting. In order to compensate for degradation of a substituent precursor, the molar ratio of a substituent precursor to a cyclodextrin starting material can be increased. For example, butane sultone is thermolytically and/or hydrolytically unstable in aqueous solution at temperatures above 40° C., and the butane sultone can thus be used in excess in order to provide a cyclodextrin derivative having a target ADS. In some embodiments, a ratio of a substituent precursor to a cyclodextrin starting material is increased by 10% to 1000%, 10% to 500%, 10%/o to 400%, 10% to 300%, 10% to 200%, 10% to 150%, 10% to 125%, 10% to 100%, 10% to 75%, 10% to 50%, or 50% to 100%, 10%, 20%, 30%, 50%, 75%, 100%, 125%, 150%, 200%, 300%, 400%, 500%, or 1000% relative to a ratio useful to achieve a desired ADS under non-degrading reaction conditions.

Combinations of particular components can be used to prepare cyclodextrin derivatives as follows:
- sulfoalkyl ether cyclodextrin derivatives can be prepared by a process employing: one or more underivatized cyclodextrin starting materials; one or more sulfoalkylating agents; or one or more alkalinizing agents;
- hydroxyalkyl ether cyclodextrin derivatives can be prepared by a process employing: underivatized cyclodextrin starting materials; one or more hydroxyalkylating agents; or one or more alkalinizing agents;
- alkyl ether cyclodextrin derivatives can be prepared by a process employing: one or more underivatized cyclodextrin starting materials; one or more alkylating agents; or one or more alkalinizing agents;
- sulfoalkyl ether-alkyl ether cyclodextrin derivatives can be prepared by a process employing: one or more underivatized cyclodextrin starting materials; one or more sulfoalkylating agents; one or more alkylating agents; or one or more alkalinizing agents;
- sulfoalkyl ether-alkyl ether cyclodextrin derivatives can be prepared by a process employing: one or more SAE-CD derivatives as cyclodextrin starting materials; one or more alkylating agents; or one or more alkalinizing agents;
- sulfoalkyl ether-alkyl ether cyclodextrin derivatives can be prepared by a process employing: one or more AE-CD derivatives as cyclodextrin starting materials; one or more sulfoalkylating agents; or one or more alkalinizing agents;
- hydroxyalkyl ether-alkyl ether cyclodextrin derivatives can be prepared by a process employing: one or more AE-CD derivatives as cyclodextrin starting materials; one or more hydroxyalkylating agents; or one or more alkalinizing agents; and
- hydroxyalkyl ether-sulfoalkyl ether cyclodextrin derivatives can be prepared by a process employing: one or more underivatized cyclodextrin starting materials; one or more hydroxyalkylating agents; one or more sulfoalkylating agents, or one or more alkalinizing agents.

A "catalyst" refers to a compound capable of promoting and/or accelerating a reaction between a cyclodextrin starting material and a substituent precursor. In some embodiments, the reactivity of a substituent precursor can be enhanced by reacting it with an optional catalyst to form a reactive intermediate that then reacts with a cyclodextrin starting material. A catalyst is optionally present in an amount sufficient to promote and/or accelerate a reaction. In some embodiments, a catalyst is present in a sub-stoichiometric amount, a stoichiometric amount, or a stoichiometric excess (i.e., a molar excess). In some embodiments, the molar ratio of an optional catalyst to a cyclodextrin starting material exceeds the molar ratio of substituent precursor to cyclodextrin starting material.

Catalysts suitable for optional use with the present invention include, but are not limited to, an alkalinizing agent (e.g., an alkali metal hydroxide, a transition metal hydroxide, a transition metal oxide, an alkali metal bicarbonate, a transition metal bicarbonate, an alkali metal borate, a transition metal borate, an alkali metal hydride, a transition metal hydride, and the like), an acidifying agent, a phase transfer catalyst, an enzyme, and combinations thereof. Representative alkalinizing agents suitable for use as a catalyst include: magnesium oxide, magnesium hydroxide, calcium oxide, calcium hydroxide, manganese oxide, manganese hydroxide, and combinations thereof.

An "alkalinizing agent" refers to a compound used to provide alkaline medium. An alkalinizing agent or combination of two or more alkalinizing agents can be used as a catalyst herein. If an alkalinizing agent is available in liquid form (either at ambient temperature or at a temperature up to 200° C. or more), then it can also be used as a reaction medium in non-aqueous or aqueous form. Alkalinizing agents include, by way of example and without limitation, metal hydroxide, metal oxide, metal hydride, alkali metal hydroxide, transition metal hydroxide, transition metal oxide, alkali metal bicarbonate, transition metal bicarbonate, alkali metal borate, transition metal borate, alkali metal hydride, transition metal hydride, magnesium oxide, magnesium hydroxide, calcium oxide, calcium hydroxide, manganese oxide, manganese hydroxide, potassium hydroxide, sodium borate, sodium carbonate, tribasic phosphate, dibasic carbonate, sodium bicarbonate, sodium hydroxide, others known to those of ordinary skill in the art, and combinations thereof.

An "acidifying agent" refers to a compound used to provide an acidic medium. Acidifying agents include, by way of example and without limitation, mineral acids, acetic acid, acidic amino acids, citric acid, fumaric acid and other α-hydroxy acids, hydrochloric acid, ascorbic acid, phosphoric acid, sulfuric acid, tartaric acid, nitric acid, and others known to those of ordinary skill in the art.

A "buffering agent" refers to a compound used to resist change in pH upon dilution or addition of acid or alkali. Buffering agents include, by way of example and without limitation, acetic acid, sodium acetate, adipic acid, sulfuric acid, benzoic acid, sodium benzoate, boric acid, sodium borate, citric acid, glycine, maleic acid, monobasic sodium phosphate, dibasic sodium phosphate, HEPES, lactic acid, tartaric acid, potassium metaphosphate, potassium phosphate, monobasic sodium acetate, sodium sulfate, magnesium sulfate, sodium bicarbonate, tris-(hydroxymethyl)

aminomethane, sodium tartrate, sodium citrate anhydrous and dihydrate, and others known to those of ordinary skill in the art.

In some embodiments, an optional catalyst comprises an alkalinizing agent, and the substituent precursor is selected from: a sulfoalkylating agent, an alkylating agent, a hydroxyalkylating agent, and combinations thereof.

In some embodiments, an optional catalyst is present in a concentration of 0.1% to 50% by weight of the feedstock.

The molar ratio of an optional catalyst to a cyclodextrin starting material can vary as indicated for the molar ratio of substituent precursor to cyclodextrin starting material, except that the former molar ratios can be higher if needed. In some embodiments, a molar ratio of an optional catalyst to a cyclodextrin starting material is 0.1:1 to 30:1, 0.1:1 to 26:1, 0.5:1 to 23:1, 1:1 to 21:1, 1.25:1 to 19:1, 1.5:1 to 18:1, 1.5:1 to 16:1, 1.5:1 to 14:1, 1.5:1 to 12:1, 2:1 to 22:1, 2:1 to 19:1, 2:1 to 16:1, 2:1 to 14:1, 1.1:1 to 6:1, 1.5:1 to 6:1, 6:1 to 11:1, 6:1 to 10:1, 11:1 to 18:1, 10:1 to 20:1, 10:1 to 18:1, 15:1 to 26:1, 17:1 to 25:1, 1:1 to 26:1, 1:1 to 30:1, 1:1 to 50:1, 0.5:1 to 50:1, 1.1:1 to 55:1, or 0.1:1 to 50:1.

If present, an optional catalyst is typically in molar excess relative to a substituent precursor. Thus, an optional catalyst and a substituent precursor are typically present in a ratio of 1:1 or greater. In some embodiments, a molar ratio of an optional catalyst to a substituent precursor is 1:1 to 20:1, 0.5 to 40:1, 0.1:1 to 50:1, 1.1:1 to 50:1, 1.1:1 to 55:1, 1.1:1 to 40:1, 1.1:1 to 30:1, 1.1:1 to 20:1, 1.1:1 to 10:1, 1.1:1 to 5:1, 1.1:1 to 2.5:1, 1.1:1 to 2:1, or 1.1:1 to 1.5:1.

A "feedstock" or "flowing feedstock" is used interchangeably with the term "medium" and/or "reaction medium," and all refer to a flowing mass comprising one, two, three or more starting materials as a liquid, solid, suspension, dispersion, or semi-solid. A flowing feedstock can comprise an extruded medium and/or a liquid medium, either of which can be aqueous or non-aqueous. Reactants (e.g., a cyclodextrin starting material, a substituent precursor and an optional catalyst) are present in a flowing feedstock in solid, semi-solid, gaseous, suspension, dispersion, or liquid form. An aqueous liquid medium can comprise water, buffered water, or a combination of an organic liquid and water and/or buffered water. A non-aqueous liquid medium is substantially free from water. Thus, a feedstock of the present invention can comprise an aqueous medium substantially free of an organic liquid (other than substituent precursor or other specified agent); an aqueous medium that includes an organic liquid (other than substituent precursor or other specified agent), or a non-aqueous medium.

In some embodiments, a solvent for use with the method of the present invention is miscible with water. Solvents suitable for use with the present invention can also include water immiscible organic solvents. Solvents suitable for use with the present invention include, but are not limited to, water, an alcohol (e.g., methanol, ethanol, propanol, butanol, propylene glycol, and the like), an ether (e.g., diethyl ether, tetrahydrofuran, and the like), a ketone (e.g., formaldehyde, acetone, and the like), a nitrile (e.g., acetonitrile and the like), a sulfoxide (e.g., dimethylsulfoxide and the like), an amide (e.g., dimethylformamide, dimethylacetamide, N-methylpyrrolidone, and the like), an ester (e.g., ethyl acetate, and the like), a chlorinated solvent (e.g., methylene chloride, chloroform, 1,2-dichloroethane, chlorobenzene, and the like), an oil (e.g., paraffin, mineral oil, organic oil, a food oil, and the like), a water-soluble polymer (e.g., polyethylene glycol, polypropylene glycol, and the like), and combinations thereof.

In some embodiments, a solvent for use with the present invention is a solvent in which a parent cyclodextrin (i.e., a cyclodextrin starting material) has a solubility of 1 mg/mL or higher, 10 mg/mL or higher, 50 mg/mL or higher, 100 mg/mL of higher, 250 mg/mL or higher, 500 mg/mL or higher, or 1 g/mL or higher.

The reaction components of cyclodextrin starting material, catalyst and substituent precursor are independently present in the liquid medium in dissolved form, solid suspension form, liquid dispersion form, or a combination thereof. The cyclodextrin starting material can be present in dissolved form and/or suspended form in the liquid medium. The catalyst can be present in dissolved form, dispersed liquid form, and/or suspended solid form in the liquid medium. The substituent precursor can be present in dissolved form, in dispersed liquid form, and/or suspended solid form in the liquid medium, or the substituent precursor can be present in gas form.

A reaction medium can comprise aqueous or non-aqueous medium and/or can comprise a protic and/or non-protic liquid. Organic liquid(s) can be used, alone or with aqueous medium, as suitable reaction medium. Suitable protic and non-protic organic liquids include, for example, ethanol, propanol, butanol, glycerin, glycerol, polyethylene glycol, propylene glycol, glyme, diglyme, poly(propylene glycol), poloxomer, poly(vinyl pyrrolidone), pyridine, tetrahydrofuran, acetonitrile, dimethylformamide, methylformamide, N-methylpyrrolidone, oil, alcohol, isopropanol, hexadecyl alcohol, glycerol ketals (such as 2,2-dimethyl-1,3-dioxolane-4-methanol), diethyl ether, dimethyl ether, dimethylketone, ethyl methyl ether, petroleum hydrocarbon, mineral oil, petrolatum, or a combination thereof. Exemplary oils include, for example, fixed oils, such as peanut oil, sesame oil, cottonseed oil, corn oil, and olive oil, fatty acids, such as oleic acid, stearic acid, and isostearic acid; and fatty acid esters, such as ethyl oleate, isopropyl myristate, fatty acid glycerides, and acetylated fatty acid glycerides. In some embodiments, the liquid medium is selected from the group consisting of water, aqueous buffer, alcohol, glycol, ether, oil, ketone, and a combination thereof.

In some embodiments, the amount of water in a feedstock is minimized prior to the reacting. Minimizing or eliminating water from a feedstock can prevent hydrolytic degradation of a substituent precursor. In some embodiments, a non-aqueous organic reaction medium can provide a cyclodextrin derivative having a controlled regiochemical distribution of functional (derivative) groups.

In some embodiments, the flowing feedstock comprises an aqueous liquid and an organic liquid, wherein the volume ratio of aqueous liquid to organic liquid ranges from 0.05: 99.95 to 99.95:0.05, 0.1:99.9 to 99.9:0.1, 0.5:99.5 to 99.5: 0.5, 1:99 to 99:1, 2.5:97.5 to 97.5:2.5, 5:95 to 95:5, 7.5:92.5 to 92.5:7.5, 10:90 to 90:10, 15:85 to 85:15, 20:80 to 80:20, 25:75 to 75:25, 60:40 to 40:60, 50:50, 0.1:99.9 to 40:60, 1:99 to 25:75, 1:99 to 20:80, 1:99 to 15:85, 1:99 to 10:90, 1:99 to 7.5:92.5, 1:99 to 5:95, 0.1:99.9 to 10:90, 0.1:99.9 to 7.5:92.5, or 0.1:99.9 to 5:95.

In some embodiments, a process of the present invention comprises reacting in a continuous or semi-continuous manner by providing a feedstock comprising a liquid or gas medium, a cyclodextrin starting material, a substituent precursor, and an optional catalyst; and continuously or semi-continuously flowing the feedstock into a reactor and flowing out of the reactor the raw product comprising a derivatized cyclodextrin. The reactor is maintained at a temperature and the flow rate and reactor volume provide a residence time sufficient to form a cyclodextrin derivative. The processes of the present invention can be operated in serial or parallel mode.

In some embodiments, the providing comprises a process selected from:

(i) mixing the cyclodextrin starting material with the optional catalyst to form a mixture, and mixing portions of the mixture with portions of the substituent precursor to form the feedstock;

(ii) mixing the cyclodextrin starting material with the substituent precursor to form a mixture, and mixing portions of the mixture with portions of the optional catalyst to form the feedstock;

(iii) mixing the optional catalyst with the substituent precursor to form a mixture, and mixing the mixture with portions of the cyclodextrin starting material to form the feedstock; and (iv) mixing portions of the cyclodextrin starting material, the substituent precursor, and the optional catalyst substantially simultaneously to form the feedstock.

FIG. 1A provides a general process flow diagram for a continuous or semi-continuous flow-through process and equipment assembly of the present invention, which comprises a starting material system, a portionwise flow-through reactor system and a post-reaction processing system. The starting material system comprises the cyclodextrin starting material, substituent precursor, optional catalyst, liquid medium, and any necessary equipment and controls. The starting material system combines the starting material and provides a flowing feedstock which is conducted to the reactor system. Each of the individual operations/steps of the starting material system can be independently conducted in a batchwise or portionwise (semi-continuous or continuous) manner. The flow-through reactor system continuously or semi-continuously receives and conducts portions of the flowing feedstock for a residence time sufficient, and at a temperature and pressure sufficient to permit reaction of the ingredients and formation of a flowing raw product comprising the cyclodextrin derivative. The raw product is conducted to the post-reaction processing system for purification, sterilization, isolation, packaging and/or storage of the cyclodextrin derivative product. Each of the individual operations/steps of the post-reaction processing system can be independently conducted in a batchwise or portionwise manner. Exemplary combinations of the modes of operation of the process and equipment assembly of the present invention are summarized below in Table 3.

TABLE 3

| Starting material system | Flow-through reactor system | Post-reaction processing system |
|---|---|---|
| Batchwise | Continuous | Batchwise |
| Batchwise | Continuous | Continuous* |
| Continuous* | Continuous | Continuous* |
| Continuous* | Continuous | Batchwise |
| Batchwise | Semi-continuous | Batchwise |
| Batchwise | Semi-continuous | Continuous* |
| Continuous* | Semi-continuous | Continuous* |
| Continuous* | Semi-continuous | Batchwise |

*Denotes an operation that can also be independently conducted semi-continuously instead of continuously As used herein, "continuous" refers to substantially constant or substantially uninterrupted operation for an extended period of time. A continuous step of the process is one wherein the step is conducted substantially uninterrupted for a period of time sufficient to complete processing of at least a major portion of a batch of material being processed. For example, a continuous derivatization step (such as can occur in the flow-through reactor system) is one wherein portions of feedstock are fed sequentially into the flow-through reactor substantially uninterrupted to form raw product on a substantially uninterrupted basis. A continuous process is one wherein plural steps of the process are conducted substantially uninterrupted for a period of time sufficient to complete processing of at least a major portion of a batch of material being processed. A continuous process comprises two or more continuous steps of the process and/or two or more continuously operated systems.

As used herein, "semi-continuous" refers to a process or step bridging the gap between batchwise and continuous process or steps, respectively. A semi-continuous step is one wherein the step is conducted substantially uninterrupted for a shortened period of time sufficient to permit processing of a minor portion of a batch of material being processed, then a planned interrupt of the step, then the step is continued to permit processing of another minor portion of a batch of material being processed, wherein the processing and interruption are repeatedly as need to complete processing of at least a major portion of a batch of material being processed.

In some embodiments, a flow-through reactor is operated continuously or semi-continuously; the starting material system is operated batchwise, continuously or semi-continuously; and the post-reaction processing system is operated batchwise, continuously or semi-continuously. Accordingly, the invention also provides a combination process comprising: batchwise preparation of cyclodextrin starting material supply, catalyst supply and substituent precursor supply; continuous or semi-continuous formation of cyclodextrin derivative raw product in a flow-through reactor; and batchwise, continuous or semi-continuous separation, purification, sterilization, isolation, collection and/or storage of cyclodextrin derivative final product.

The present invention also includes embodiments wherein a batch-type process is modified according to the invention by applying the methods described herein to provide a continuous or semi-continuous process for the preparation of a cyclodextrin derivative. In some embodiments, the invention provides a modified version of the batch-type process of U.S. Pat. No. 6,153,746, which is hereby incorporated by reference in its entirety, wherein the process has been modified according to the invention described herein to provide SAE-CD as a product of a flow-through reactor. Accordingly, the invention provides a process for the preparation of a sulfoalkyl ether cyclodextrin derivative comprising: batchwise preparation of cyclodextrin starting material supply, alkalinizing agent supply and sulfoalkylating agent supply: continuous or semi-continuous contacting of portions of cyclodextrin starting material supply, portions of alkalinizing agent supply and portions of sulfoalkylating agent supply; continuous or semi-continuous formation of portions of sulfoalkyl ether cyclodextrin derivative-containing raw product in a flow-through reactor: and batchwise, continuous or semi-continuous separation, purification, sterilization, isolation, collection and/or storage of sulfoalkyl ether cyclodextrin derivative final product. In some embodiments, the sulfoalkylating agent is 1,4-butane sultone, the alkalinizing agent is a metal hydroxide, metal oxide or metal hydride, and the cyclodextrin starting material is underivatized α-cyclodextrin, β-cyclodextrin, γ-cyclodextrin, or a combination thereof.

FIG. 1B depicts another process flow diagram of the process and assembly of the present invention. The starting material system of FIG. 1A is separated into two components in FIG. 1B: a staring material supply and a portionwise starting material feed system, which forms the flowing feedstock in one or more conduits. The flowing feedstock is conducted continuously or semi-continuously portionwise through the portionwise flow-through reactor system to form the flowing raw product milieu, which is conducted to a product separation and/or purification system. The raw product is also, optionally, further processed in a product isolation system, product sterilization, product packaging, product collection system, and/or product storage system.

Process parameters can be altered as needed either dependently or independently to provide a cyclodextrin derivative possessing the desired properties, such as a target degree of substitution or primary regioisomeric substitution pattern. Exemplary process parameters include molar ratios of reactants in a feedstock, a pH of the feedstock, a temperature of the feedstock, the temperature of the reactor, the pressure of the feedstock, residence time of the feedstock or reaction in the flow-through reactor, flow rate of the feedstock or reaction in the flow-through reactor, concentration of cyclodextrin starting material in the feedstock or reaction milieu, concentration of substituent precursor in the feedstock or reaction milieu, concentration of catalyst in the feedstock or reaction milieu, and combinations thereof.

A "residence time" refers to an amount of time a reactant and/or a product thereof is present within a flow-through reactor. Generally, a residence time is sufficient to react a cyclodextrin starting material and a substituent precursor to provide a cyclodextrin derivative. Because a flow-through reactor typically has a fixed volume, a residence time can be determined by the volume and flow rate. For a reactor having a fixed volume, the residence time is determined by dividing the volume of the reactor (mL) by the flow rate (mL/min). Thus, the residence time can be increased by reducing the flow rate or can be decreased by increasing the flow rate. Likewise, at a constant flow rate, the residence time can be increased by increasing the reactor volume or can be decreased by decreasing the reactor volume.

The residence time of a reactant in a reactor can be varied as needed to provide a desired extent of derivatization (degree of substitution) and/or yield of cyclodextrin derivative and/or to minimize degradation of a cyclodextrin starting material and/or substituent precursor during the reacting. In some embodiments, a residence time is 0.5 seconds ("sec") to 5 hours ("hrs"), 0.5 sec to 4 hrs, 0.5 sec to 3 hrs, 0.5 sec to 2.5 hrs, 0.5 sec to 2 hrs, 1 sec to 1.5 hrs, 1 sec to 1.25 hrs, 1 sec to 1 hr, 1 sec to 45 minutes ("min"), 1 sec to 30 min, 1 sec to 25 min, 1 sec to 20 min, 1 sec to 15 min, 1 sec to 10 min, 1 sec to 9 min, 1 sec to 8 min, 1 sec to 7 min, 1 sec to 6 min, 1 sec to 5 min, 1 sec to 4 min, 1 sec to 3 min, 1 sec to 2 min, 1 sec to 1.75 min, 1 sec to 1.5 min, 1 sec to 1.25 min, 1 sec to 1.1 min, 1 sec to 1 min, 1 sec to 50 sec, 1 sec to 45 sec, 1 sec to 40 sec, 1 sec to 30 see, 1 sec to 30 sec, 1 sec to 25 sec, 1 sec to 20 sec, 1 sec to 15 sec, 1 Sec to 10 sec, 1 sec to 5 sec, 1 min to 10 min, 10 min to 20 min, 20 min to 30 min, 30 min to 45 min, 45 min to 75 min, 75 min to 105 min, or 105 min to 120 min.

The temperature of the feedstock can be controlled to promote and/or optimize a reaction between a cyclodextrin starting material and a substituent precursor. Generally, a temperature is at or below the degradation temperature of a cyclodextrin starting material, a substituent precursor, an optional catalyst, and/or a cyclodextrin derivative. In some embodiments, a process further comprises pre-heating the cyclodextrin starting material and pre-heating the substituent precursor. In some embodiments, a temperature of a liquid medium is controlled before, during and/or after the reacting at 5° C. to 200° C., 10° C. to 200° C., 20° C. to 200° C., 30° C. to 200° C., 40° C. to 200° C., 10° C. to 180° C., 20° C. to 180° C., 30° C. to 180° C., 40° C. to 180° C., 50° C. to 180° C., 60° C. to 180° C., 40° C. to 175° C., 50° C. to 175° C., 60° C. to 175° C., 70° C. to 175° C., 80° C. to 175° C., 90° C. to 175° C., 100° C. to 175° C., 110° C. to 175° C., 120° C. to 175° C., 130° C. to 175° C., 140° C. to 175° C., 150° C. to 175° C., 160° C. to 175° C., 70° C. to 180° C., 20° C. to 170° C. 30° C. to 170° C., 40° C. to 170° C., 50° C. to 170° C., 60° C. to 170° C., 70° C. to 170° C., 30° C. to 165° C., 40° C. to 160° C., 50° C. to 160° C., 60° C. to 160° C., 70° C. to 160° C., 80° C. to 160° C., 90° C. to 160° C., 100° C. to 160° C. 50° C. to 155° C. 60° C. to 150° C., or 70° C. to 145° C.

In some embodiments, the feedstock has a residence time in the reactor of 0.5 sec to 5 hours. In some embodiments, the feedstock has a residence time in the reactor of 0.5 sec to 30 minutes, and the reactor temperature is 70° C. to 200° C.

In some embodiments, a process of the present invention is performed at a controlled pressure (e.g., a reduced pressure, ambient pressure, or elevated pressure). In some embodiments, individual steps of a process are performed at the same or different pressures. For example, reacting can occur at a first pressure range, and purifying and/or isolating can occur at the same or a different pressure. Generally, reacting is performed at a pressure sufficient to react a substituent precursor with a cyclodextrin starting material to provide a cyclodextrin derivative. In some embodiments, a pressure is selected to minimize or avoid boiling, volatilization, or evaporation of a liquid medium, a catalyst or a substituent precursor during the reacting. In some embodiments, a process, or a portion thereof, of the present invention is performed at a pressure of 1 pound per square inch ("psi") to 400 psi, 1 psi to 300 psi, 1 psi to 250 psi, 5 psi to 200 psi, 5 psi to 175 psi, 5 psi to 150 psi, 5 psi to 125 psi, 5 psi to 100 psi, 10 psi to 250 psi, 10 psi to 100 psi, 10 psi to 75 psi, 25 psi to 250 psi, 50 psi to 250 psi, or 75 psi to 250 psi, or a combination thereof.

In some embodiments, temperature and pressure are adjusted during the reacting such that process temperatures exceeding a boiling point of a liquid medium or a substituent precursor are used. In some embodiments, a gaseous or volatile substituent precursor is used, and a pressure is selected such that at least 5%, 10%, 15%, 20%, 25%, 30%, 40%, 50%, 60%, 70%, 80%, 90%, or 95% by weight of the substituent precursor present in a reactor is dissolved or dispersed within a liquid medium.

In some embodiments, a pH of a liquid medium (a feedstock) is controlled before, after, and/or during the reacting. In some embodiments, a pH of a liquid medium is greater than 7 at least during the reacting. In some embodiments, a pH of a liquid medium during the reacting is 7 to 18, 7 to 14, 8 to 14, 8.5 to 13, 8.5 to 12, 8.5 to 11.5, 8.5 to 11.5, 9 to 11.5, 9 to 14, 9 to 13, 9 to 12, 10 to 14, 10 to 13, 10 to 12, 10 to 11, or 9 to 11. In some embodiments, a pH of a liquid medium during the reacting is 0 to less than 7, 0.5 to 6.5, 1 to 6, 1 to 5, 1 to 4.5, 1 to 4, 1 to 3.5, 1 to 3, or 1 to 2.5.

In some embodiments, the feedstock has a pH of 9 to 14, the feedstock has a residence time in the reactor of 0.5 sec to 20 minutes, and the temperature of the reactor is 90° C. to 160° C.

In some embodiments, a reactor temperature is 30° C. to 200° C., the residence time of the feedstock in the reactor is 0.5 sec to 4 hours, the concentration of cyclodextrin starting material in the feedstock is 1% to 95% by weight, the concentration of a substituent precursor in the feedstock is 1% to 50% by weight, the concentration of a catalyst in the feedstock is 0.1% to 50% by weight, and the cyclodextrin derivative is present in a raw product in a concentration of 50%0/to 100% by weight.

Cyclodextrin derivatives possessing an average degree of substitution of 1 to 4 can be prepared with a process employing: β-cyclodextrin starting material, substituent precursor, and catalyst, a residence time of 1 sec to 20 min, a reaction temperature of 90° C. to 160° C., and a feedstock pH of 9 to 13 or higher, wherein the molar ratio of substituent precursor to cyclodextrin starting material is 1:1 to 5:1 or higher, and the molar ratio of catalyst to cyclodextrin starting material is 1.1:1 to 5.1:1 or higher.

A cyclodextrin derivative having an ADS of 4 to 7 can be prepared by a process employing: β-cyclodextrin starting material, substituent precursor, and an optional catalyst, a residence time of 1 sec to 20 min, a reaction temperature of 90° C. to 160° C., and a feedstock pH of 9 to 13 or higher, wherein the molar ratio of substituent precursor to cyclodextrin starting material is 5:1 to 10:1 or higher, and the molar ratio of an optional catalyst to the cyclodextrin starting material is 5.5:1 to 11:1 or higher.

A cyclodextrin derivative having an ADS of 7 to 12 can be prepared by a process employing: β-cyclodextrin starting material, substituent precursor, and an optional catalyst, a residence time of 1 sec to 20 min, a reaction temperature of 90° C. to 160° C., and a feedstock pH of 9 to 13 or higher, wherein the molar ratio of substituent precursor to cyclodextrin starting material is 10:1 to 15:1 or higher, and the molar ratio of an optional catalyst to the cyclodextrin starting material is 11:1 or 16:1 or higher.

In some embodiments, a cyclodextrin derivative precipitates from a reaction medium after its formation. As a result, a process of the present invention can prepare cyclodextrin derivatives having a narrow span and moderate to low degree of substitution. In some embodiments, a cyclodextrin derivative prepared according to a process of the present invention has a span of 1 to 8, 1 to 7, 1 to 6, 1 to 5, 1 to 4, 1 to 3, or 1 to 2, and an ADS of 1 to 7, 1 to 6, 1 to 5, 1 to 4, 1 to 3, or 1 to 2.

In some embodiments, the primary distribution of substituents is C3>C2>C6, C2>C3>C6. C6>C2>C3, C6>C3>C2, C3>C6>C2, or C2>C6>C3.

Combinations of process parameters can be varied as follows to provide cyclodextrin derivatives possessing the specified properties:

As used herein, a "raw product" refers to a reaction medium comprising a cyclodextrin derivative immediately after the reacting has occurred. A raw product is a material that has not been refined or otherwise purified after a reaction between a cyclodextrin starting material and a substituent precursor is complete. In addition to a cyclodextrin derivative, a raw product can include, e.g., a cyclodextrin starting material, a substituent precursor in an amount of 1% or less (relative to the amount of substituent precursor present during the reacting), an optional catalyst, a side product, and the like.

Not being bound by any particular theory, the present invention provides significant improvements over previously known processes for preparing cyclodextrin derivatives because the raw product prepared by a process of the present invention does not require removal of an unreacted substituent precursor via a lengthy heating process. In some embodiments, the raw product also provides significantly reduced concentrations of side products, degradants, and/or unreacted starting materials in addition to a substituent precursor.

In some embodiments, a process of the present invention excludes a step-wise addition of the substituent precursor to a cyclodextrin starting material in a batch-type reactor to form a batch of raw product comprising a derivatized cyclodextrin. Thus, in some embodiments the process of the present invention comprises adding a substituent precursor with a cyclodextrin starting material in a single step, reacting the substituent precursor and the cyclodextrin starting material for a time sufficient, at a temperature sufficient, and with an optional catalyst sufficient to provide a raw product comprising a cyclodextrin derivative, which contains 1% or less of an unreacted substituent precursor (based on the amount of substituent precursor initially added to the reaction).

As used herein, the yield of cyclodextrin derivative in a raw product refers to the chemical yield of cyclodextrin derivative in a portion of the reaction medium that exits a reactor, based upon the amount of cyclodextrin starting material in the corresponding feedstock entering the reactor. For example, if a portion of feedstock entering the reactor comprises 1 mmol of a cyclodextrin starting material and the raw product comprises 0.9 mmol of a cyclodextrin derivative, then the yield is 90% (i.e., 0.9/1). In some embodiments, the yield of the cyclodextrin derivative is 10% to 100%, 15% to 100%, 20% to 100%, 25% to 100%, 30% to 10%, 35% to 100%, 40% to 100%, 45% to 100%, 50% to 100%, 55% to 100%, 60% to 100%, 65% to 100%, 70% to 100%, 75% to 100%, 80% to 100%, 85% to 100%, 90% to 100%, 95% to 100%, or 97.5% to 100%. In some embodiments, the derivatized cyclodextrin is present in the raw product in a yield of 70% or greater, 75% or greater, 80% or greater, 85% or greater, 90% or greater, 95% or greater, 98% or greater, 99% or greater, 99.5% or greater, or 100%, based upon the amount of the cyclodextrin starting material.

In some embodiments, a raw product of a process of the present invention comprises 1% or less, 0.5% or less, 0.1% or less, 0.05% or less, 0.01% or less, 0.005% or less, 0.001%/or less, 0.0005% or less, or 0.0001% or less of an unreacted substituent precursor, based upon the amount of substituent precursor present in the reaction medium prior to the reacting. Thus, a reaction of the present invention utilizing 1 mole of a substituent precursor would provide a raw product comprising 0.01 mole or less, 0.005 mole or less, 0.001 mole or less, 0.0005 mole or less, 0.0001 mole or less, 0.00005 mole or less, 0.00001 mole or less, 0.000005 mole or less, or 0.000001 mole or less of the unreacted substituent precursor in the raw product.

In some embodiments, a raw product is a clear, opaque, or white solution. In some embodiments, a raw product is substantially free from an absorption in the visible spectrum at a wavelength of 450 nm or greater.

In some embodiments, a process further comprises neutralizing the raw product by adding an appropriate amount of an acid or a base to the raw product. For example, an acid can be added to basic raw product solution in order to provide a solution having a pH of 6.5 to 7.5, or a pH of 7.

In some embodiments, an unreacted substituent precursor is present in a raw product in an amount that is sufficient for the substituent precursor to be removed via a purification process such as, but not limited to, ultrafiltration, diafiltration, distillation, and the like, and combinations thereof.

In some embodiments, a substituent precursor present in the raw product is degraded by exposure to an elevated temperature, for example, 50° C. or higher, 60° C. or higher, 70° C. or higher, 80° C. or higher, 90° C. or higher, or 100° C. or higher. For example, 1,4-butane sultone ("BS") is thermolytically and/or hydrolytically unstable at temperatures above 60° C. in an aqueous medium.

In some embodiments, a process further comprises separating the derivatized cyclodextrin from the raw product, wherein the separating includes at least one of filtering, centrifuging, decanting, or a combination thereof.

The water soluble cyclodextrin derivative composition is optionally processed to remove the major portion of the underivatized parent cyclodextrin or other contaminants. In some embodiments, a process further comprises isolating the derivatized cyclodextrin, wherein the isolating includes at least one of drying, sterile filtering, concentrating, or a combination thereof. In some embodiments, a process further comprises purifying the derivatized cyclodextrin, wherein the purifying includes at least one of extracting, diafiltrating, dialyzing, treating with a carbon medium, treating with an adsorption medium, treating with a color-removal medium, or a combination thereof.

The final yield of cyclodextrin derivative (in isolated and/or purified or partially purified form) obtained at completion of the process will vary. The final yield of cyclodextrin derivative can range from 10% to 95%, 15% to 90%, 20% to 85%, 30% to 85%, 35% to 85%, 40% to 85%, 45% to 80%, 50% to 80%, 55% to 80%, 60% to 80%, 50% to 90%, 55% to 90%, 60% to 90%, 70% to 90%, 80% to 90%, 60% to 98%, 70% to 98%, 80% to 98%, 90% to 98%.

The present invention is also directed to a process for preparing a derivatized cyclodextrin, the process comprising:
combining in a liquid or gas medium a cyclodextrin starting material, a sulfoalkylating agent present in a molar excess relative to the cyclodextrin starting material, and an alkalinizing agent present in a molar excess relative to the one or more sulfoalkylating agents to form a feedstock; and
reacting the feedstock by continuously or semi-continuously flowing the feedstock into and out of a reactor for a residence time of 0.5 sec to 4 hours, 0.5 sec to 2 hours, 0.5 sec to 1 hour, 0.5 sec to 30 min, 0.5 sec to 20 min, 0.5 sec to 10 min, or 0.5 sec to 5 min at a temperature of 30° C. to 200° C., 40° C. to 190° C., 50° C. to 180° C., 60° C. to 170° C., or 70° C. to 160° C. and at a pressure of 1 bar or higher, 1.5 bar or higher, 2 bar or higher, 2.5 bar or higher, or 3 bar or higher to form a raw product comprising the derivatized cyclodextrin.

Cyclodextrin Derivatives

A "cyclodextrin derivative composition" (cyclodextrin derivative composition) is a composition having a degree of substitution or an average degree of substitution (ADS) for a specified substituent. A cyclodextrin derivative composition comprises a distribution of cyclodextrin derivative species differing in the individual degree of substitution specified substituent for each species, wherein the specified substituent for each species is the same.

The cyclodextrin derivative can be a water soluble cyclodextrin derivative, which is any cyclodextrin derivative exhibiting enhanced water solubility over its corresponding underivatized parent cyclodextrin and having a molecular structure based upon α-, β- or γ-cyclodextrin. In some embodiments, a derivatized cyclodextrin prepared by a process of the present invention has a solubility in water of 100 mg/mL or higher, or a solubility in water of less than 100 mg/mL.

The cyclodextrin can be derivatized with neutral, anionic or cationic substituents at the C2, C3, or C6 positions of the individual saccharides forming the cyclodextrin ring. Suitable water soluble cyclodextrin derivatives are described herein. The cyclodextrin derivative can also be a water insoluble cyclodextrin derivative or a cyclodextrin derivative possessing a lower water solubility than it corresponding underivatized parent cyclodextrin.

In some embodiments, the derivatized cyclodextrin includes a substituent selected from: a sulfoalkyl ether group, an ether group, an alkyl ether group, an alkenyl ether group, a hydroxyalkyl ether group, a hydroxyalkenyl ether group, a thioalkyl ether group, an aminoalkyl ether group, a mercapto group, an amino group, an alkylamino group, a carboxyl group, an ester group, a nitro group, a halo group, an aldehyde group, a 2,3-epoxypropyl group, and combinations thereof.

In some embodiments, mixed ether cyclodextrin derivatives include, by way of example, those listed in Table 4 below.

TABLE 4

| Mixed ether CD derivative | Mixed ether CD derivative | Mixed ether CD derivative |
| --- | --- | --- |
| Sulfobutyl-hydroxybutyl-CD (SBE-HBE-CD) | Sulfopropyl-hydroxybutyl-CD (SPE-HBE-CD) | Sulfoethyl-hydroxybutyl-CD (SEE-HBE-CD) |
| Sulfobutyl-hydroxypropyl-CD (SBE-HPE-CD) | Sulfopropyl-hydroxypropyl-CD (SPE-HPE-CD) | Sulfoethyl-hydroxypropyl-CD (SEE-HPE-CD) |
| Sulfobutyl-hydroxyethyl-CD (SBE-HEE-CD) | Sulfopropyl-hydroxyethyl-CD (SPE-HEE-CD) | Sulfoethyl-hydroxyethyl-CD (SEE-HEE-CD) |
| Sulfobutyl-hydroxybutenyl-CD (SBE-HBNE-CD) | Sulfopropyl-hydroxybutenyl-CD (SPE-HBNE-CD) | Sulfoethyl-hydroxybutenyl-CD (SEE-HBNE-CD) |
| Sulfobutyl-ethyl (SBE-EE-CD) | Sulfopropyl-ethyl (SPE-EE-CD) | Sulfoethyl-ethyl (SEE-EE-CD) |
| Sulfobutyl-methyl (SBE-ME-CD) | Sulfopropyl-methyl (SPE-ME-CD) | Sulfoethyl-methyl (SEE-ME-CD) |
| Sulfobutyl-propyl (SBE-PE-CD) | Sulfopropyl-propyl (SPE-PE-CD) | Sulfoethyl-propyl (SEE-PE-CD) |
| Sulfobutyl-butyl (SBE-BE-CD) | Sulfopropyl-butyl (SPE-BE-CD) | Sulfoethyl-butyl (SEE-BE-CD) |
| Sulfobutyl-carboxymethyl-CD (SBE-CME-CD) | Sulfopropyl-carboxymethyl-CD (SPE-CME-CD) | Sulfoethyl-carboxymethyl-CD (SEE-CME-CD) |
| Sulfobutyl-carboxyethyl-CD (SBE-CEE-CD) | Sulfopropyl-carboxyethyl-CD (SPE-CEE-CD) | Sulfoethyl-carboxyethyl-CD (SEE-CEE-CD) |
| Sulfobutyl-acetate-CD (SBE-AA-CD) | Sulfopropyl-acetate-CD (SPE-AA-CD) | Sulfoethyl-acetate-CD (SEE-AA-CD) |
| Sulfobutyl-propionate-CD (SBE-PA-CD) | Sulfopropyl-propionate-CD (SPE-PA-CD) | Sulfoethyl-propionate-CD (SEE-PA-CD) |
| Sulfobutyl-butyrate-CD (SBE-BA-CD) | Sulfopropyl-butyrate-CD (SPE-BA-CD) | Sulfoethyl-butyrate-CD (SEE-BA-CD) |
| Sulfobutyl-methoxycarbonyl-CD (SBE-MC-CD) | Sulfopropyl-methoxycarbonyl-CD (SPE-MC-CD) | Sulfoethyl-methoxycarbonyl-CD (SEE-MC-CD) |
| Sulfobutyl-ethoxycarbonyl-CD (SBE-EC-CD) | Sulfopropyl-ethoxycarbonyl-CD (SPE-EC-CD) | Sulfoethyl-ethoxycarbonyl-CD (SEE-EC-CD) |
| Sulfobutyl-propoxycarbonyl-CD (SBE-PC-CD) | Sulfopropyl-propoxycarbonyl-CD (SPE-PC-CD) | Sulfoethyl-propoxycarbonyl-CD (SEE-PC-CD) |
| Hydroxybutyl-hydroxybutenyl-CD (HBE-HBNE-CD) | Hydroxypropyl-hydroxybutenyl-CD (HPE-HBNE-CD) | Hydroxyethyl-hydroxybutenyl-CD (HEE-HBNE-CD) |
| Hydroxybutyl-ethyl (HBE-EE-CD) | Hydroxypropyl-ethyl (HPE-EE-CD) | Hydroxyethyl-ethyl (HEE-EE-CD) |
| Hydroxybutyl-methyl (HBE-ME-CD) | Hydroxypropyl-methyl (HPE-ME-CD) | Hydroxyethyl-methyl (HEE-ME-CD) |
| Hydroxybutyl-propyl (HBE-PE-CD) | Hydroxypropyl-propyl (HPE-PE-CD) | Hydroxyethyl-propyl (HEE-PE-CD) |

TABLE 4-continued

| Mixed ether CD derivative | Mixed ether CD derivative | Mixed ether CD derivative |
|---|---|---|
| Hydroxybutyl-butyl (HBE-BE-CD) | Hydroxypropyl-butyl (HPE-BE-CD) | Hydroxyethyl-butyl (HEE-BE-CD) |
| Hydroxybutyl-carboxymethyl-CD (HBE-CME-CD) | Hydroxypropyl-carboxymethyl-CD (HPE-CME-CD) | Hydroxyethyl-carboxymethyl-CD (HEE-CME-CD) |
| Hydroxybutyl-carboxyethyl-CD (HBE-CEE-CD) | Hydroxypropyl-carboxyethyl-CD (HPE-CEE-CD) | Hydroxyethyl-carboxyethyl-CD (HEE-CEE-CD) |
| Hydroxybutyl-acetate-CD (HBE-AA-CD) | Hydroxypropyl-acetate-CD (HPE-AA-CD) | Hydroxyethyl-acetate-CD (HEE-AA-CD) |
| Hydroxybutyl-propionate-CD (HBE-PA-CD) | Hydroxypropyl-propionate-CD (HPE-PA-CD) | Hydroxyethyl-propionate-CD (HEE-PA-CD) |
| Hydroxybutyl-butyrate-CD (HBE-BA-CD) | Hydroxypropyl butyrate-CD (HPE-BA-CD) | Hydroxyethyl-butyrate-CD (HEE-BA-CD) |
| Hydroxybutyl-methoxycarbonyl-CD (HBE-MC-CD) | Hydroxypropyl-methoxycarbonyl-CD (HPE-MC-CD) | Hydroxyethyl-methoxycarbonyl-CD (HEE-MC-CD) |
| Hydroxybutyl-ethoxycarbonyl-CD (HBE-EC-CD) | Hydroxypropyl-ethoxycarbonyl-CD (HPE-EC-CD) | Hydroxyethyl-ethoxycarbonyl-CD (HEE-EC-CD) |
| Hydroxybutyl-propoxycarbonyl-CD (HBE-PC-CD) | Hydroxypropyl-propoxycarbonyl-CD (HPE-PC-CD) | Hydroxyethyl-propoxycarbonyl-CD (HEE-PC-CD) |
| Hydroxybutenyl-ethyl (HBNE-EE-CD) | Hydroxypropenyl-ethyl (HPNE-EE-CD) | Hydroxypentenyl-ethyl (HPTNE-EE-CD) |
| Hydroxybutenyl-methyl (HBNE-ME-CD) | Hydroxypropenyl-methyl (HPNE-ME-CD) | Hydroxypentenyl-methyl (HPTNE-ME-CD) |
| Hydroxybutenyl-propyl (HBNE-PE-CD) | Hydroxypropenyl-propyl (HPNE-PE-CD) | Hydroxypentenyl-propyl (HPTNE-PE-CD) |
| Hydroxybutenyl-butyl (HBNE-BE-CD) | Hydroxypropenyl-butyl (HPNE-BE-CD) | Hydroxypentenyl-butyl (HPTNE-BE-CD) |
| Hydroxybutenyl-carboxymethyl-CD (HBNE-CME-CD) | Hydroxypropenyl-carboxymethyl-CD (HPNE-CME-CD) | Hydroxypentenyl-carboxymethyl-CD (HPTNE-CME-CD) |
| Hydroxybutenyl-carboxyethyl-CD (HBNE-CEE-CD) | Hydroxypropenyl-carboxyethyl-CD (HPNE-CEE-CD) | Hydroxypentenyl-carboxyethyl-CD (HPTNE-CEE-CD) |
| Hydroxybutenyl-acetate-CD (HBNE-AA-CD) | Hydroxypropenyl-acetate-CD (HPNE-AA-CD) | Hydroxypentenyl-acetate-CD (HPTNE-AA-CD) |
| Hydroxybutenyl-propionate-CD (HBNE-PA-CD) | Hydroxypropenyl-propionate-CD (HPNE-PA-CD) | Hydroxypentenyl-propionate-CD (HPTNE-PA-CD) |
| Hydroxybutenyl-butyrate-CD (HBNE-BA-CD) | Hydroxypropenyl-butyrate-CD (HPNE-BA-CD) | Hydroxypentenyl-butyrate-CD (HPTNE-BA-CD) |
| Hydroxybutenyl-methoxycarbonyl-CD (HBNE-MC-CD) | Hydroxypropenyl-methoxycarbonyl-CD (HPNE-MC-CD) | Hydroxypentenyl-methoxycarbonyl-CD (HPTNE-MC-CD) |
| Hydroxybutenyl-ethoxycarbonyl-CD (HBNE-EC-CD) | Hydroxypropenyl-ethoxycarbonyl-CD (HPNE-EC-CD) | Hydroxypentenyl-ethoxycarbonyl-CD (HPTNE-EC-CD) |
| Hydroxybutenyl-propoxycarbonyl-CD (HBNE-PC-CD) | Hydroxypropenyl-propoxycarbonyl-CD (HPNE-PC-CD) | Hydroxypentenyl-propoxycarbonyl-CD (HPTNE-PC-CD) |

After reaction, purification, and/or isolation, the cyclodextrin derivative composition of the present invention can comprise small amounts (e.g., 1% or less, 0.5% or less, 0.1% or less, 0.05% or less, 0.001% or less, 0.0005% or less, or 0.0001% or less, by weight) of a cyclodextrin starting material (e.g., an underivatized parent cyclodextrin).

The cyclodextrin derivative can be present in high purity form. See U.S. Pat. No. 7,635,773. In some embodiments, the cyclodextrin derivative is a high purity SAE-CD composition having a reduced amount of drug-degrading agent as compared to known commercial lots of CAPTISOL®. The composition optionally has a reduced amount of phosphate or excludes phosphate entirely as compared to known commercial lots of CAPTISOL®. The composition also optionally has reduced haze as compared to older commercial lots of CAPTISOL® and lower amounts of drug-degrading agent as compared to known commercial lots of CAPTISOL®. The SAE-CD composition can also have reduced amounts of 1,4-butane sultone and 4-hydroxy-butane-1-sulfonic acid as compared to known commercial lots of CAPTISOL®.

In some embodiments, a process of the present invention is used to prepare a high purity SAE-CD composition comprising:
(a) a sulfoalkyl ether cyclodextrin;
(b) less than 200 ppm, less than 150 ppm, less than 100 ppm, less than 50 ppm, less than 20 ppm, less than 10 ppm, less than 5 ppm, or less than 2 ppm of a phosphate; and
(c) less than 0.5, less than 0.25, less than 0.2, less than 0.15, less than 0.1, or less than 0.05 Absorbance Units ("A.U.") due to a drug-degrading agent as determined by UV/vis spectrophotometry at a wavelength of 245 nm to 270 nm for an aqueous solution containing 300 mg of the SAE-CD composition per mL of solution in a cell having a 1 cm path length.

In some embodiments, the high purity cyclodextrin composition comprises less than 0.5, less than 0.25, less than 0.2, less than 0.15, less than 0.1, or less than 0.05 A.U. due to a color-forming agent as determined by UV/vis spectrophotometry at a wavelength of 320 nm to 350 nm for an aqueous solution containing 500 mg of the SAE-CD composition per mL of solution in a cell having a 1 cm path length.

In some embodiments, the high purity cyclodextrin composition comprises less than 0.5, less than 0.25, less than 0.2, less than 0.15, less than 0.1, or less than 0.05 A.U. due to a drug-degrading agent as determined by UV/vis spectrophotometry at a wavelength of 245 nm to 270 nm for an aqueous solution containing 500 mg of the SAE-CD composition per mL of solution in a cell having a 1 cm path length.

In some embodiments, the high purity cyclodextrin composition comprises less than 1% wt., less than 0.5% wt., less than 0.2% wt., less than 0.1% wt., less than 0.08% wt., or less than 0.05% wt. of an alkali metal halide salt.

In some embodiments, the high purity cyclodextrin composition comprises less than 1% wt., less than 0.5% wt., less than 0.25% wt., less than 0.1% wt., less than 0.08% wt., or less than 0.05% wt. of a hydrolyzed sulfoalkylating agent.

In some embodiments, the high purity cyclodextrin composition comprises less than 500 ppm, less than 100 ppm, less than 50 ppm, less than 20 ppm, less than 10 ppm, less than 5 ppm, less than 2 ppm, less than 1 ppm, less than 500 ppb, or less than 250 ppb of a sulfoalkylating agent.

In some embodiments, the high purity cyclodextrin composition comprises less than 0.5% wt., less than 0.2% wt., less than 0.1% wt., or less than 0.08% wt. of underivatized cyclodextrin.

A cyclodextrin derivative composition of the present invention provides unexpected advantages over other structurally related cyclodextrin derivative compositions. By "structurally related" is meant, for example, that the substituent of the cyclodextrin derivative in the composition is essentially the same as the substituent of other cyclodextrin derivative to which it is being compared. Exemplary advantages can include an enhanced purity, reduced content of pyrogens, reduced content of drug-degrading components, reduced content of color-forming agents, reduced content of unreacted substituent precursor, and/or reduced content of unreacted cyclodextrin starting material.

A water soluble cyclodextrin derivative composition can comprise a SAE-CD compound, or mixture of compounds, of the Formula I:

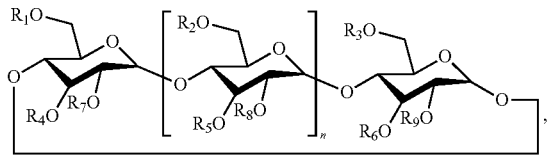

wherein: n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group.

Since SAE-CD is a poly-anionic cyclodextrin, it can be provided in different salt forms. Suitable counterions include cationic organic atoms or molecules and cationic inorganic atoms or molecules. The SAE-CD can include a single type of counterion or a mixture of different counterions. The properties of the SAE-CD can be modified by changing the identity of the counterion present. For example, a first salt form of a SAE-CD composition can possess greater osmotic potential or greater water activity reducing power than a different second salt form of same SAE-CD.

In some embodiments, a sulfoalkyl ether cyclodextrin is complexed with one or more pharmaceutically acceptable cations selected from, e.g., $H^+$, alkali metals (e.g., $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine, ethylenediamine and ($C_4$-$C_8$)-cycloalkanolamine, and the like, and combinations thereof.

Further exemplary SAE-CD derivatives include:

TABLE 5

| $SAE_x$-α-CD | $SAE_x$-β-CD | $SAE_x$-γ-CD |
|---|---|---|
| (Sulfoethyl ether)$_x$-α-CD | (Sulfoethyl ether)$_x$-β-CD | (Sulfoethyl ether)$_x$-γ-CD |
| (Sulfopropyl ether)$_x$-α-CD | (Sulfopropyl ether)$_x$-β-CD | (Sulfopropyl ether)$_x$-γ-CD |
| (Sulfobutyl ether)$_x$-α-CD | (Sulfobutyl ether)-β-CD | (Sulfobutyl ether)$_x$-γ-CD |
| (Sulfopentyl ether)$_x$-α-CD | (Sulfopentyl ether)$_x$-β-CD | (Sulfopentyl ether)$_x$-γ-CD |
| (Sulfohexyl ether)$_x$-α-CD | (Sulfohexyl ether)$_x$-β-CD | (Sulfohexyl ether)$_x$-γ-CD | wherein x denotes the average degree of substitution. In some embodiments, the cyclodextrin derivatives are formed as salts.

Various embodiments of a sulfoalkyl ether cyclodextrin include eicosa-O-(methyl)-6G-O-(4-sulfobutyl)-β-cyclodextrin, heptakis-O-(sulfomethyl)-tetradecakis-O-(3-sulfopropyl)-β-cyclodextrin, heptakis-O-[(1,1-dimethylethyl)dimethylsilyl]-tetradecakis-O-(3-sulfopropyl)-β-cyclodextrin, heptakis-O-(sulfomethyl)-tetradecakis-O-(3-sulfopropyl)-β-cyclodextrin, and heptakis-O-[(1,1-dimethylethyl)dimethylsilyl]-tetradecakis-O-(sulfomethyl)-β-cyclodextrin. Other known ether cyclodextrin derivatives containing a sulfoalkyl moiety include sulfoalkylthio and sulfoalkylthioalkyl ether derivatives such as octakis-(S-sulfopropyl)-octathio-γ-cyclodextrin, octakis-O-[3-[(2-sulfoethyl)thio]propyl]-β-cyclodextrin], and octakis-S-(2-sulfoethyl)-octathio-γ-cyclodextrin.

In some embodiments, a cyclodextrin derivative of the present invention is a sulfoalkyl ether-β-cyclodextrin having an ADS of 4 to 8, 4 to 7.5, 4 to 7, 4 to 6.5, 4.5 to 8, 4.5 to 7.5, 4.5 to 7, 5 to 8, 5 to 7.5, 5 to 7, 5.5 to 8, 5.5 to 7.5, 5.5 to 7, 5.5 to 6.5, 6 to 8, 6 7.5, 6 to 7.1, 6.5 to 7, or 6.5 per cyclodextrin derivative, and the remaining substituents are —H.

In some embodiments, the cyclodextrin derivative is a compound of formula II:

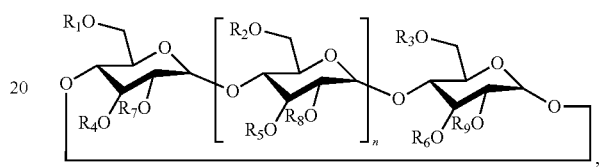

wherein n is 4, 5 or 6, wherein $R_1$, $R_2$, $R_3$, $R_4$, $R_5$, $R_6$, $R_7$, $R_8$ and $R_9$ are independently selected from: —H, a straight-chain or branched $C_1$-$C_8$-(alkylene)-$SO_3$ group, and an optionally substituted straight-chain or branched $C_1$-$C_6$ group.

A water soluble cyclodextrin derivative composition can comprise an AE-cyclodextrin compound, or mixture of compounds, of the Formula III:

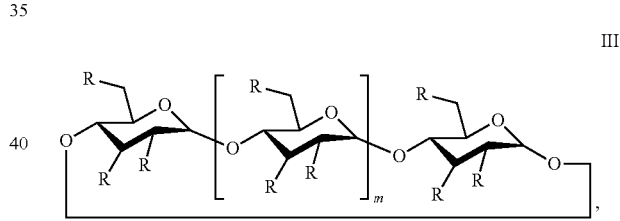

wherein: m is 4, 5 or 6; R is independently selected at each occurrence from the group consisting of —OH and AE; and AE is —O—($C_1$-$C_6$ alkyl); provided that at least one R is —OH; and at least one AE is present.

Further exemplary AE-CD derivatives include:

| (Alkylether)$_y$-α-CD | (Alkylether)$_y$-β-CD | (Alkylether)$_y$-γ-CD |
|---|---|---|
| $ME_y$-α-CD | $ME_y$-β-CD | $ME_y$-γ-CD |
| $EE_y$-α-CD | $EE_y$-β-CD | $EE_y$-γ-CD |
| $PE_y$-α-CD | $PE_y$-β-CD | $PE_y$-γ-CD |
| $BE_y$-α-CD | $BE_y$-β-CD | $BE_y$-γ-CD |
| $PtE_y$-α-CD | $PtE_y$-β-CD | $PtE_y$-γ-CD |
| $HE_y$-α-CD | $HE_y$-β-CD | $HE_y$-γ-CD | wherein ME denotes methyl ether, EE denotes ethyl ether, PE denotes propyl ether, BE denotes butyl ether, PtE denotes pentyl ethyl, HE denotes hexyl ether, and y denotes the average degree of substitution.

A water soluble cyclodextrin derivative composition can comprise a HAE-cyclodextrin compound, or mixture of compounds, of the Formula IV:

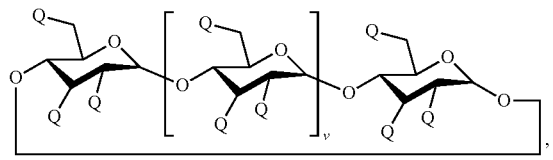

wherein: "v" is 4, 5 or 6; "Q" is independently selected at each occurrence from the group consisting of —OH, and -HAE; and HAE is HO($C_1$-$C_6$ alkyl)-O—, provided that at least one-HAE moiety is present.

Further exemplary Hydroxyalkyl ether-CD derivatives include:
Table 6.

| (HAE)$_z$-α-CD | (HAE)$_z$-β-CD | (HAE)$_z$-γ-CD |
|---|---|---|
| HMEz-α-CD | HMEz-β-CD | HMEz-γ-CD |
| HEEz-α-CD | HEEz-β-CD | HEEz-γ-CD |
| HPEz-α-CD | HPEz-β-CD | HPEz-γ-CD |
| HBEz-α-CD | HBEz-β-CD | HBEz-γ-CD |
| HPtEz-α-CD | HPtEz-β-CD | HPtEz-γ-CD |
| HHEz-α-CD | HHEz-β-CD | HHEz-γ-CD | wherein HME denotes hydroxymethyl ether, HEE denotes hydroxyethyl ether, HPE denotes hydroxypropyl ether, HBE denotes hydroxybutyl ether, HPtE denotes hydroxypentyl ether, HHE denotes hydroxyhexyl ether, and z denotes the average degree of substitution.

A water soluble cyclodextrin derivative composition can comprise a SAE-AE-CD compound, or mixture of compounds, of formula V:

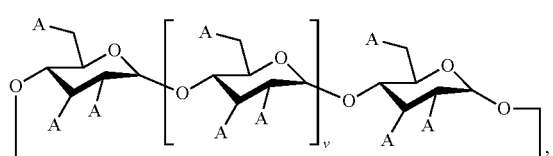

wherein: "v" is 4, 5 or 6; "A" is independently selected at each occurrence from the group consisting of —OH, -SAET and -AE; x is the degree of substitution for the SAET moiety and is 1 to 3v+5; y is the degree of substitution for the AE moiety and is 1 to 3v+5; -SAE is —O—($C_2$-$C_6$ alkylene)-$SO_3^-$; T is independently at each occurrence a cation; and AE is —O($C_1$-$C_3$ alkyl); provided that at least one-SAET moiety and at least one-AE moiety are present; and the sum of x, y and the total number of —OH groups in a cyclodextrin derivative is 3v+6.

Specific embodiments of the derivative of the present invention include those wherein: 1) the alkylene moiety of the SAE has the same number of carbons as the alkyl moiety of the AE; 2) the alkylene moiety of the SAE has a different number of carbons than the alkyl moiety of the AE; 3) the alkyl and alkylene moieties are independently selected from the group consisting of a straight chain or branched moiety; 4) the alkyl and alkylene moieties are independently selected from the group consisting of a saturated or unsaturated moiety; 5) the ADS for the SAE group is greater than or approximates the ADS for the AE group; or 6) the ADS for the SAE group is less than the ADS for the AE group.

A water soluble cyclodextrin derivative composition can comprise a SAE-HAE-CD compound, or mixture of compounds, of formula VI:

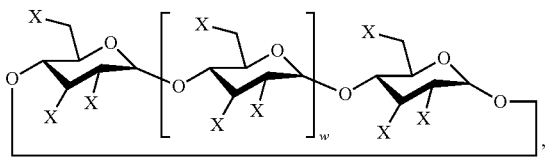

wherein: "w" is 4, 5 or 6; "X" is independently selected at each occurrence from the group consisting of —OH, SAET and HAE; x is the degree of substitution for the SAET moiety and is 1 to 3w+5; y is the degree of substitution for the HAE moiety and is 1 to 3w+5; -SAE is —O—($C_2$-$C_6$ alkylene)-$SO_3^-$; T is independently at each occurrence a cation; and HAE is HO—($C_1$-$C_6$ alkyl)-O—; provided that at least one-SAET moiety and at least one-HAE moiety are present; and the sum of x, y and the total number of —OH groups in a cyclodextrin derivative is 3w+6.

The cyclodextrin derivative can be selected from the group consisting of SAE-CD, HAE-CD, SAE-HAE-CD, HANE-CD, HAE-AE-CD, AE-CD, SAE-AE-CD, neutral cyclodextrin, anionic cyclodextrin, cationic cyclodextrin, halo-derivatized cyclodextrin, amino-derivatized cyclodextrin, nitrile-derivatized cyclodextrin, aldehyde-derivatized cyclodextrin, carboxylate-derivatized cyclodextrin, sulfate-derivatized cyclodextrin, sulfonate-derivatized cyclodextrin, mercapto-derivatized cyclodextrin, alkylamino-derivatized cyclodextrin, and succinyl-derivatized cyclodextrin.

The order of addition, mixing or contact of the components prior to and during passage through the flow-through reactor can have an impact upon the modality of the overall distribution profile of the cyclodextrin derivative composition. Cyclodextrin derivatives having the specified distribution profile modalities can be prepared by employing different orders of addition or mixing of the starting materials.

A cyclodextrin derivative having a monomodal overall distribution profile is prepared according to a process comprising contacting a cyclodextrin starting materials with an optional catalyst (e.g., an alkalinizing agent) to form an alkaline mixture; contacting portions of the alkaline mixture with portions of a substituent precursor to form a feedstock; and continuously or semi-continuously flowing portions of the feedstock through a reactor to form a raw product comprising a cyclodextrin derivative having a monomodal distribution profile. Alternatively, a cyclodextrin derivative having a bimodal or otherwise multimodal overall distribution profile is prepared according to a process comprising contacting a cyclodextrin starting material with a substituent precursor to form a feedstock; contacting portions of the feedstock with an optional catalyst (e.g., an alkalinizing agent) to form a second feedstock; and continuously or semi-continuously flowing portions of the second feedstock into a reactor to form a raw product comprising a cyclodextrin derivative having a bimodal distribution profile. The pH of the feedstock, the residence time, the reactor temperature, the pressure, the molar ratio of the substituent precursor to the cyclodextrin starting, the molar ratio of the optional catalyst to the cyclodextrin starting material molar ratio, and the yield of cyclodextrin derivative in the raw product are as defined herein.

Within a given cyclodextrin derivative composition, the substituents of the cyclodextrin derivative(s) thereof can be the same or different. For example, SAE moieties can have the same type or different type of alkylene (alkyl) radical upon each occurrence in a cyclodextrin derivative composition. In such an embodiment, the alkylene radical in the SAE moiety can be ethyl, propyl, butyl, pentyl or hexyl in each occurrence in a cyclodextrin derivative composition.

The cyclodextrin derivatives can differ in their degree of substitution by functional groups, the number of carbons in the functional groups, their molecular weight, the number of glucopyranose units contained in the base cyclodextrin used to form the derivatized cyclodextrin and or their substitution patterns. In addition, the derivatization of a cyclodextrin with functional groups occurs in a controlled, although not exact manner. For this reason, the degree of substitution is actually a number representing the average number of functional groups per cyclodextrin (for example, $SBE_7$-β-CD, has an average of 7 substitutions per cyclodextrin). Thus, it has an average degree of substitution ("ADS") of 7. In addition, the regiochemistry of substitution of the hydroxyl groups of the cyclodextrin is variable with regard to the substitution of specific hydroxyl groups of the hexose ring. For this reason, substitution of the different hydroxyl groups is likely to occur during manufacture of the derivatized cyclodextrin, and a particular derivatized cyclodextrin will possess a preferential, although not exclusive or specific, substitution pattern. Given the above, the molecular weight of a particular derivatized cyclodextrin composition can vary from batch to batch.

In a single parent cyclodextrin molecule, there are 3v+6 hydroxyl moieties available for derivatization. Where v=4 (α-cyclodextrin), "y" the degree of substitution for the moiety can range in value from 1 to 18. Where v=5 (j-cyclodextrin), "y" the degree of substitution for the moiety can range in value from 1 to 21. Where v=6 (γ-cyclodextrin), "y" the degree of substitution for the moiety can range in value from 1 to 24. In general, "y" also ranges in value from 1 to 3v+g, where g ranges in value from 0 to 5. In some embodiments, "y" ranges from 1 to 2v+g, or from 1 to 1v+g.

The degree of substitution ("DS") for a specific moiety (SAE, HAE or AE, for example) is a measure of the number of SAE (HAE or AE) substituents attached to an individual cyclodextrin molecule, in other words, the moles of substituent per mole of cyclodextrin. Therefore, each substituent has its own DS for an individual cyclodextrin derivative species. The average degree of substitution ("ADS") for a substituent is a measure of the total number of substituents present per cyclodextrin molecule for the distribution of cyclodextrin derivatives within a cyclodextrin derivative composition of the present invention. Therefore, $SAE_4$-CD has an ADS (per CD molecule) of 4.

Some embodiments of the present invention include those wherein: 1) more than half of the hydroxyl moieties of the cyclodextrin derivative are derivatized; 2) half or less than half of the hydroxyl moieties of the cyclodextrin derivative are derivatized; 3) the substituents of the cyclodextrin derivative are the same upon each occurrence; 4) the substituents of the cyclodextrin derivative comprise at least two different substituents; or 5) the substituents of the cyclodextrin derivative comprise one or more substituents selected from the group consisting of unsubstituted alkyl, substituted alkyl, halide (halo), haloalkyl, amine (amino), aminoalkyl, aldehyde, carbonylalkyl, nitrile, cyanoalkyl, sulfoalkyl, hydroxyalkyl, carboxyalkyl, thioalkyl, unsubstituted alkylene, substituted alkylene, aryl, arylalkyl, heteroaryl, and heteroarylalkyl.

Cyclodextrin derivative compositions can comprise plural individual cyclodextrin derivative species differing in individual degree of substitution, such that the average degree of substitution is calculated, as described herein, from the individual degrees of substitution of the species. More specifically, a SAE-CD derivative composition can comprise plural SAE-CD species each having a specific individual degree of substitution with regard to the SAE substituent. As a consequence, the ADS for SAE of a SAE-CD derivative composition represents an average of the IDS values of the population of individual molecules in the composition. For example, a $SAE_{5.2}$-CD composition comprises a distribution of plural $SAE_x$-CD molecules, wherein x (the DS for SAE groups) can range from 1 to 10-11 for individual cyclodextrin molecules; however, the population of SAE-cyclodextrin molecules is such that the average value for x (the ADS for SAE groups) is 5.2.

A cyclodextrin derivative composition comprises a distribution of plural individual cyclodextrin derivative species, each species having an individual degree of substitution ("IDS"). The content of each of the cyclodextrin species in a particular composition can be quantified using capillary electrophoresis (see Example 24). The method of analysis (capillary electrophoresis, for example, for charged cyclodextrin derivatives) is sufficiently sensitive to distinguish between compositions having only 5% of one cyclodextrin derivative and 95% of another cyclodextrin derivative from starting cyclodextrin derivative compositions containing.

The moisture content of cyclodextrin derivatives can be determined using a Brinkman Karl-Fischer Coulometer (Brinkman Instruments Co., IL). A known weight of a solid cyclodextrin is added to the Karl-Fischer Coulometer and the total amount of water in the sample is read-out. The total amount of water present in the sample is converted to a percentage of the solid, thus giving the percent moisture content of the sample.

Mixtures of SBE-β-CD and SBE-γ-CD derivatives were analyzed by capillary electrophoresis using a Beckman P/ACE 2210 capillary electrophoresis system coupled with a UV absorbance detector (Beckman Instruments, Inc., Fullereton, Calif.). Separation of the SBE-β-CD and SBE-γ-CD derivatives was performed at 25° C. using a fused silica capillary (50 μm inner diameter, 57 cm total length, and 50 cm effective length) with a pH adjusted running buffer (30 mM benzoic acid and 100 mM tris-hydroxymethyl-aminomethanol). The capillary was treated with injections of water, 0.01 N NaOH, and running buffer prior to each separation. The detection wavelength was 214 nm. The voltage was 30 kV. Samples were introduced by pressure injections: 20 s at 0.5 psi. The derivatized cyclodextrin mixtures were agitated until material was dissolved then were filtered using a 0.2 m filter prior to separating.

The substitution patterns of cyclodextrin derivatives prepared by a process of the present invention can be determined using, inter alia, $^1$H-NMR, $^{13}$C-NMR, COSY-NMR and/or HMQC. Representative methods for determining the substitution patterns of cyclodextrin derivatives are also provided in WO 2005/042584, the relevant portions of which are hereby incorporated by reference.

Figure 3:
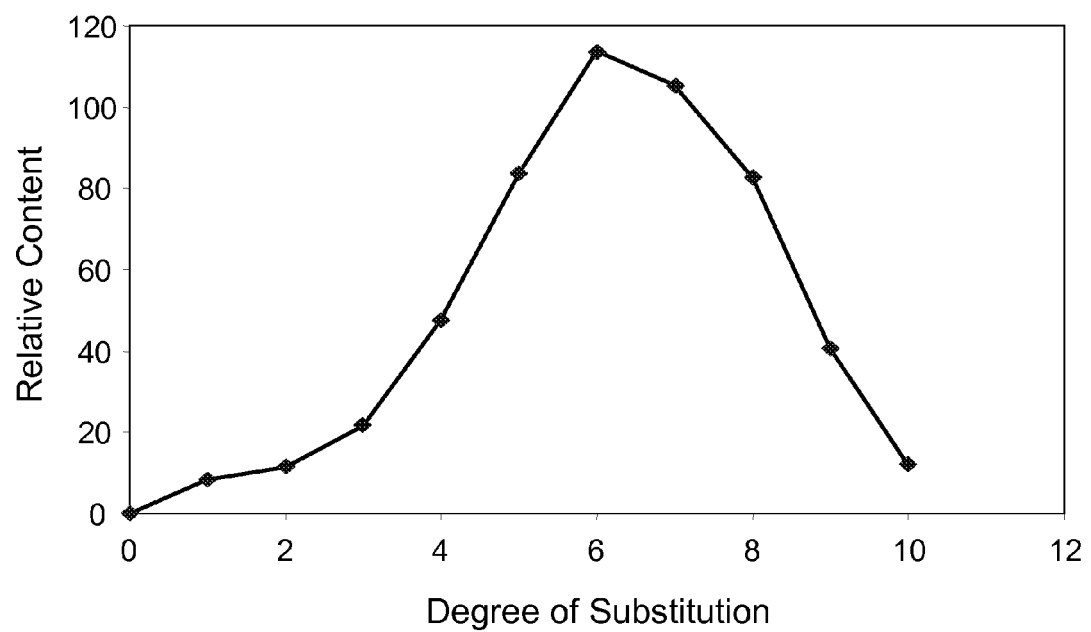
FIGS. 3 and 4 provide graphic representations of distribution profiles for cyclodextrin derivatives prepared according to processes of the present invention.
Figure 4:
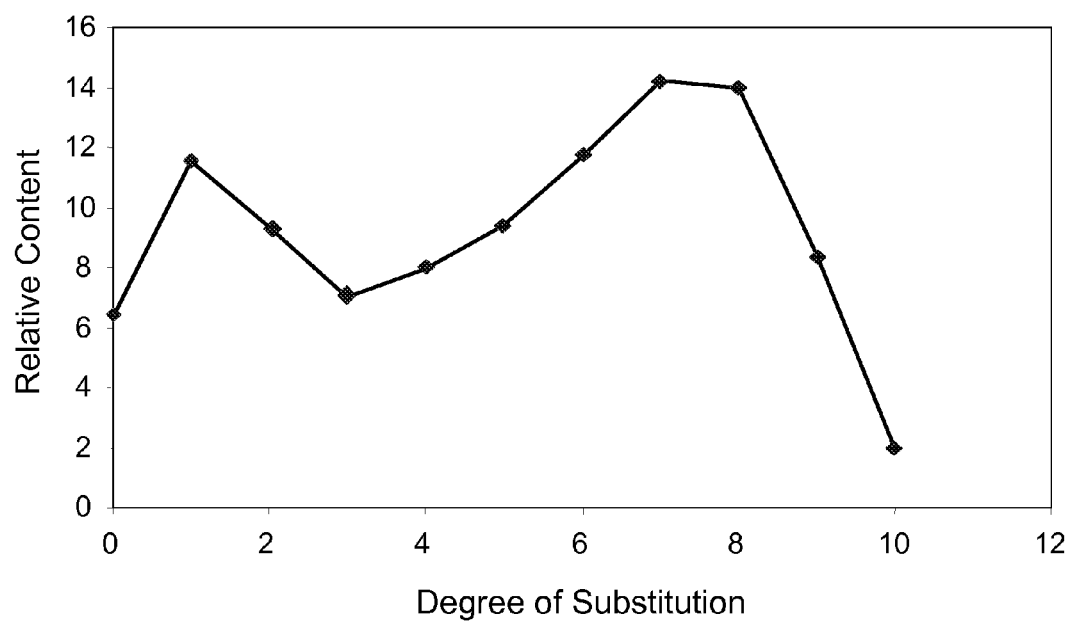

FIG. 2 depicts an electropherogram for a sample of sulfoalkyl ether cyclodextrin prepared according to a process of the present inventions. The SAE-CD comprises a distribution of individual sulfobutyl ether cyclodextrin derivative species. The peak number (Pk #) in the electropherogram corresponds to the IDS for each species included in the distribution. The electropherogram data is plotted as peak number (of each individual species) versus area (for each individual species), wherein the area represents the approximate relative content of each individual species within a distribution. The plotted data is essentially an overall "distribution profile," which can be based upon normalized area percent or area percent data, for the cyclodextrin derivative composition. The modality of the overall distribution profile is determined by counting the number of apexes in area percent between which there is a minimum in the area percent. The line is then determined to be monomodal, bimodal, or multi-modal. A monomodal distribution profile (FIG. 3) exhibits a single maximum over the entire distribution profile as determined graphically and/or numerically. A bimodal distribution profile (FIG. 4) exhibits two maxima over the entire distribution profile as determined graphically and/or numerically. A trimodal distribution profile exhibits three maxima over the entire distribution profile as determined graphically and/or numerically.

The above-mentioned variations among the individual species of cyclodextrin derivatives in a distribution can lead to changes in the complexation equilibrium constant $K_{1:1}$ which in turn will affect the required molar ratios of the derivatized cyclodextrin to active agent. The equilibrium constant is also somewhat variable with temperature and allowances in the ratio are required such that the agent remains solubilized during the temperature fluctuations that can occur during manufacture, storage, transport, and use. The equilibrium constant can also vary with pH and allowances in the ratio can be required such that the agent remains solubilized during pH fluctuations that can occur during manufacture, storage, transport, and use. The equilibrium constant can also vary due the presence of other excipients (e.g., buffers, preservatives, antioxidants). Accordingly, the ratio of derivatized cyclodextrin to active agent can be varied from the ratios set forth herein in order to compensate for the above-mentioned variables.

The cyclodextrin derivatives made according to a process of the present invention can be employed in compositions, formulations, methods and systems as such those disclosed in U.S. Pat. Nos. 5,134,127, 5,376,645, 5,914,122, 5,874,418, 6,046,177, 6,133,248, 6,153,746, 6,407,079, 6,869,939, 7,034,013, 7,625,878, 7,629,331, and 7,635,773; U.S. Pub. Nos. 2005/0164986, 2005/0186267, 2005/0250738, 2006/0258537, 2007/0020196, 2007/0020298, 2007/0020299, 2007/0175472, 2007/0202054, 2008/0194519, 2009/0011037, 2009/0012042, 2009/0123540; U.S. application Ser. Nos. 12/404,174, 12/407,734, 61/050,918, 61/177,718, and 61/182,560; and PCT International Application Nos. PCT/US06/62346, PCT/US07/71758, PCT/US07/71748, PCT/US07/72387, PCT/US07/72442, PCT/US07/78465, PCT/US08/61697, PCT/US08/61698, PCT/US08/70969, and PCT/US08/82730, the entire disclosures of which are hereby incorporated by reference. The cyclodextrin derivatives prepared according to the processes herein can also be used as suitable substitutes for other known grades of cyclodextrin derivatives possessing the same functional groups.

The cyclodextrin derivatives made according to a process of the present invention can be processed by fluidized bed spray agglomeration to yield agglomerated particles. See U.S. Pat. No. 7,629,331. Such particles can be associated with improved physical properties such as improved aqueous dissolution rate, compression crushing strength, ease of tabletting, and/or improved solids handling.

In some embodiments, a process of the present invention is used to prepare a SAE-CD composition comprising:
(a) a sulfoalkyl ether cyclodextrin;
(b) no more than 20% by weight moisture;
(c) a bulk density of 0.38 g/cm$^3$ to 0.66 g/cm$^3$;
(d) a tapped density of 0.49 g/cm$^3$ to 0.75 g/cm$^3$, wherein the tapped density of the sulfoalkyl ether cyclodextrin composition is higher than the bulk density; and
(e) a gravitational-flow minimum orifice diameter of 3 mm to 12 mm; and wherein the sulfoalkyl ether cyclodextrin composition comprises agglomerated particles, In some embodiments, the SAE-CD composition comprising agglomerated particles is produced by a process comprising:
(a) forming a fluidized bed of SAE-CD particles in a drying chamber of a fluidized bed spray dryer apparatus with an attached 3-chamber fluidization bed;
(b) recycling fine particles from the fluidized bed back into the drying chamber at a location adjacent to a liquid feed atomizer, and
(c) collecting agglomerated particles from the third chamber of the 3-chamber fluidization bed.

In some embodiments, the SAE-CD composition comprising agglomerated particles comprises a bulk density of 0.55 g/cm$^3$ to 0.66 g/cm$^3$ and a tapped density of 0.66 g/cm to 0.75 g/cm$^3$.

In some embodiments, the SAE-CD composition comprising agglomerated particles comprises a bulk density of 0.38 g/cm$^3$ to 0.55 g/cm$^3$ and a tapped density of 0.49 g/cm$^3$ to 0.66 g/cm$^3$.

In some embodiments, the SAE-CD composition comprising agglomerated particles comprises: a gravitational-flow minimum orifice diameter of 10 mm or less; a true density of 1.1 g/cm$^3$ to 1.5 g/cm$^3$; a CARR's index of 12% to 24%; a mean particle diameter of 75 microns to 200 microns; or a combination thereof. In some embodiments, at least 90% of the particle volume comprises particles having calculated diameters greater than or equal to 25 microns. In some embodiments, 5 g of the sulfoalkyl ether cyclodextrin composition comprising agglomerated particles has an average dissolution time of 2 min to 4.5 min when placed in water.

In some embodiments, the SAE-CD composition comprising agglomerated particles comprises a moisture content of 2% to 3% by weight and a compression crushing strength of 1.0 kP to 20 kP when compressed into a tablet using a Pmax of 30 MPa to 275 MPa.

In some embodiments, the SAE-CD composition comprising agglomerated particles comprises a moisture content of 5% to 6% by weight and a compression crushing strength of 0.5 to 11 kP when compressed into a tablet using a Pmax of 15 MPa to 70 MPa.

The cyclodextrin derivative composition can be used to prepare a combination composition comprising two different cyclodextrin derivative compositions. Some embodiments of the present invention provide a combination composition comprising a mixture of at least two different cyclodextrin derivative compositions, wherein at least one of the cyclodextrin derivative compositions has been made according to a process of the present invention. In some embodiments, a combination composition can comprise: a) a first cyclodextrin derivative composition having a first average degree of substitution for a specified substituent; and b) a second cyclodextrin derivative composition having a second average degree of substitution for the specified substituent. Each of the first and second cyclodextrin derivative compositions can comprise plural cyclodextrin derivative species differing in the individual degree of substitution ("IDS") for the specified substituent. The mixture comprises: a) a first cyclodextrin derivative composition having a first average degree of substitution in the range of 1 to 10, or 1 to 6; and b) an added second cyclodextrin derivative composition having a second average degree of substitution in the range of 3 to 12, or 5 to 12, wherein the first and second average degrees of substitution differ by at least 1, at least 2, at least 3, at least 4, at least 5, at least 6, or at least 7, and the second average degree of substitution is higher than the first average degree of substitution. In some embodiments, the mixture comprises: a) a first cyclodextrin derivative composition comprising plural cyclodextrin derivative species, the composition having a first average degree of substitution in the range of 1 to 12; and b) an added second cyclodextrin derivative composition consisting essentially of a cyclodextrin derivative species having an IDS of 1 to 12, wherein the first average degree of substitution differs from the individual degree of substitution by at least 2. The IDS of the added cyclodextrin derivative species can be higher or lower than the ADS of the first cyclodextrin derivative composition. The molar ratio of add cyclodextrin derivative species to first cyclodextrin derivative composition can range from 95:5 to 5:95.

In some embodiments, the combination composition comprises a mixture of at least two different sulfoalkyl ether cyclodextrins derivative compositions each SAE-CD derivative composition having its own average degree of substitution, or of at least two different hydroxyalkyl ether cyclodextrins derivative compositions each HAE-CD derivative composition having its own average degree of substitution. In some embodiments, the average degree of substitution of the first composition differs from the average degree of substitution of the second composition by at least 2, 3, 4, 5, 6, 7, 8 or more. In each case, at least one of the cyclodextrin derivative compositions has been made according to a process of the present invention.

In a combination composition, the first cyclodextrin derivative composition can be present in less than stoichiometric, stoichiometric or greater than stoichiometric amounts with respect to the amount of second cyclodextrin derivative composition present in the combination composition. The combination composition can comprise at least 5%, at least 10%, at least 25%, at least 50%, at least 75%, at least 90%, or at least 95% of the first cyclodextrin derivative composition. Alternatively, the combination composition can comprise at least 5%, at least 10%, at least 25%, at least 50%, at least 75%, at least 90%, or at least 95% of the second cyclodextrin derivative composition. The percentages of each derivative can be on a weight or molar basis. The mole ratio or weight ratio of the first cyclodextrin derivative composition to second cyclodextrin derivative composition ranges from 95:5 to 5:95, from 90:10 to 10:90, from 75:25 to 25:75 (3:1 to 1:3), from 67:33.3 to 33.3:67 (2:1 to 1:2), or approximates 50:50 (1:1).

A combination composition can be prepared by: a) providing a first cyclodextrin derivative composition having a first average degree of substitution and comprising plural cyclodextrin derivatives species differing in individual degree of substitution; b) providing a second cyclodextrin derivative composition having a second average degree of substitution and comprising plural cyclodextrin derivatives species differing in individual degree of substitution, wherein the second average degree of substitution is higher than the first average degree of substitution by at least one; and c) combining the first cyclodextrin derivative composition with the second cyclodextrin derivative composition, thereby forming the combination composition.

A combination composition can also be prepared by: exposing an initial cyclodextrin comprising at least one underivatized hydroxyl moiety, in aqueous alkaline media, to a substituent precursor for a period of time sufficient, at a temperature sufficient and at a solution pH sufficient to permit formation of a raw product comprising a cyclodextrin derivative composition having bimodal, trimodal or multi-modal substitution profile, and optionally processing to remove undesired components thereby forming the combination composition. The initial cyclodextrin can be an underivatized parent cyclodextrin or a previously prepared cyclodextrin derivative.

As a result of the mixing of a first and second cyclodextrin derivative compositions, the combination composition exhibits one, two, or more maxima in its substitution profile. Accordingly, another aspect of the present invention provides a combination composition comprising plural cyclodextrin derivative species differing in individual degree of substitution such that the combination composition exhibits at least two maxima in individual degree of substitution in a plot of individual degree of substitution vs. content of cyclodextrin derivative species (the substitution profile). The combination composition can have a monomodal, bimodal, trimodal, or multi-modal substitution profile, wherein the maxima differ by at least one, at least two, at least three, at least four, at least five, at least six, at least seven, or at least eight units.

The ADS for a cyclodextrin derivative composition is calculated based upon the IDS according to the following formulas:

$$CA = PAC \times MT;$$

$$IDS = (CA/SCA) \times 100; \text{ and}$$

$$ADS = \text{Summation}(IDS \times \text{peak number})/100;$$

wherein CA refers to the "Corrected Area," PAC refers to the "Peak Area Count;" MT refers to the "Migration Time;" IDS refers to the "Individual Degree of Substitution;" SCA refers to the "Summation of Corrected Area;" and ADS refers to the "Average Degree of Substitution." These values can be obtained using CE.

A combination composition, however, has an apparent ADS ("AP-ADS") that can be calculated for a monomodal, bimodal, trimodal, or multi-modal distribution profile. The AP-ADS is calculated as follows:

For bimodal distribution:

$$AP\text{-}ADS = (ADS_1 * MP_1) + (ADS_2 * MP_2)$$

For trimodal distribution:

$$AP\text{-}ADS = (ADS_1 * MP_1) + (ADS_2 * MP_2) + (ADS_3 * MP_3)$$

In the above equations, wherein MP denotes "mole percent" and 1, 2, and 3 denote the identity of the DS peak to which the MP corresponds. For example, a combination composition having a bimodal distribution profile and comprising a 25:75 molar ratio of a 1st SAE-CD composition with an ADS of 3 and a 2nd SAE-CD composition with an ADS of 8 would be calculated as follows.

$$AP\text{-}ADS = (3*0.25) + (8*0.75) = 6.75$$

A combination composition of the present invention can have an apparent average degree of substitution (AP-ADS) in the range of 1 to 12, 2 to 11, 2 to 10, 3 to 9, or 2 to 8.

Cyclodextrin derivative compositions (distributions) varying in ADS can be made as described herein.

The cyclodextrin derivative compositions can have a high to moderate to low ADS.

The cyclodextrin derivative compositions can also have a wide or narrow "span," which is the number of individual DS species within a cyclodextrin derivative composition. For example, a cyclodextrin derivative composition comprising a single species of cyclodextrin derivative having a single specified individual DS is said to have a span of one, and the individual DS of the cyclodextrin derivative equals the ADS of its cyclodextrin derivative composition. An electropherogram, for example, of a cyclodextrin derivative with a span of one should have only one cyclodextrin derivative species with respect to DS. A cyclodextrin derivative composition having a span of two comprises two individual cyclodextrin derivative species differing in their individual DS, and its electropherogram, for example, would indicate two different cyclodextrin derivative species differing in DS. Likewise, the span of a cyclodextrin derivative composition having a span of three comprises three individual cyclodextrin derivative species differing in their individual DS. The span of a cyclodextrin derivative composition typically ranges from 5 to 15, or 7 to 12, or 8 to 11.

A parent cyclodextrin includes a secondary hydroxyl group on the C-2 and C-3 positions of the glucopyranose residues forming the cyclodextrin and a primary hydroxyl on the C-6 position of the same. Each of these hydroxyl moieties is available for derivatization by substituent precursor. Depending upon the synthetic methodology employed, the substituent moieties can be distributed randomly or in a somewhat ordered manner among the available hydroxyl positions. The regioisomerism of derivatization by the substituent can also be varied as desired. The regioisomerism of each composition is independently selected. For example, a majority of the substituents present can be located at a primary hydroxyl group or at one or both of the secondary hydroxyl groups of the parent cyclodextrin. In some embodiments, the primary distribution of substituents is C-3>C-2>C-6, while in other embodiments the primary distribution of substituents is C-2>C-3>C-6. Some embodiments of the present invention include a cyclodextrin derivative molecule wherein a minority of the substituent moieties is located at the C-6 position, and a majority of the substituent moieties is located at the C-2 and/or C-3 position. Still other embodiments of the present invention include a cyclodextrin derivative molecule wherein the substituent moieties are substantially evenly distributed among the C-2, C-3, and C-6 positions.

Among other uses, a cyclodextrin derivative of the present invention can be used to solubilize and/or stabilize a wide range of different materials and to prepare formulations for particular applications. Cyclodextrin derivatives of the present invention can solubilize and/or stabilize compounds against chemical, thermochemical, hydrolytic, and/or photochemical degradation.

In some embodiments, a cyclodextrin derivative composition made according to the present invention is used to prepare a pharmaceutical composition comprising one or more active agents. As used herein, an "active agent" refers to a physiologically or pharmacologically active substance that produce a systemic or localized effect or effects on animals (e.g., mammals) and/or human beings. Active agents also include pesticides, herbicides, insecticides, antioxidants, plant growth instigators, sterilization agents, catalysts, chemical reagents, food products, nutrients, cosmetics, vitamins, minerals, dietary supplements, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleaning, confectionery, and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

In some embodiments, an active agent, or a majority thereof, is complexed with the cyclodextrin derivative. In other embodiments, the active agent, or a majority thereof, is not complexed with the cyclodextrin derivative. By "complexed" is meant "being part of a clathrate or inclusion complex with," i.e., a complexed therapeutic agent is part of a clathrate or inclusion complex with a cyclodextrin derivative. By "major portion" is meant greater than 50% by weight or greater than 50% on a molar basis. Thus, a formulation according to the present invention can contain an active agent of which more than 50% by weight is complexed with a cyclodextrin. The actual percent of active agent that is complexed will vary according to the complexation equilibrium binding constant characterizing the complexation of a specific cyclodextrin with a specific active agent. The invention also includes embodiments wherein the active agent is not complexed with the cyclodextrin or wherein a minor portion of the active agent is complexed with the derivatized cyclodextrin. It should be noted that a SAE-CD, or any other anionic derivatized cyclodextrin, can form one or more ionic bonds with a positively charged compound. This ionic association can occur regardless of whether the positively charged compound is complexed with the cyclodextrin by inclusion complexation.

An active agent present can be present in an effective amount. By the term "effective amount" is meant the amount or quantity of active agent that is sufficient to elicit the required or desired clinical response, or in other words, the amount that is sufficient to elicit an appreciable biological response when administered to a subject.

The active agent included in the present invention can possess a wide range of values for water solubility, bioavailability, and hydrophilicity. Active agents to which the present invention is particularly suitable include water insoluble, poorly water soluble, slightly water soluble, moderately water soluble, water soluble, very water soluble, hydrophobic, or hydrophilic therapeutic agents. It will be understood by the artisan of ordinary skill that an active agent used in the formulation of the present invention is independently selected at each occurrence from any known active agent and from those disclosed herein. It is not necessary that the active agent complex with the derivatized cyclodextrin or form an ionic association with the derivatized cyclodextrin.

Representative pharmaceutically effective active agents include nutrients and nutritional agents, hematological agents, endocrine and metabolic agents, cardiovascular agents, renal and genitourinary agents, respiratory agents, central nervous system agents, gastrointestinal agents, antiinfective agents, biologic and immunological agents, dermatological agents, ophthalmic agents, antineoplastic agents, diagnostic agents, other agents known in the pharmaceutical arts, and combinations thereof. The above-mentioned list should not be considered exhaustive and is merely exemplary of the many embodiments considered within the scope of the present invention.

In some embodiments, a composition comprises two or more different active agents in combination with a cyclodextrin derivative of the present invention. Representative combinations of active agents include a first drug from a first therapeutic class and a second drug from the same or a different therapeutic class, or a first drug having a first type of biological activity and a second drug having about the same or a different biological activity.

In some embodiments, a composition further comprises a pharmaceutically acceptable excipient. As used herein, "pharmaceutically acceptable" refers to those excipients, compounds, materials, and/or compositions which are, within the scope of sound medical judgment, suitable for contact with the tissues of human beings and animals without excessive toxicity, irritation, allergic response, or other possible complications commensurate with a reasonable benefit/risk ratio. As used herein, the term "excipient" refers to any inert substance that can be combined with the cyclodextrin derivative for preparing the pharmaceutical compositions.

Pharmaceutically acceptable excipients suitable for use with the present invention include, but are not limited to, a carrier, a preservative, an antioxidant, an acidifying agent, an alkalinizing agent, a buffering agent, a bulking agent, a complexation enhancing agent, a cryoprotectant, a density modifier, an electrolyte, a flavor, a fragrance, a lyophilizing aid (e.g., a bulking agent and/or stabilizing agent), a plasticizer, a solubility-enhancing agent, a stabilizing agent, a sweetener, a surface tension modifier, a volatility modifier, a viscosity modifier, an antifoaming agent, a colorant, a complexation-enhancing agent, glucose, an emulsifying agent, an oil, a plasticizer, a tonicity modifier, a flavor, an adsorbents, an antiadherent, a binder, a diluent, a direct compression excipient, a disintegrant, a glidant, a lubricant, an opaquant, a polishing agent, a complexing agents, and other excipients known by those of ordinary skill in the art for use in formulations, and a combination thereof. In addition, one of skill in the art will recognize that pharmaceutically acceptable excipients can be used in the present invention including those listed in *The Handbook of Pharmaceutical Excipients,* 5th Ed., The Pharmaceutical Press and American Pharmacists Association, London, UK and Washington, D.C. (2006), which is incorporated herein by reference in its entirety.

A cyclodextrin derivative composition can further comprise one or more hydrophilic polymers. Hydrophilic polymers can be used as complexation-enhancing, solubility-enhancing and/or water activity reducing agents to improve the performance of formulations containing a cyclodextrin-based preservative. Loftsson has disclosed a number of polymers suitable for combined use with a cyclodextrin (underivatized or derivatized) to enhance the performance and/or properties of the cyclodextrin. Exemplary suitable polymers are disclosed in, e.g., *Pharmazie* 56:746 (2001); *Int. J. Pharm.* 212:29 (2001); *Cyclodextrin: From Basic Research to Market,* U.S. Pat. No. 5,472,954, U.S. Pat. No. 5,324,718, EP 0579435, WO 99/42111; *Pharmazie* 53:733 (1998); *Pharm. Technol. Eur.* 9:26 (1997); *J. Pharm. Sci.* 85:1017 (1996); Proc. of the 8th Int. Symp. on Cyclodextrins, Budapest, HU, Mar. 31-Apr. 2, (1996), 373-376 (J. Szejtli et al., eds, Kluwer Academic Publishers, Dordrecht, Neth.); Proc. of the 9th Int. Symp. on Cyclodextrins, Santiago de Comostela, ES, May 31-Jun. 3, 1998 (1999), 261-264 (J. J. Labandeira et al., eds., Kluwer Academic Publishers, Dordrecht, Neth); Proc. of the 10th Int. Cyclodextrin Symp, Ann Arbor, Mich., May 21-24 (2000), 10-15 (Wacker Biochem Corp.: Adrian, Mich.); *S.T.P. Pharma Sciences* 9:237 (1999); *ACS Symposium Series* 737 (Polysaccharide Applications):24-45 (1999); *Pharma. Res.* 15:1696 (1998); *Drug Dev. Ind. Pharm.* 24:365 (1998); *Int. J. Pharm.* 163:115 (1998); Book of Abstracts, 216th ACS National Meeting, Boston, Aug. 23-27 (1998), CELL-016, American Chemical Society; *J. Controlled Release* 44:95 (1997); *Pharm. Res.* 14:S203 (1996); *Inv. Ophthalmology & Vis. Sci.* 37:1199 (1996); Proc. of the Int. Symposium on Controlled Release of Bioactive Materials (1996), 23rd, 453-454; *Drug Dev. and Ind. Pharm.* 22:401 (1996); *Pharma. Sci.* 2(6):277 (1996); *Eur. J. Pharm. Sci.* 4:S144 (1996); Third European Congress of Pharmaceutical Sciences Edinburgh, Scotland, UK Sep. 15-17, (1996), *Pharmazie* 51:39 (1996); *Eur. J. Pharm. Sci.* 4:S143 (1996); *Int. J. Pharm.* 126:73 (1995); Abstracts of Papers of the American Chemical Society, (2 Apr. 1995) 209(1), 33-CELL; *Eur. J. Pharm. Sci.* 2:297 (1994); *Pharma. Res.* 11:S225 (1994); *Int. J. Pharm.* 104:181 (1994); and *Int. J. Pharm.* 110:169 (1994), the entire disclosures of which are hereby incorporated by reference.

Other suitable polymers are well-known excipients commonly used in the field of pharmaceutical formulations and are included in, for example, *Remington's Pharmaceutical Sciences,* 18th ed., pp. 291-294 (1990), A. R. Gennaro, ed., Mack Publishing Co., Easton, Pa., A. Martin et al., *Physical Pharmacy. Physical Chemical Principles in Pharmaceutical Sciences,* pp. 592-638, 3rd ed., Lea & Febinger, Philadelphia, Pa. (1983), A. T. Florence et al., *Physicochemical Principles of Pharmacy,* pp. 281-334, 2nd ed., MacMillan Press, London (1988). The entire disclosures of the references cited herein are hereby incorporated by reference.

Still other suitable polymers include water-soluble natural polymers, water-soluble semi-synthetic polymers (such as the water-soluble derivatives of cellulose), and water-soluble synthetic polymers. The natural polymers include polysaccharides such as inulin, pectin, algin derivatives (e.g., sodium alginate), and agar, as well as polypeptides such as casein and gelatin. The semi-synthetic polymers include cellulose derivatives such as methylcellulose, hydroxyethylcellulose, hydroxypropyl cellulose, their mixed ethers such as hydroxypropyl methylcellulose, and other mixed ethers such as hydroxyethyl ethylcellulose, hydroxypropyl ethylcellulose, hydroxypropyl methylcellulose phthalate, and carboxymethylcellulose and its salts (e.g., sodium carboxymethylcellulose). The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g., carbomer). Other natural, semi-synthetic, and synthetic polymers not named here which meet the criteria of water solubility, pharmaceutical acceptability and pharmacological inactivity are likewise considered to be within the ambit of the present invention.

As used herein, the term "emulsifier" or "emulsifying agent" is intended to mean a compound added to one or more of the phase components of an emulsion for the purpose of stabilizing the droplets of the internal phase within the external phase. Such compounds include, by way of example and without limitation, lecithin, polyoxyethylene-polyoxypropylene ethers, polyoxyethylene-sorbitan monolaurate, polysorbates, sorbitan esters, stearyl alcohol, tyloxapol, tragacanth, xanthan gum, acacia, agar, alginic acid, sodium alginate, bentonite, carbomer, carboxymethyl cellulose sodium, cholesterol, gelatin, hydroxyethyl cellulose, hydroxypropyl cellulose, octoxynol, oleyl alcohol, polyvinyl alcohol, povidone, propylene glycol monostearate, sodium lauryl sulfate, and others known to those of ordinary skill in the art.

A solubility-enhancing agent can be added to the composition of the present invention. A solubility-enhancing agent is a compound, or compounds, that enhance(s) the solubility of a compound in a liquid formulation. When such an agent is present, the ratio of cyclodextrin/active agent can be changed. Suitable solubility enhancing agents include one or more organic liquids, detergents, soaps, surfactants, and other organic compounds typically used in parenteral formulations to enhance the solubility of a particular agent.

Process Equipment

A "flow-through reactor" refers to a reactor in which one or more streams of reactants are flowed into, reacted therein, and flowed out of in a continuous manner. A flow-through reactor differs from a batch and/or tank reactor in which reactants are flowed into, held for a period of time with optional agitation and/or circulation, and flowed out from. In some embodiments, a reactant is continuously or semi-continuously added to a flow-through reactor, and passed through the reactor (optionally, with heating or cooling) to form a raw product that is continuously or semi-continuously collected or transported from the reactor. Flow-through reactors suitable for use with the present invention include, but are not limited to, a heat exchanger (parallel flow, countercurrent flow, or cross-flow), a serial tube reactor (see, e.g., U.S. Pat. No. 4,597,946), a parallel tube reactor (see, e.g., Hughes et al., Comb. Chem. 6:308 (2004)), a plug flow reactor, a continuous tubular reactor, a spinning disc reactor (e.g., from Colin Ramshaw), a spinning tube reactor, an oscillatory flow reactor, a microreactor, a hex reactor, an ultrasonic reactor (see, e.g., WO 05/118277), a multifrequency, multimode, modulated sonic & ultrasonic vibration flow-through reactor (e.g., from MP Interconsulting, Le Locle, CH), reversed flow reactor (e.g., from Matros Technologies. Inc., Chesterfield, Mo.), which are incorporated herein by reference in the entirety.

A "flow-through mixer" refers to a device in which a liquid is mixed by flowing a liquid there through. A flow-through mixer can be a static mixer, a dynamic mixer, or a combination thereof. Static mixers comprise a fixed configuration in which mixing is induced by disturbing a laminar flow of a liquid. Dynamic mixers comprise moving parts (e.g., blades, screws, screens, and the like) that actively induce mixing as a liquid is flowed there through.

A "flow-through sensor" refers to a device that measures, detects or senses one or more properties of a liquid that is flowed there through. A flow-through sensor can determine, measure or detect a property of a liquid such as, but not limited to, pH, viscosity, osmolality, clarity, salinity, water activity, temperature, pressure, refractive index, color, UV spectrum, IR spectrum, Near IR spectrum, molecular weight, ion content, starting material content, substituent precursor content, or a combination thereof. Flow-through sensors suitable for use with the present invention include, but are not limited to, a pH meter, an osmometer (e.g., from Wescor, Inc., Logan, Utah), a calorimeter (see, e.g., Sandarusi et al., Int. J. Thermophys. 9:993 (1988), a photo diode array detector (Perkin Elmer, Inc., Waltham, Mass.), an IR spectrophotometer (e.g., from Vital Sensors Technologies. Acton, Mass.), a near-IR spectrophotometer (e.g., a DCP007NIR photometer, from Kemtrak, Taiby Sweden, and described in Baptista et al., Anal. Chem. 68:971 (1996), a UV spectrophotometer (e.g., from ActiPix D100, MC Scientific, Århus V, Denmark), a colorimeter (e.g., from Optek-Danulat, Inc., Germantown, Wis.), a refractometer (VIP from MISCO, Cleveland, Ohio), a viscometer (e.g., from Cambridge Applied Systems, Medford, Mass.), and combinations thereof.

A flow-through sensor can be independently at each occurrence equipped with a flow-through detection cell. The process of the invention can employ one or more flow-through sensors, meaning one or more detectors of the same type or one or more detectors of different types.

A "sensor-responsive controller" refers to a device that directly or indirectly receives a signal from a sensor and performs an operation in response thereto that directly or indirectly controls one or more operational parameters of the process equipment. Parameters that can be controlled by a sensor-responsive controller include, but are not limited to, a feed rate, a flow rate, a temperature, a pressure, a drying rate, a filtration rate, a diafiltration rate, an ultrafiltration rate, a residence time, a pH, a composition, and combinations thereof. In some embodiments, a sensor-responsive controller can be used to control one or more parameters that control the properties of a cyclodextrin derivative prepared by a process of the present invention.

A "pump" refers to a device used to flow reactants into, through, and/or from a reactor. One or more pumps can be used with a process of the present invention. In some embodiments, each reactant is provided using a separate pump. Pumps suitable for use with the present include, but are not limited to, a diaphragm pump, a peristaltic pump, a centripetal pump, a rotary pump, a screw pump, a syringe pump, a rotary vane pump, a gear pump, a lobed rotor pump, a piston pump, a circumferential pump, an axial pump, a bladder pump, a cantilever pump, a centrifugal pump, a double diaphragm pump, a dosing or metering pump, a drum pump, a hand pump, a jet pump, a linear pump, a manual pump, a plunger pump, a radial piston pump, a rocking piston pump, a scroll pump, a turbine pump, and combinations thereof.

A "back-pressure regulator" refers to a device that adjusts the back pressure of a fluid that flows through a reactor (i.e., to increase or decrease a back pressure of a fluid). In some embodiments, at least one back-pressure regulator is located downstream of a flow-through reactor, a diafilter, and/or an ultrafilter.

An "ultrafiltration system" refers to a filtration device comprising a low molecular weight cut-off means (e.g., a sheet or membrane), through which a fluid stream comprising a product of the present invention is flowed under pressure to provide a filtrate containing a major portion of a cyclodextrin derivative.

A "diafiltration system" refers to a filtration device comprising a low molecular weight cut-off means (e.g., a sheet or membrane), through which a fluid stream comprising a product of the present invention is flowed under pressure to provide a retentate containing a major portion of a cyclodextrin derivative.

A membrane used for ultrafiltration can be the same as or different than the membrane used for diafiltration. Suitable membrane materials for use in ultrafiltration and/or diafiltration systems include, but are not limited to, polyvinylidene fluoride, polysulfone, cellulose acetate, and combinations thereof. Exemplary ultrafiltration and diafiltration devices and membranes include those sold by MILLIPORE (Billerica, Mass.), PALL Corp. (East Hills, N.Y.), KOCH Membrane Systems (Wilmington, Mass.), and NORIT Membrane Technology B.V. (Entshede, The Netherlands). In some embodiments, a filtration device operates as both an ultrafiltration system and a diafiltration system.

The filtration systems can comprise the same or different size exclusion membranes. In some embodiments, a membrane for use with a filtration system of the present invention has a nominal molecular weight cut-off of 500 Daltons ("Da") to 5,000 Da, 500 Da to 4,000 Da, 500 Da to 3,000 Da, 500 Da to 2,500 Da, 500 Da to 2,000 Da, 750 Da to 2,500 Da, 1,000 Da to 2,500 Da, 1,000 Da, 1,500 Da, 2,000 Da, 2,500 Da, or 3,000 Da.

In some embodiments, the nominal (or average) pore size of a suitable membrane is 1 nm to 200 µm, 1 nm to 100 µm, 1 nm to 50 µm, 0.01 µm to 20 µm, 0.01 µm to 10 µm, 0.01 µm to 1 µm, 0.01 µm to 0.5 µm, 0.01 µm to 0.25 µm, 0.22 µm, or 0.45 µm. When two or more filtration systems are utilized, the back-pressure of the two or more filtration systems can be the same or different and can be controlled by one or two back-pressure regulators. For example, a back-pressure regulator can be disposed between the two or more filtration systems and downstream of the last filtration system.

The pressure and pore size of the membrane of the diafiltration system is selected to retain a substantial portion of the cyclodextrin derivative in the retentate and promote transfer of low molecular weight impurities from the product to the filtrate. On the other hand, the pressure and pore size of the membrane of the ultrafiltration system is selected to promote transfer of cyclodextrin derivative from the product to the filtrate and to retain a substantial portion of the particulate or undissolved materials in the retentate, thereby clarifying the product milieu.

A "liquid-liquid extraction system" refers generally to a flow-through system having a high-permeability membrane, sheet or barrier that defines a boundary between a fluid stream comprising a product of the present invention and an extraction fluid. Components diffuse from the fluid stream comprising a product to the extraction fluid. An extraction fluid can be any aqueous or non-aqueous liquid. In some embodiments, an extraction fluid is immiscible, partially miscible, or miscible with a fluid stream comprising a product. In some embodiments, a fluid stream comprising a product is aqueous and an extraction fluid comprises a water immiscible or partially water miscible organic liquid.

Figure 5:
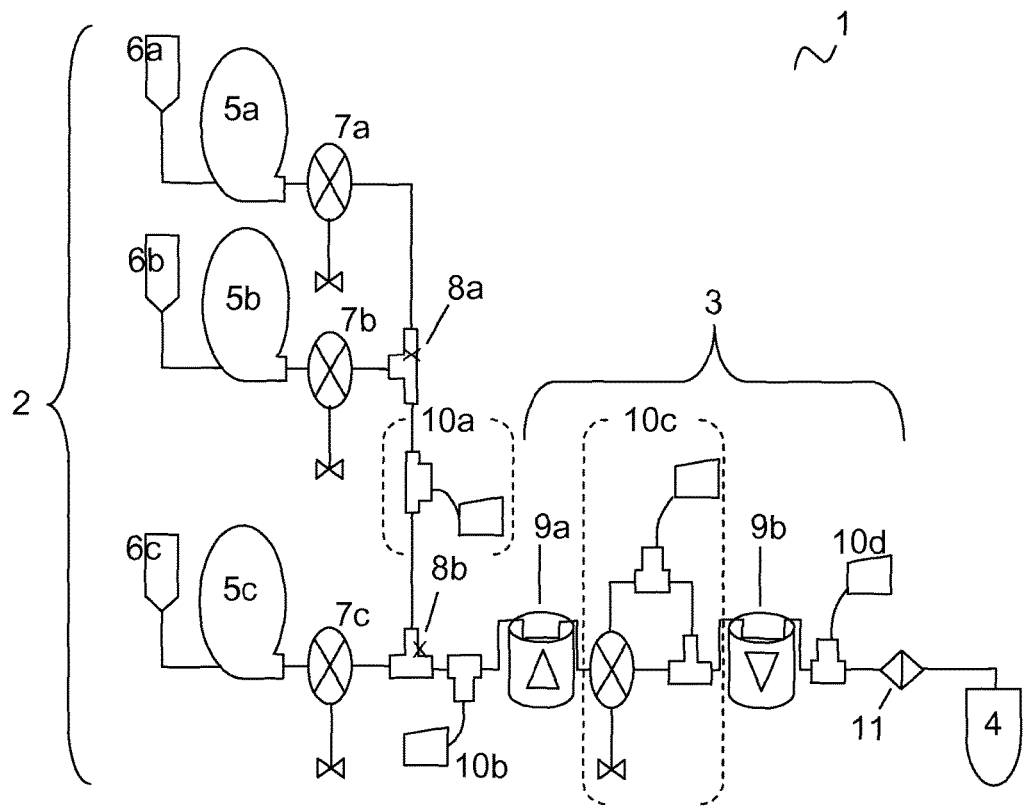
FIG. 5 provides an equipment flow diagram suitable for use with a process of the present invention comprising three starting material supplies, and serial heating and cooling devices.

FIG. 5 provides a diagram of an equipment assembly (1) comprising a starting material system (2) and a post-reaction processing system (3). The starting material system comprises three starting material supplies (6a, 6b, 6c) having corresponding pumps (5a, 5b, 5c, respectively) and valves (7a, 7b, 7c, respectively). Portions of two starting materials (from 6a and 6b) are conducted through to a flow-through mixer (8a) to form a mixture that is conducted through to another flow-through mixer (8b) in which the mixture is mixed with portions of a third starting material (from 6c) to form a flowing feedstock milieu. The is conducted through a flow-through sensor (10b) having a sensor-responsive controller (10b) operably connected thereto. The sensor is adapted to determine a property of the milieu, and the sensor-responsive controller is adapted to control (change or maintain) some aspect of the starting material system (2) as needed. For example, the sensor-responsive controller can change the feed rate for one or more of the starting materials. The flowing feedstock is conducted through a flow-through heating device (9a), which can be considered equivalent to an embodiment of a flow-through reactor or heat exchanger, and an optional flow-through cooling device (9b), which can be considered equivalent to an embodiment of a heat exchanger. Following optional cooling, the raw product is conducted to a collection vessel. The equipment assembly also comprises a pressure regulator to assist in maintaining the reaction flowing through the flow-through reactor within a target (or predetermined) range.

The equipment assembly can comprise additional sensor and sensor-responsive controller systems (10a, 10c, 10d). Each of those systems can be used to independently sense, detect, monitor, and/or determine one or more properties of the liquid conducted through itself and thereby to control or maintain process equipment performance upstream or downstream from itself. For example, one or more systems can be used to determine pH of a liquid and control feeding of an alkalinizing agent, acidifying agent, or buffering agent to the feed. One or more systems can be used to control the feed rate of one or more starting materials. One or more systems can be used to control the pressure to which the liquid is exposed during the reaction, sterilization, separation, isolation, and/or purification steps.

Figure 6:
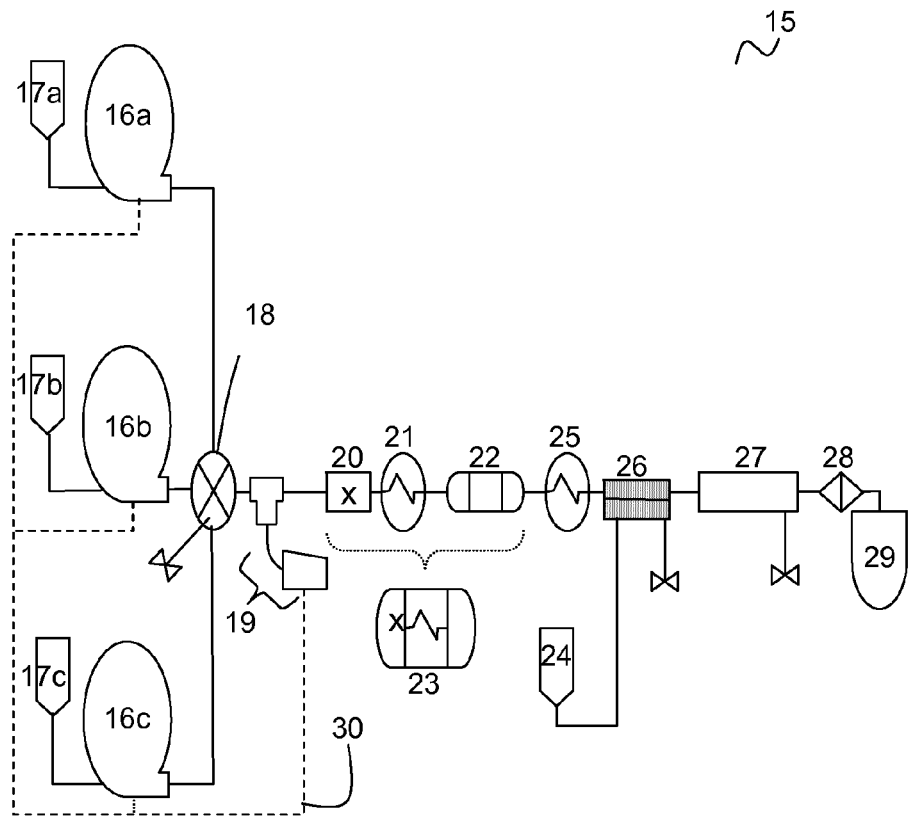
FIG. 6 provides an equipment flow diagram suitable for use with a process of the present invention comprising three starting material supplies, and serial heat exchangers separated by a flow-through reactor, a liquid-liquid extraction system, and a combination diafiltration/ultrafiltration system.
Figure 6:
Figure 6:
Figure 6:
Figure 6:
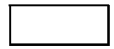
Figure 6:
Figure 6:
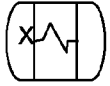

FIG. 6 provides a diagram of an equipment assembly (15) of the present invention comprising three starting material supplies (17a, 17b, 17c) with corresponding pumps (16a, 16b, 16c, respectively) and a single multi-port valve. The sensor-responsive controller (19) determines one or more properties of the flowing feedstock passing there through, and is operably connected with (30) and controls the pumps (16a, 16b, 16c), so that the flowing feedstock possesses the desired or target property. The feedstock passes through the flow-through mixer (20), flow-through heat exchanger (21), and flow-through reactor (22), which three components can instead be part of a combination mixer, heat exchanger, and flow-through reactor (23). A raw product exits the reactor and is conducted through an optional heat exchanger (25), which can heat or cool the prior to being passed through a liquid/liquid extractor (26). A partially purified (partially processed) product from the extractor is conducted to a combination diafiltration/ultrafiltration system (27), which can comprise a liquid medium feed supply (24). The pressure regulator (28) controls the back-pressure of the system (27) or of the entire assembly (15). Following purification, a purified product stream conducted to and collection in a collection vessel (29). Although not depicted, the system can comprise additional pumps or other process equipment.

Figure 7:
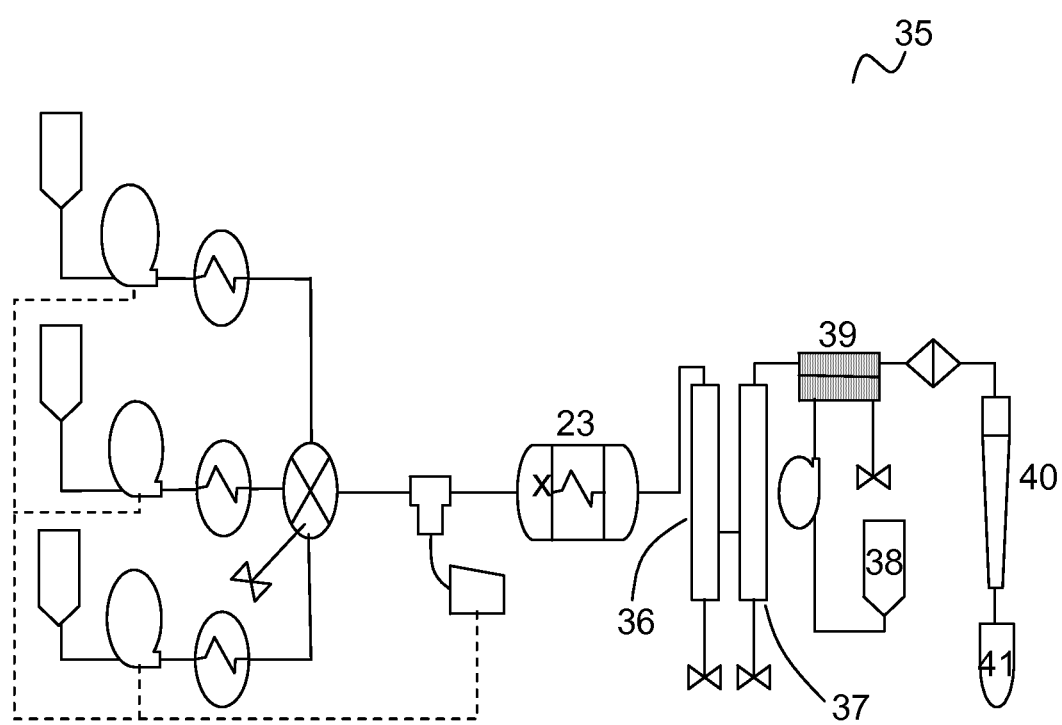
FIG. 7 provides an equipment flow diagram suitable for use with a process of the present invention comprising three starting material supplies, each having a heat exchanger, a combination mixer-heat exchanger-flow-through reactor system, a column purification/separation system, an ultrafiltration system, a liquid-liquid extraction system, and a spray dryer.

FIG. 7 provides a schematic equipment assembly (35) of the present invention comprising three starting material supplies each with its own heat exchanger, a combination mixer-heat exchanger-flow-through reactor system (23) and additional post-reaction equipment comprising a purification/separation column system (36), an ultrafiltration system (37), a liquid-liquid extraction system (39), and a spray dryer (40). The column is used to separate one or more impurities from the cyclodextrin derivative product in the product milieu, such as for removal of color-forming agents, unreacted substituent precursor, degraded or hydrolyzed substituent precursor, one or more reaction by-products, salt. UV active agents, or combinations thereof. The column system can comprise one or more columns. The ultrafiltration system (37) is used to remove unreacted cyclodextrin starting material, salt, color-forming agents, unreacted substituent precursor, degraded or hydrolyzed substituent precursor, one or more reaction by-products, UV active agents, or combinations thereof. The liquid/liquid extraction system (39) comprises an extraction fluid feed (38), and a phase separation membrane which maintains the product and extraction fluid on opposites sides but which permits interfacial contact thereof such that unwanted components in the product are extracted into the extraction fluid. The cyclodextrin derivative is isolated by removing the liquid from the purified product with a spray dryer (40) having a solids-collection vessel (41) for collecting the solid cyclodextrin derivative.

Figure 8:
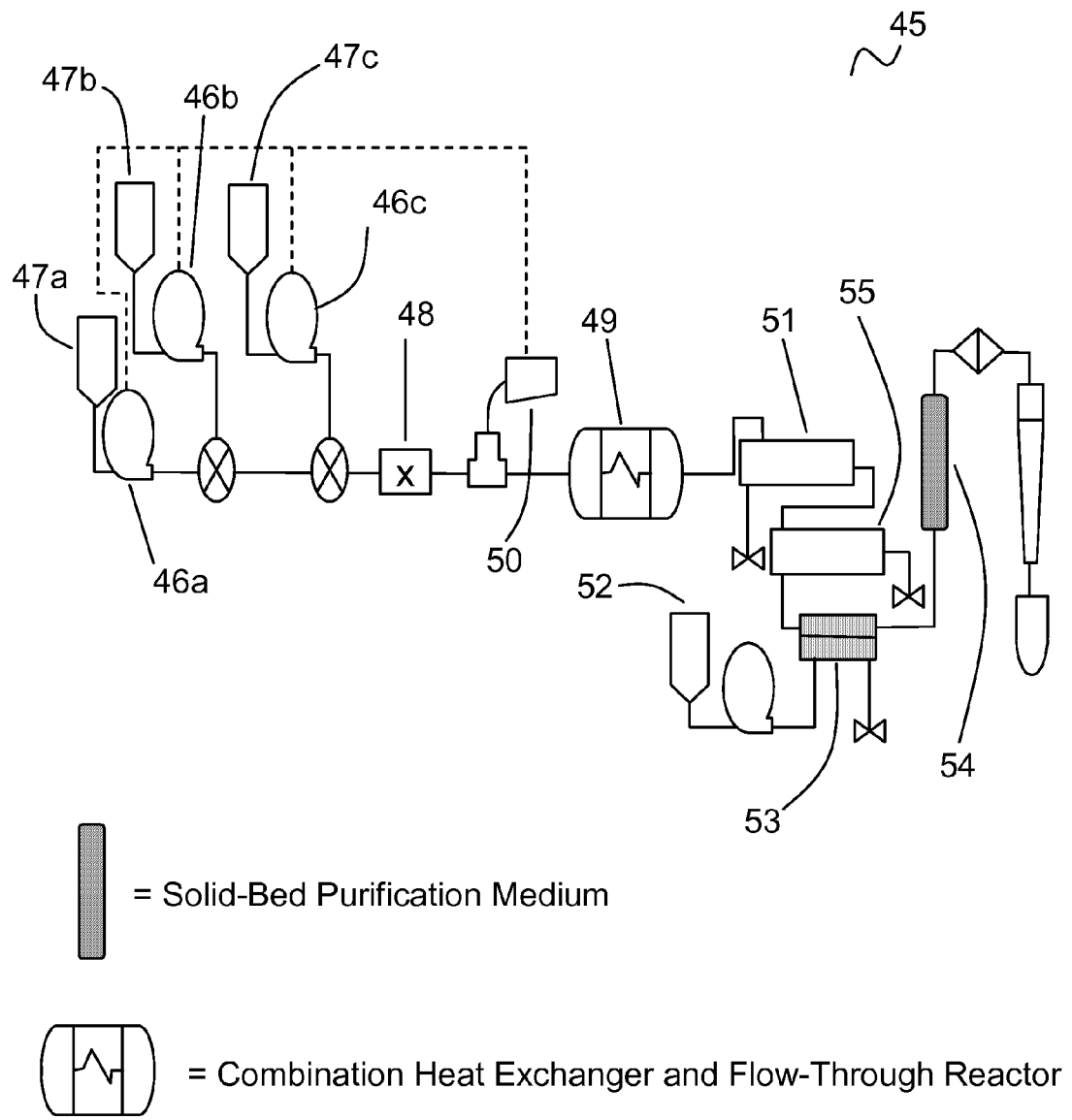
FIG. 8 provides an equipment flow diagram suitable for use with a process of the present invention comprising three starting material supplies, a mixer, a combination heat exchanger-flow-through reactor system, a diafiltration system, an ultrafiltration system, a liquid-liquid extraction system, a solid-bed purification system, and a spray dryer.

FIG. 8 provides a schematic equipment assembly of the present invention comprising three starting material supplies (47a, 47b, 47c), corresponding pumps (46a, 46b, 46c, respectively), a mixer (48), combination heat exchanger-flow-through reactor system (49), a diafiltration system (51), an ultrafiltration system (55), a liquid-liquid extraction system (53), a solid-bed purification system (54), and a spray dryer. The mixer (48) mixes the feedstock prior to entry into the reactor (49). The sensor-responsive controller (50) is operably connected to the pumps of the starting material supplies. The diafiltration system (51) is used to remove unreacted cyclodextrin starting material, impurities, reaction by-products and other unwanted low molecular weight components in the product stream. The ultrafiltration system (55) is used to clarify the partially purified product milieu. The solid-bed purification system (54) is used to remove impurities (such as pyrogens, color-forming agents, amino acids, proteins and other unwanted components) that can be adsorbed onto a solid bed of adsorption medium. In some embodiments, the solid bed comprises a powdered, particulate or resin-bound medium. For example, the solid bed can be activated carbon.

Figure 9A:
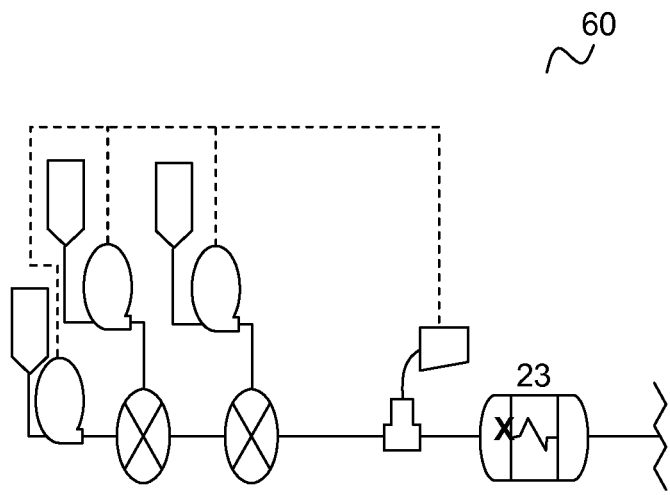
FIG. 9A provides an equipment flow diagram suitable for use with a process of the present invention comprising a starting material system in combination with a mixer-heat exchanger-flow-through reactor.

FIG. 9A provides a schematic of an equipment assembly (60) alternative to the equipment assembly provided in FIG. 8. Referring to FIG. 9A, a mixer (48) and a combination heat exchanger-flow-through reactor (49) are combined to provide a mixer-heat exchanger-flow-through reactor system.

Figure 9B:
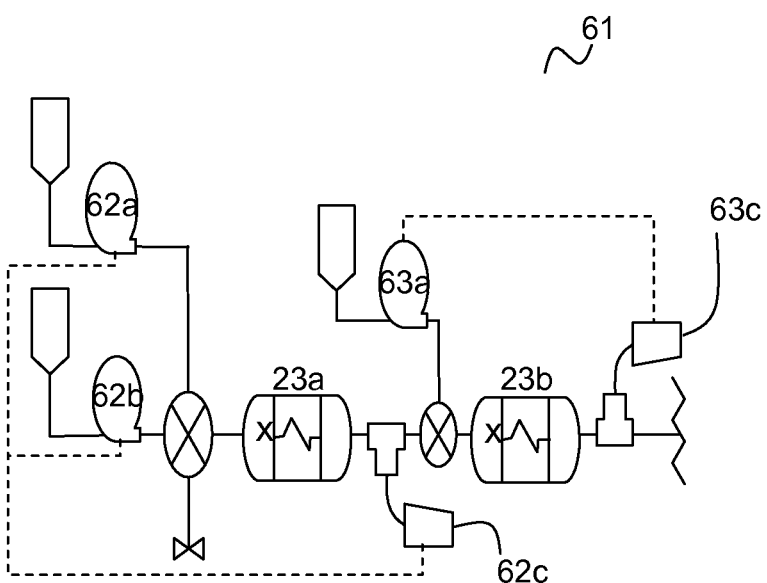
FIG. 9B provides an equipment flow diagram suitable for use with a process of the present invention comprising two starting material systems in combination with two mixer-heat exchanger-flow-through reactor systems.

FIG. 9B provides another alternative embodiment of an equipment assembly (61).

Referring to FIG. 9B, two starting material systems (62*a*, 62*b*) are combined in a mixer and passed through a first combination mixer-heat exchanger-flow-through reactor system (23*a*) to provide a first product comprising cyclodextrin derivative and unreacted cyclodextrin starting material. The starting material supply (62*a*) can comprise a mixture of cyclodextrin derivative and catalyst and the starting material supply (62*b*) can comprise a substituent precursor. Alternatively, the starting material supply (62*a*) can comprise a mixture of cyclodextrin derivative and substituent precursor and the starting material supply (62*b*) can comprise a catalyst. The first product can be treated with additional substituent precursor and/or additional catalyst (63*a*) and conducted through a second combination mixer-heat exchanger-flow-through reactor system (23*b*) which can be controlled by the sensor-responsive controller/sensor combination (63*c*). This particular assembly is suitable for increasing the degree of substitution of a first-formed cyclodextrin derivative and/or increasing the overall yield of cyclodextrin derivative in the product stream prior to purification and/or isolation.

Figure 10:
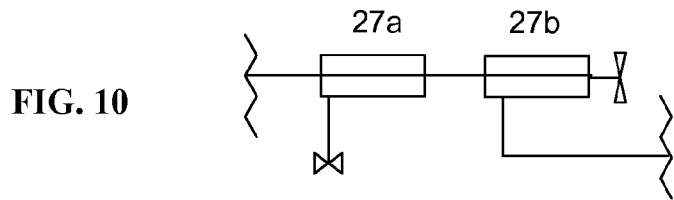
FIG. 10 provides an equipment flow diagram suitable for use with a process of the present invention comprising a post-reaction purification system that includes a diafiltration system and an ultrafiltration system.

FIG. 10 provides a schematic of a purification system comprising a diafiltration system (27*a*) and an ultrafiltration system (27*b*), such as the paired systems depicted in FIG. 8.

Figure 11A:
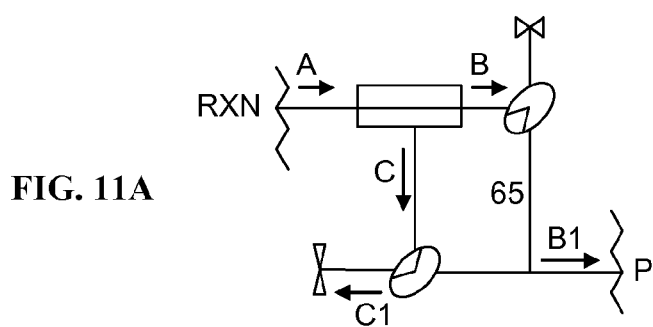
FIGS. 11A-11B provide equipment flow diagrams suitable for use with a process of the present invention comprising two different modes of operating a filtration system.
Figure 11B:
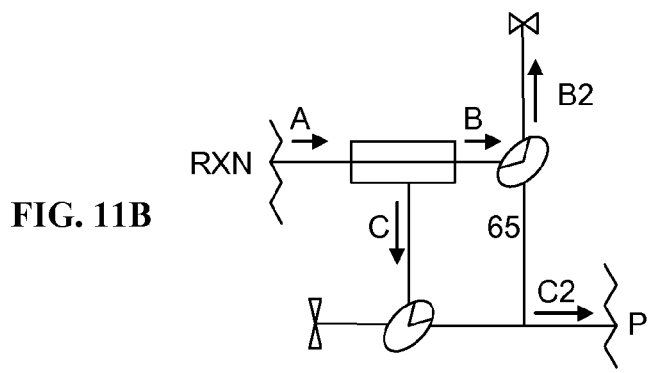

FIG. 11A-11B depict two different modes of operating a combination diafiltration/ultrafiltration system. In this embodiment, the system comprises one or more filtration apparatuses that are operated as diafilters or ultrafilters. Referring to FIG. 11A, the filtration apparatus (65) serves as a diafiltration system such that the product is conducted in the direction of Arrow A through the filtration apparatus and maintained in the retentate, which exits the apparatus in the direction of Arrow B. The partially purified product is directed and conducted in the direction of Arrow B1 for further processing. At the same time, part of the components of the liquid medium in the product pass through the filtration membrane and exit the apparatus as the filtrate in the direction of Arrow C.

By controlling disposition of the valves in the filtration system (65), it can also be operated as an ultrafiltration system. Referring to FIG. 11B, a product is conducted (Arrow A) into the filtration system and a major portion of the milieus passes through the filtration membrane to exit the system as the filtrate (Arrow) which is conducted downstream (Arrow C2) for further processing. The portion of product that does not pass through the membrane exits the filtration system as a retentate (Arrow B).

Figure 15:
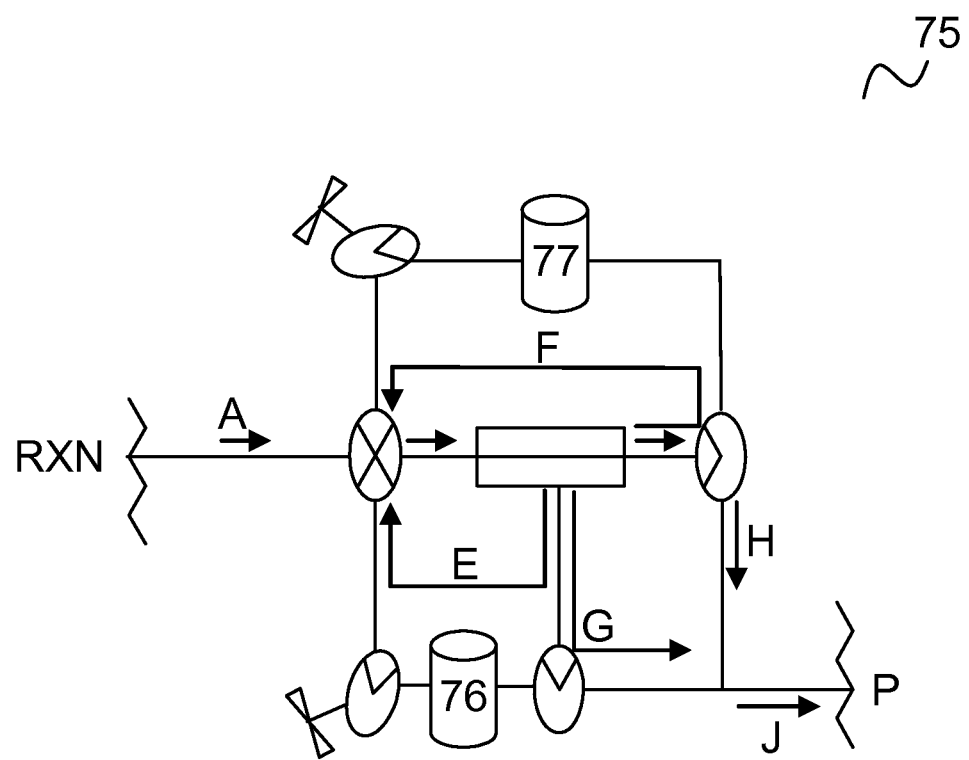
FIG. 15 provides an equipment flow diagram suitable for use with a process of the present invention comprising a combination diafiltration-ultrafiltration assembly capable of being operated in a single-pass or recycled manner.

Ultrafiltration and diafiltration operations can be conducted according to known methods or methods disclosed herein. The ultrafiltration and diafiltration systems are independently operated in a once-through (single-pass) or recycle mode. In a once-through mode, portions of the product are passed through the filtration apparatus once and conducted downstream for further processing. In a recycle mode (FIG. 15), portions of the product are passed through the filtration apparatus repeatedly. The filtration system (75) can be operated in the recycling mode as a diafilter by conducting the product (Arrow A) through the filtration apparatus such that the retentate is recycled (Arrow F) back to the product for reentry into filtration apparatus (Arrow A). The recycle vessel (77) can be included within the filtration system as a holding tank for temporarily retaining the retentate being recycled through the filtration apparatus. Once the retentate (partially purified product milieu) achieves a target endpoint for a physical property (such as content of a component in the milieu), it is conducted to the downstream processing system (P) according to Arrows H and J.

The filtration system (75) can also be operated in the recycling filtrate as an ultrafilter by product (Arrow A) through the filtration membrane of the filtration apparatus such that the filtrate is recycled (Arrow E) back to the product for reentry into filtration apparatus (Arrow A). The recycle vessel (76) can be included within the filtration system as a holding tank for temporarily retaining the filtrate being recycled through the filtration apparatus. Once the filtrate (partially purified product milieu) achieves a target endpoint for a physical property (such as concentration of cyclodextrin derivative in the milieu), it is conducted to the downstream processing system (P) according to Arrows G and J.

The filtration system can be conductively connected to the flow-through reactor system or it can be separate therefrom. The filtration system can be operated in a continuous, semi-continuous, or batch mode independent of the mode of operation of the flow-through reactor system. In some embodiments, the flow-through reactor system is operated in a continuous or semi-continuous mode, and the filtration system is operated in a continuous or semi-continuous mode and in a once-through or recycle mode. In some embodiments, the flow-through reactor system is operated in a continuous or semi-continuous mode, and the filtration system is operated in a batch mode and in a once-through or recycle mode.

The filtration system can comprise two or more filtration apparatuses in parallel and/or serial arrangement. The two or more filtration apparatuses can be operated simultaneously, sequentially, or in an overlapping manner. They can also be operated individually and independently as either a diafiltration system or an ultrafiltration system. In some embodiments, the equipment assembly comprises: 1) one or more diafiltration systems; 2) one or more ultrafiltration systems; 3) one or more filtration systems that are each independently operable as a diafiltration system and an ultrafiltration system; or 4) a combination thereof.

The order of diafiltration and ultrafiltration can be varied as needed within the process. In some embodiments, diafiltration is conducted prior to ultrafiltration, and in other embodiments, ultrafiltration is conducted prior to the diafiltration.

Figure 12:
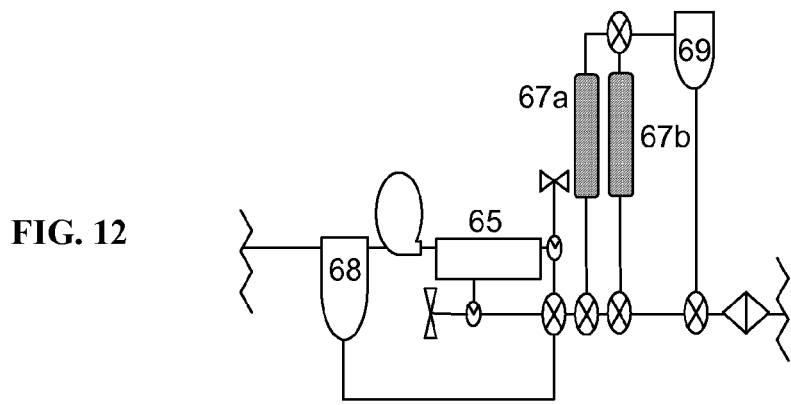
FIG. 12 provides an equipment flow diagram suitable for use with a process of the present invention comprising recycling a reaction mixture through a filtration system and a tandem solid-bed purification system.

FIG. 12 provides a flow diagram of a post-reaction processing system comprising a recycling filtration system (65) and a recycling parallel solid-bed purification system (67a, 67b). The recycling filtration system comprises a holding tank (68) for temporarily retaining the recycled partially purified product and optionally for mixing it with the raw product conducted from the reactor. The solid-bed purification system comprises two or more solid-bed purification apparatuses in parallel. The partially purified product is conducted through one or both of the purification apparatuses. The effluent is collected in a holding tank (69) and temporarily retained therein during the recycle operation. If the purification system is operated in a once-through mode, the holding tank (69) is optional.

Figure 13:
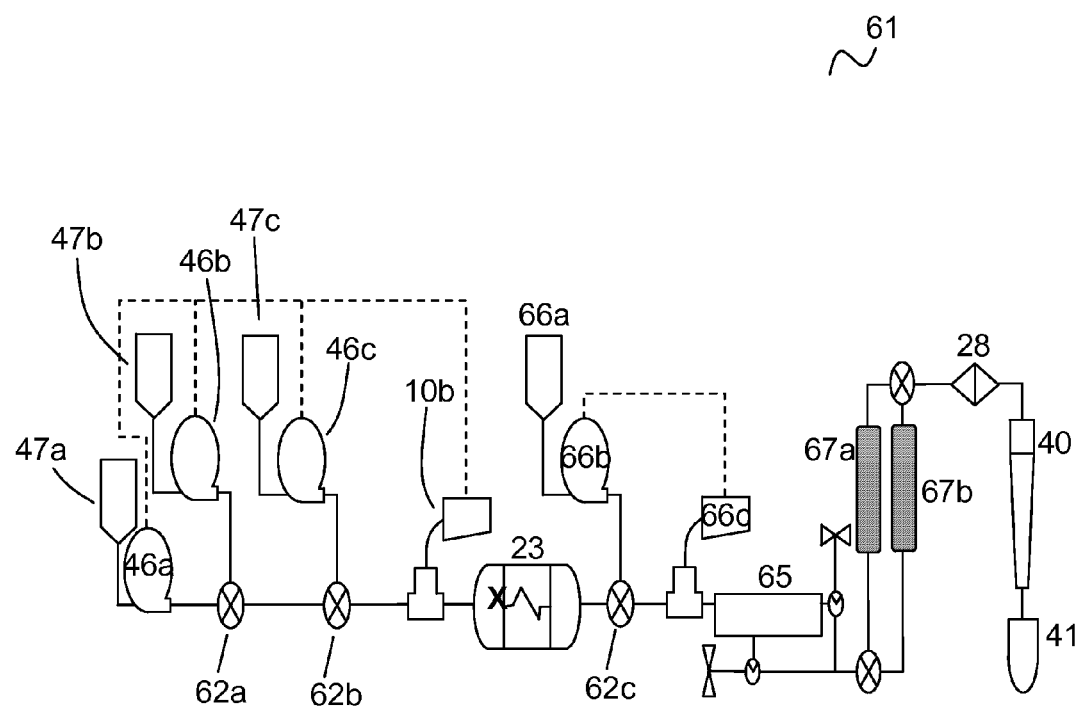
FIG. 13 provides an equipment flow diagram suitable for use with a process of the present invention comprising three starting material supplies, a combination mixer-heat exchanger-flow-through reactor system, a filtration system, a solid-bed purification system, and a spray dryer.

FIG. 13 provides a flow diagram of an equipment assembly (61) of the present invention comprising three starting material supplies (47a, 47b, 47c), three corresponding pumps (46a, 46b, 46c), valves (62a, 62b, 62c), a sensor-responsive controller/sensor combination (10b, 66c), a combination mixer-heat exchanger-flow-through reactor system (23), a filtration system operable as a diafiltration system and an ultrafiltration system (65), a solid-bed purification system (67a, 67b), spray dryer (40), and collection vessel (41). This assembly can be used to provide a mixed ether cyclodextrin derivative, increase the yield of cyclodextrin derivative in the product milieu, and/or reduce the amount of unreacted cyclodextrin starting material in the product milieu.

Figure 14:
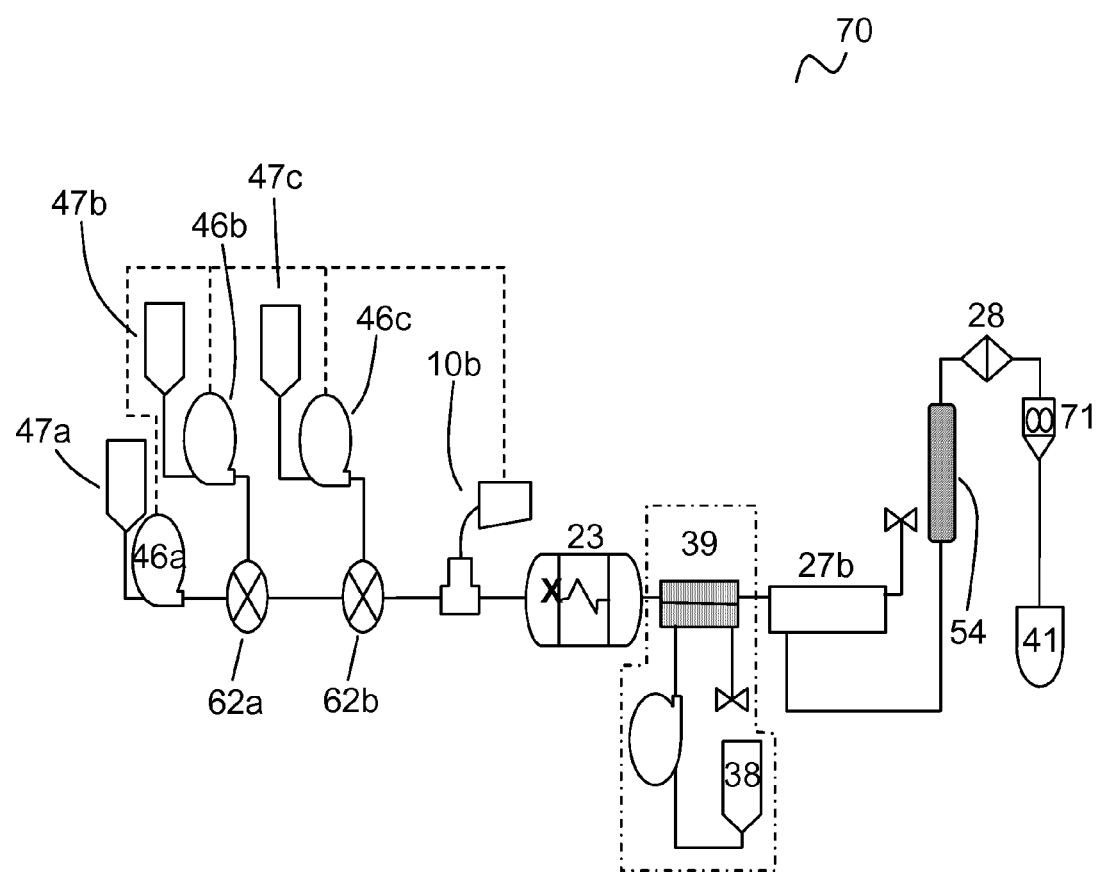
FIG. 14 provides an equipment flow diagram suitable for use with a process of the present invention comprising three starting material supplies, a combination mixer-heat exchanger-flow-through reactor system, a liquid-liquid extraction system, an ultrafiltration system, a solid-bed purification system, and a fluid concentrator.

FIG. 14 provides a flow diagram of an equipment assembly (70) of the present invention comprising plural starting material supplies (47a, 47b. 47c), plural corresponding pumps (46a, 46b, 46c, respectively), plural valves (62a, 62b), a combination mixer-heat exchanger-flow-through reactor system (23), an optional liquid-liquid extraction apparatus (39) with extraction fluid supply (38) and pump, an ultrafiltration system (27b), a solid-bed purification system (54), pressure regulator (28), fluid concentrator (71) and collection vessel (41). The ultrafiltration system can be replaced with a filtration system operable as a diafiltration system and an ultrafiltration system (65). The fluid concentrator (71) concentrates the purified product by removing liquid medium therefrom. Suitable fluid concentrators include a rotary evaporator, drum dryer, vacuum drum dryer, spray agglomerator, spray dryer, or tray dryer.

In view of the above description and the examples below, one of ordinary skill in the art will be able to practice the invention as claimed without undue experimentation. The foregoing will be better understood with reference to the following examples that detail certain procedures for the preparation of compositions and formulations according to the present invention. All references made to these examples are for the purposes of illustration. The following examples should not be considered exhaustive, but merely illustrative of only a few of the many embodiments contemplated by the present invention.

EXAMPLES

Example 1

Preparation of Cyclodextrin Derivative Having a Monomodal Distribution Profile

The equipment assembly according to the invention was used to prepare cyclodextrin derivative compositions as follows. A supply of cyclodextrin starting material was added to aqueous liquid medium to provide a concentration of cyclodextrin starting material of about 10% to about 95% by weight. A supply of alkalinizing agent was added to the cyclodextrin starting material and liquid medium in an amount sufficient to raise the pH to about 9 to about 13 or higher and at an alkalinizing agent to cyclodextrin starting material molar ratio of about 1:1 to about 16:1 or greater to form an alkaline cyclodextrin-containing aqueous milieu. A supply of substituent precursor (neat or dilute) was provided. Portions of the alkaline cyclodextrin-containing aqueous milieu were contacted in-line with portions of substituent precursor to form a flowing feedstock in a conduit, wherein the molar ratio of substituent precursor to cyclodextrin starting material was in the range of about 1:1 to about 15:1. Portions of the feedstock were optionally mixed while in the conduit. Portions of the flowing feedstock were conducted (pumped) through a flow-through reactor having an internal reactor temperature within the range of about 40° C. to about 200° C. for a residence time ranging from about 0.5 sec to about 2 hours and at a pressure of about 10 psi to about 200 psi to form a raw product comprising a derivatized cyclodextrin in an aqueous liquid medium, and optionally: one or more reaction by-product(s), unreacted cyclodextrin starting material, unreacted substituent precursor, degraded or hydrolyzed substituent precursor, and/or salt. The raw product was optionally quenched by adding acidifying agent or buffering agent. The raw product was then subjected to diafiltration (portionwise or batchwise) using a filtration apparatus equipped with a size exclusion membrane (nominally about 1000 Da) to remove low molecular impurities to form a partially purified product that was then subjected to ultrafiltration (portionwise or batchwise) using a filtration apparatus equipped with a size exclusion membrane to remove particulates (clarification) and optionally concentrate the partially purified product milieu. The ultrafiltered partially purified product was further purified (portionwise or batchwise) by treatment with an adsorbent to form the purified product that was then optionally sterilized. The purified product was then stored as is (as an aqueous solution comprising cyclodextrin derivative) or subjected to a liquid removal (or reduction) step to reduce the amount of liquid medium in or remove the liquid medium from the product and then stored.

The cyclodextrin derivative possessed a monomodal distribution profile and an average degree of substitution ranging from about 1 to about 10. The yield of cyclodextrin derivative in the raw product was in the range of about 75% to about 100%, and the overall yield of cyclodextrin derivative after completion of the process was in the range of about 60% to about 99%.

Example 2

Preparation of Cyclodextrin Derivative Having a Bimodal Distribution Profile

The equipment assembly of the present invention was used to prepare a cyclodextrin derivative compositions as follows. A supply of a cyclodextrin and a supply of substituent precursor were mixed in an aqueous liquid medium to provide a starting material mixture. A supply of alkalinizing agent in an aqueous liquid medium was also provided. Portions of the alkalinizing agent-containing medium were contacted and mixed in-line with portions of starting material mixture in an amount sufficient to raise the pH to 9 or higher and at an alkalinizing agent to cyclodextrin molar ratio of about 8:1 or greater to form flowing feedstock in a conduit. Portions of the feedstock were optionally mixed while in the conduit. Portions of the flowing feedstock were conducted (pumped) through a flow-through reactor as detailed in Example 1 to form a raw product comprising cyclodextrin derivative, aqueous liquid medium, and optionally: one or more reaction by-product(s), unreacted cyclodextrin starting material, unreacted substituent precursor, degraded or hydrolyzed substituent precursor, and/or salt. The raw product was subsequently processed as detailed in Example 1.

The cyclodextrin derivative of this process possessed a bimodal distribution profile and an average degree of substitution ranging from about 1 to about 10. The yield of cyclodextrin derivative in the initial raw product was in the range of about 65% to about 99%, and the overall yield of cyclodextrin derivative after completion of the process was in the range of about 60% to about 98%.

Example 3

Preparation of SBE-β-CD Derivatives

SBE-β-CD derivatives were prepared as follows according to Example 1. The starting materials included: an unsubstituted β-cyclodextrin starting material, butane sultone (substituent precursor), sodium hydroxide (catalyst and alkalinizing agent), and water (liquid medium). Butane sultone was used neat in liquid form. An alkaline solution containing cyclodextrin starting material (30% w/w) was prepared by mixing β-cyclodextrin (e.g., 100 g. water corrected), NaOH (e.g., 33 g) and water (e.g., 222 g). The molecular weight of butane sultone is 136.17 g/mole and its density is 1.331 g/mL; therefore the concentration of neat butane sultone was 9.77 M.

The in-line FRX™ 400 system equipment assembly (Syrris, Charlestown, Mass.) used comprised: two or three starting material supply pumps (one for the butane sultone and one for the alkaline β-cyclodextrin solution); a flow-through reactor cell having an internal volume of 1 mL; a back-pressure regulator; plastic or metal tubing as the conduit; and a collection vessel for collecting the product milieu. The pH of the feedstock solution prior to passage through the flow-through reactor was about 13. The reaction parameters and stoichiometry are provided in Table 7. The residence time for all reactions was 1 minute, and the ratio of NaOH:β-CD (ratio of catalyst/alkalinizing agent to cyclodextrin starting material was 9.5:1). Parameters that were varied included the flow rate of sulfoalkylating agent (butane sultone, "BS"), the flow rate of the β-cyclodextrin reagent stream, the ratio of the sulfoalkylating agent to the cyclodextrin starting material, and the reaction temperature.

TABLE 7

| Exp # | butane sultone (mL/min) | β-CD (mL/min) | butane sultone: β-CD | Temp (° C.) | SAE-CD Yield (%) | ADS |
|---|---|---|---|---|---|---|
| 3-A | 0.03 | 0.97 | 1:1 | 159 | 100% | 1.9 |
| 3-B | 0.05 | 0.95 | 2:1 | 159 | 99.6% | 2.2 |
| 3-C | 0.08 | 0.92 | 3:1 | 159 | 99.7% | 2.6 |
| 3-D | 0.1 | 0.9 | 4:1 | 159 | 99.4% | 2.9 |
| 3-E | 0.12 | 0.88 | 5:1 | 159 | 99.8% | 3.3 |
| 3-F | 0.14 | 0.86 | 6:1 | 159 | 99.5% | 4.1 |
| 3-G | 0.16 | 0.84 | 7:1 | 159 | 99.7% | 4.6 |
| 3-H | 0.18 | 0.82 | 8:1 | 159 | 99.9% | 4.2 |
| 3-I | 0.1 | 0.9 | 4:1 | 165 | 99.8% | 3.2 |
| 3-J | 0.1 | 0.9 | 4:1 | 170 | 99.9% | 3.1 |

TABLE 7-continued

| Exp # | butane sultone (mL/min) | β-CD (mL/min) | butane sultone: β-CD | Temp (° C.) | SAE-CD Yield (%) | ADS |
|---|---|---|---|---|---|---|
| 3-K | 0.12 | 0.88 | 5:1 | 170 | 99.9% | 3.4 |
| 3-L | 0.14 | 0.86 | 6:1 | 170 | 100% | 3.7 |
| 3-M | 0.16 | 0.84 | 7:1 | 170 | 100% | 4.0 |
| 3-N | 0.18 | 0.82 | 8:1 | 170 | 100% | 4.7 |
| 3-O | 0.18 | 0.82 | 8:1 | 170 | 99.6% | 5.0 |
| 3-P | 0.21 | 0.79 | 10:1 | 170 | 99.6% | 5.0 |
| 3-Q | 0.23 | 0.77 | 11:1 | 170 | 99.8% | 5.1 |
| 3-R | 0.25 | 0.75 | 12:1 | 170 | 100% | 5.4 |
| rxn 12 | 0.18 | 0.82 | 8:1 | 160 | 99.9% | 4.4 |
| rxn 13 | 0.21 | 0.79 | 10:1 | 140 | 100% | 5.3 |
| rxn 14 | 0.25 | 0.75 | 12:1 | 140 | 99.8% | 5.4 |
| rxn 15 | 0.18 | 0.82 | 8:1 | 160 | 100% | 5.3 |
| rxn 16 | 0.21 | 0.79 | 10:1 | 160 | 99.9% | 5.0 |
| rxn 17 | 0.25 | 0.75 | 12:1 | 160 | 99.5% | 4.6 |

Example 4

Preparation of SBE-β-CD Derivatives

The procedure of Example 3 was followed except that an alkaline cyclodextrin starting material-containing solution containing 10% w/w of β-cyclodextrin was used. The alkaline solution was prepared by mixing β-cyclodextrin, NaOH, and water. Cyclodextrin derivatives prepared according to this procedure and the process parameters therefore are detailed below.

The reaction parameters and stoichiometry are provided in Table 8. The residence time for all reactions was 1 minute, and the ratio of NaOH:β-cyclodextrin (ratio of catalyst/alkalinizing agent to cyclodextrin starting material was 11:1). Parameters that were varied included the flow rate of sulfoalkylating agent (butane sultone, "BS"), the flow rate of the β-cyclodextrin reagent stream, the ratio of the sulfoalkylating agent to the cyclodextrin starting material, and the reaction temperature.

TABLE 8

| Exp # | butane sultone (mL/min) | β-CD (mL/min) | BS:β-CD | Temp (° C.) | SAE-CD Yield (%) | Avg. Degree of Substitution |
|---|---|---|---|---|---|---|
| RX1 | 0.07 | 0.93 | 8:1 | 140 | 100 | 3.8 |
| RX7 | 0.07 | 0.93 | 8:1 | 160 | 99.7 | 3.7 |
| RX5 | 0.08 | 0.92 | 10:1 | 140 | 100 | 4.2 |
| RX9 | 0.08 | 0.92 | 10:1 | 160 | 100 | 4.1 |
| RX15 | 0.10 | 0.90 | 12:1 | 140 | 99.1 | 4.1 |
| RX11 | 0.10 | 0.90 | 12:1 | 160 | 99.9 | 4.4 |

Example 5

Preparation of SBE-β-CD Derivatives

The procedure of Example 3 was followed except that 16 mL flow-through reactor (Syrris™ tube reactor, 16 mL) was used. Cyclodextrin derivatives prepared according to this procedure and the process parameters therefore are detailed below. The combined flow rate for the butane sultone and β-CD/NaOH solution was 0.5 mL/min, 1.0 mL/min, or 2.0 mL/min, which resulted in a residence time of 32 minutes, 16 minutes, or 8 minutes, respectively. The molar ratio of NaOH to β-cyclodextrin starting material was 9.5:1. The other reaction parameters and stoichiometry are provided in Table 9.

TABLE 9

| Lot# | butane sultone (mL/min) | β-CD (mL/min) | BS:β-CD | Temp (° C.) | Res. Time (mL/min) | SAE-CD Yield (%) | ADS |
|---|---|---|---|---|---|---|---|
| RX26b | 0.36 | 1.64 | 8:1 | 120 | 8 | 99.7 | 4.3 |
| RX30b | 0.43 | 1.57 | 10:1 | 120 | 8 | 99.6 | 4.3 |
| RX2b | 0.18 | 0.82 | 8:1 | 120 | 16 | 100 | 4.5 |
| RX6b | 0.21 | 0.79 | 10:1 | 120 | 16 | 99.2 | 4.4 |
| RX10b | 0.25 | 0.75 | 12:1 | 120 | 16 | 99.2 | 5.1 |
| RX13b | 0.09 | 0.41 | 8:1 | 100 | 32 | 99.8 | 5.1 |
| RX13c* | 0.09 | 0.41 | 8:1 | 100 | 32 | 99.8 | 5.2 |
| RX17b | 0.11 | 0.39 | 10:1 | 100 | 32 | 100 | 5.4 |
| RX21b | 0.12 | 0.38 | 12:1 | 100 | 32 | 100 | |
| RX14b | 0.09 | 0.41 | 8:1 | 120 | 32 | 99.5 | 4.8 |
| RX18b | 0.11 | 0.39 | 10:1 | 120 | 32 | 99.7 | 4.5 |
| RX22b | 0.12 | 0.38 | 12:1 | 120 | 32 | 99.8 | 5.4 |

*Denotes a reaction conducted with an in-line mixer, specifically the static multichannel cross-flow chip (1 mL internal volume; Syrris ™).

Example 6

Preparation of SBE-β-CD Derivatives

The procedure of Example 3 was followed except that the combined flow rate for the butane sultone (BS) and β-CD/NaOH solution was varied between 0.5 mL/min, 1.0 mL/min and 2.0 mL/min, and a 16 mL flow-through reactor. Mixing was achieved using a static 2-way mixing union. The molar ratio of NaOH to β-cyclodextrin starting material was 9.5:1 for all reactions. All reactions were performed at 100° C. The other reaction parameters and stoichiometry are provided in Table 10.

TABLE 10

| Lot# | butane sultone (mL/min) | β-CD (mL/min) | BS:β-CD | SAE-CD Yield (%) | Residence Time (min.) | ADS |
|---|---|---|---|---|---|---|
| RX25e | 0.36 | 1.64 | 8:1 | 99.8 | 8 | 4.7 |
| RX29e | 0.43 | 1.57 | 10:1 | 100 | 8 | 5.2 |
| RX33e | 0.49 | 1.51 | 12:1 | 100 | 8 | 5.5 |
| RX1c | 0.18 | 0.82 | 8:1 | 99.8 | 16 | 5 |
| RX5c | 0.21 | 0.79 | 10:1 | 100 | 16 | 5 |
| RX9c | 0.25 | 0.75 | 12:1 | 99.8 | 16 | 5.7 |
| RX13d | 0.09 | 0.41 | 8:1 | 99.5 | 32 | 5.5 |
| RX17d | 0.11 | 0.39 | 10:1 | 99.8 | 32 | 5.6 |
| RX21d | 0.12 | 0.38 | 12:1 | To be determined | 32 | To be determined |

Example 7

Preparation of SBE-β-CD Derivatives

The procedure of Example 3 was followed except that the combined flow rate for the butane sultone (BS) and β-CD/NaOH solution was varied as indicated below. The temperature for all reactions was 140° C., and the molar ratio of NaOH to β-cyclodextrin starting material was 9.5:1 for all reactions. The other reaction parameters and stoichiometry are provided in Table 11.

TABLE 11

| Lot# | butane sultone (mL/min) | β-CD (mL/min) | BS:β-CD | BS + β-CD flow rate (mL/min) | Residence Time (min.) | SAE-CD Yield (%) | ADS |
|---|---|---|---|---|---|---|---|
| RX27f | 0.36 | 1.64 | 8:1 | 2 | 0.5 | 98.6 | 4.5 |
| RX31f | 0.43 | 1.57 | 10:1 | 2 | 0.5 | 98.9 | 5.2 |
| RX35f | 0.49 | 1.51 | 12:1 | 2 | 0.5 | 90 | 5.6 |
| RX3f | 0.18 | 0.82 | 8:1 | 1 | 1 | 99.6 | 4.7 |
| RX7f | 0.21 | 0.79 | 10:1 | 1 | 1 | 99.7 | 5 |
| RX11f | 0.25 | 0.75 | 12:1 | 1 | 1 | 99.5 | 5.3 |
| RX15f | 0.09 | 0.41 | 8:1 | 0.5 | 2 | 99.9 | 4.7 |
| RX19f | 0.11 | 0.39 | 10:1 | 0.5 | 2 | 100 | 5.1 |
| RX23f | 0.12 | 0.38 | 12:1 | 0.5 | 2 | 100 | 5.1 |

Example 8

Preparation of SBE-γ-CD Derivatives

The procedure of Example 3 was followed except that γ-cyclodextrin was used as the cyclodextrin starting material. The combined flow rate for the butane sultone and γ-CD/NaOH solution was 1 mL/min, which provided a residence time of 1 minute. The reaction temperature was 120° C., and the molar ratio of NaOH to γ-cyclodextrin starting material was 9.5:1 for all reactions. The other reaction parameters and stoichiometry are provided in Table 12.

TABLE 12

| Lot | RX43 | RX44 | RX45 |
|---|---|---|---|
| Butane sultone (flow rate, mL/min) | 0.08 | 0.14 | 0.20 |
| γ-CD (flow rate, mL/min) | 0.92 | 0.86 | 0.80 |
| Molar ratio of butane sultone:γ-CD | 3:1 | 6:1 | 10:1 |
| Avg. Degree of Substitution | 1.7 | 2.6 | 3.8 |

Example 9

Preparation of Mixed SBE-γ-CD and SBE-r-CD Derivatives

The procedure of Example 3 was followed except that γ-cyclodextrin and β-cyclodextrin were both used as the cyclodextrin starting material. The concentration of cyclodextrin starting material in the supply solution was 30% (w/w) β-cyclodextrin and 30% (w/w) γ-cyclodextrin. The combined flow rate for the butane sultone and cyclodextrin/NaOH solution was 1 mL/min, which provided a residence time of 1 minute.

The solutions of β-cyclodextrin and γ-cyclodextrin were provided separately.

A 30% w/w solution of γ-cyclodextrin (γ-CD) was prepared by dissolving in 147 eq of water and 9.5 eq of NaOH, and a 30% w/w solution of β-cyclodextrin (β-CD) was prepared by dissolving in 125 eq of water and 9.5 eq of NaOH. Thus, the molar ratio of NaOH to γ-cyclodextrin starting material was 9.5:1 for all reactions. The other reaction parameters and stoichiometry are provided Table 13.

TABLE 13

| Lot | RX46 | RX47 | RX48 | RX49 |
|---|---|---|---|---|
| Butane sultone (flow rate, mL/min) | 0.11 | 0.13 | 0.11 | 0.13 |
| β-CD (flow rate, mL/min) | 0.42 | 0.41 | 0.42 | 0.41 |
| γ-CD (flow rate, mL/min) | 0.47 | 0.46 | 0.47 | 0.46 |
| Molar ratio of butane sultone | | | | |
| Reaction Temp. (° C.) | 120 | 120 | 140 | 140 |
| Avg. Degree of Substitution | 3.2 | 4.1 | 4.2 | 4.6 |

Example 10

Preparation of SBE-β-CD Derivatives

The process of Example 3 was modified to include two in-line reactors. The butane sultone reaction mixture was divided into two batches that were split between the first and second reactors. Thus, a first portion of butane sultone was combined with the β-CD/NaOH solution and passed through a first 1 mL in-line reactor to form a first reaction product. A second portion of butane sultone was then combined with the first reaction product in a second 1 mL in-line reactor to form a final derivatized SBE-β-CD reaction product. The residence time in each reactor was 1 minute, for a total residence time of 2 minutes. The molar ratio of NaOH to β-cyclodextrin starting material was 9.5:1 for all reactions, and the reaction temperature in each reactor was 140° C. The other reaction parameters and stoichiometry are provided in Table 14.

TABLE 14

| Parameters | Experiment | | | |
|---|---|---|---|---|
| | RX36 | RX37 | RX38 | RX39 |
| β-CD (flow rate, mL/min) | 0.86 | 0.86 | 0.86 | 0.86 |
| 1st butane sultone flow rate (mL/min) | 0.14 | 0.14 | 0.14 | 0.14 |
| BS:β-CD 1 | 6:1 | 6:1 | 6:1 | 6:1 |
| 2nd butane sultone flow rate (mL/min) | 0.05 | 0.1 | 0.14 | — |
| BS:β-CD 2 | 2:1 | 4:1 | 6:1 | — |
| BS:β-CD Total | 8:1 | 10:1 | 12:1 | 6:1 |
| Avg. Degree of Substitution | 4.3 | 5.2 | 5.2 | 3.9 |
| SAE-CD Yield (%) | 99.8% | 100% | 99.9% | 99.3% |

The above process conditions were modified by adding a second portion of NaOH to the process solution in the second reactor. The residence time in each reactor was 1 minute, for a total residence time of 2 minutes. The starting molar ratio of NaOH to β-cyclodextrin starting material was 9.5:1 for all reactions, and the reaction temperature in each reactor was 140° C. The other reaction parameters and stoichiometry are provided in Table 15.

TABLE 15

| Parameters | RX14B1 | RX14B2 | RX14B3 |
|---|---|---|---|
| β-CD (flow rate, mL/min) | 0.86 | 0.86 | 0.86 |
| 1st butane sultone flow rate (mL/min) | 0.14 | 0.14 | 0.14 |
| BS:β-CD 1 | 6:1 | 6:1 | 6:1 |
| 2nd butane sultone flow rate (mL/min) | 0.05 | 0.1 | 0.14 |
| BS:β-CD 2 | 2:1 | 4:1 | 6:1 |
| BS:β-CD Total | 8:1 | 10:1 | 12:1 |
| NaOH:β-CD ratio in reactor 1 | 9.5:1 | 9.5:1 | 9.5:1 |
| NaOH equivalent added in 2nd reactor | 1 | 3 | 5 |
| NaOH:β-CD ratio in reactor 2 | 10.5:1 | 12.5:1 | 14.5:1 |
| Avg. Degree of Substitution | To be determined | To be determined | To be determined |
| SAE-β-CD Yield (%) | To be determined | To be determined | To be determined |

Example 11

Preparation of SBE-EE-β-CD Derivatives

The process of Example 3 was followed except that two substituent precursors were employed: butane sultone (BS) and diethyl sulfate (DES). The cyclodextrin derivative formed was sulfobutyl ether-ethyl ether cyclodextrin having an average degree of substitution of about 4 for the sulfobutyl substituent and an average degree of substitution of about 2 for ethyl substituent. The substituent precursors were formulated as two separate reaction streams that were added separately and sequentially to portions of the NaOH/β-CD solution to form a flowing feedstock that was conducted into and through a 1 mL in-line reactor. The residence time was 0.88 minutes (about 52 seconds). The starting molar ratio of NaOH to β-cyclodextrin starting material was 9.5:1 for all reactions, and the reaction temperature in each reactor was 140° C. The other reaction parameters and stoichiometry are provided in Table 16.

TABLE 16

|  | EX83 |
| --- | --- |
| Butane Sultone flow rate (mL/min) | 0.14 |
| Diethyl Sulfate flow rate (mL/min) | 0.14 |
| β-CD (mL/min) | 0.86 |
| BS:β-CD | 6:1 |
| DES:β-CD | 6:1 |
| Avg. Degree of Ethyl Substitution | 2 |
| Avg. Degree of Sulfobutyl Substitution | 4 |
| Yield of derivatized cyclodextrin (%) | To be determined |

Example 12

Preparation of SBE-β-CD Derivatives

Sulfobutyl ether-β-cyclodextrin derivatives that vary in the average degree of substitution were prepared according to Example 1. The starting materials included: β-cyclodextrin as the cyclodextrin starting material, butane sultone (BS) as the substituent precursor, sodium hydroxide as the catalyst (alkalinizing agent), and water as the liquid medium. Butane sultone was used neat in liquid form. The butane sultone (36 g), β-cyclodextrin (30 g; 30% w/w) and water (34 mL) were mixed using a high shear mixer (e.g., a rotor stator or ultrasonic probe) to form a first liquid feedstock. A 50% w/w sodium hydroxide aqueous solution (11.6 g of NaOH) was the second liquid feedstock.

The first and second liquid feedstocks were combined and reacted in an in-line FRX™ 400 system (Syrris, Charlestown, Mass.). Two starting material supply pumps (one for the BS/β-CD feedstock and one for the alkaline feedstock) were utilized to flow the feedstocks into a flow-through reactor cell (microreactor) having an internal volume of 1 mL. The system also included a back-pressure regulator, plastic tubing as the conduit, and a collection vessel for collecting the reaction product. The pH of the feedstock solution prior to passage through the flow-through reactor was about 9 to 13. Portions of the first liquid feedstock are continuously combined with portions of the second liquid feedstock and conducted through the in-line reactor under the following conditions to form the specified cyclodextrin derivatives. The concentration of β-cyclodextrin in the starting material ranged from 60% to 80% w/w.

Example 13

Preparation of SBE-β-CD Employing a Flow-Through Microwave Reactor

Continuous flow reactions were performed using the FlowSynth (Milestone Microwave Laboratory Systems, Shelton, Conn.) equipment assembly equipped with a microwave heated vertical flow-through reactor. The reagents were pumped in from the bottom of the reactor through the microwave chamber to the top of the reactor and into a water-cooled heat exchanger. β-cyclodextrin (1 eq) was mixed with water, NaOH (11 eq), and butane sultone (4.5 eq) to form a suspension which was pumped through the microwave chamber at a flow rate of 25 mL/min. The microwave reactor was set to heat the reaction to at 165'C. The reaction had a residence time of 8 min. Fractions of the raw product were collected from the outlet every 5 minutes and neutralized with 2M HCl immediately after collection. A capillary electropherogram of each fraction was obtained. The average degree of substitution of the SBE-β-CD and the yield of SBE-β-CD in the raw product was determined and is summarized in Table 17.

TABLE 17

| Fraction | Collection Period after start of rxn (min) | Yield (%) | Avg. Degree of Substitution |
| --- | --- | --- | --- |
| 1 | 1-5 | 85.4 | 1.8 |
| 2 | 6-10 | 91.4 | 2.1 |
| 3 | 11-15 | 93.1 | 2 |
| 4 | 16-20 | 95.2 | 3.2 |

Example 14

Preparation of SBE-β-CD Using a Concentrated Feedstock Milieu

The process of Example 3 is followed except that the following parameters are altered: a) the concentration of β-cyclodextrin starting material ranged from 60% to 80% w/w; b) the molar ratio of NaOH to β-cyclodextrin can be increased greater than 9.5:1; c) the molar ratio of butane sultone to β-cyclodextrin can be greater than 12:1; d) the molar ratio of NaOH to butane sultone can be greater than 1:1; and e) the NaOH/β-cyclodextrin reactant mixture can be pre-heated prior to mixing with the butane sultone.

Example 15

Batch Process Followed by In-Line Single Pass Continuous Ultrafiltration

A sulfobutyl ether β-cyclodextrin was prepared using a batch process by dissolving β-cyclodextrin in the solution of 176 eq of water and 13.6 eq NaOH and charging 1,4-butane sultone (8.5 eq) over 15 minutes with heating to 70° C. The reaction was allowed to proceed overnight at the same temperature. The solution was subsequently cooled to room temperature and neutralized to pH 6.8 with dilute aqueous hydrochloric acid. The neutralized solution was filtered through a 0.45 μm filter and analyzed for purity and impurities by Capillary Electrophoresis.

The reaction product solution of SBE-β-CD was passed through a FLEX (SYRRIS®) systems) ultrafiltration flow-through apparatus equipped with a 500 Da molecular weight cut-off circular membrane (surface area=0.8-1.8 cm$^2$) at a pressure of 70 psig. The flow rate through the membrane was maintained between 1 mL/min and 0.5 mL/min. The reaction product solution was diluted with water to provide an aqueous solution comprising between 10%, 25%, 50%, or 100% of the reaction product. The flow rate of the permeate water counter flow was varied between 1 mL/min and 0.5 mL/min. The concentration of hydrolyzed butane sultone remaining in the crude solution was determined after each single pass through the filtration unit. The data are summarized in Table 18.

TABLE 18

| Ref # | Rxn Product Conc.[a] | Flow Rate (ml/min) | [Hydrolyzed Sultone] Area* | [Hydrolyzed Sultone] Area %* | mOsm |
|---|---|---|---|---|---|
| Initial | — | — | 306475 | 48.48 | — |
| 10A | 100% | 1 | 347483 | 47.91 | >2500 |
| 10B | 100% | 0.5 | 547385 | 53.66 | 2501 |
| 10C | 50% | 1 | 176737 | 43.57 | 1236 |
| 10D | 50% | 0.5 | 172658 | 43.3 | 1183 |
| 10E | 25% | 1 | 69101 | 44.3 | 639 |
| 10F | 25% | 0.5 | 85316 | 42.3 | 628 |
| 10G | 10% | 1 | 10921 | 12.9 | 235 |
| 10H | 10% | 0.5 | 29207 | 40.13 | 217 |

[a]100% indicates no dilution of the reaction product prior to or during in-line ultrafiltration, whereas 10% indicates a 9:1 dilution of the reaction product prior to or during in-line ultrafiltration.
*All 2 drops of concentrate sample.

The solution was purified by Ultrafiltration using a 1000 Da molecular weight cut-off membrane. The Ultrafiltration end point was determined by capillary electrophoresis wherein the filtrate showed no or substantially no presence of 4-hydroxybutane-1-sulfonic acid and/or disodium bis(4-sulfobutyl)ether, and by Osmolarity, wherein the permeate samples had little to no ion present. The solution was further treated with activated carbon (0.12 gram of carbon per gram of cyclodextrin), filtered using a 0.22 m filter and neutralized to provide a solution having a pH of about 6.5 to about 7. The resulting solution was concentrated to roughly a 50% solution by Rotary evaporation at about 50° C. to about 60° C. under less than 30 mmHg vacuum. The solution was freeze dried to yield a $SBE_{6.8}$-β-CD as a white solid.

Example 16

In-Line Ultrafiltration with Recycling of the Retentate

A batch of crude sulfobutyl ether β-cyclodextrin was synthesized by preparing a 30% stock solution of β-cyclodextrin in 125 eq of water and 9.5 eq NaOH. This solution and 1,4-butane sultone were pumped into a 1 mL glass microreactor that was pre-heated to 140° C. The β-cyclodextrin solution was pumped at a flow rate of 0.82 mL/min and the 1,4-butane sultone at a flow rate of 0.18 mL/min (10 eq). The output from the microreactor was neutralized with 4 N HCl to a pH of about 6.5. The crude reaction mixture was analyzed for purity and impurities by Capillary Electrophoresis and contained 53.8% as hydrolyzed sultone, 3.2% as β-cyclodextrin content and 1,4-butane sultone levels of 9,680 ppm.

The crude solution SBE-β-CD was passed through a TFF Omega 650 MWCO Capsule at a pressure of 35 to 50 psi and a differential pressure on the permeate side of 0.15 mBar multiple times to determine the change in impurities each time. The concentration of unreacted β-cyclodextrin, butane sultone and hydrolyzed butane sultone remaining in the retentate was measured after each pass through the filtration apparatus. Table 19 below shows the results of the repeated single pass ultrafiltrations.

TABLE 19

| Exp Number | Sample Conc. | β-CD (%) | 1,4-butane sultone (ppm) | hydrolyzed sultone (%) |
|---|---|---|---|---|
| Initial | 30% | 3.20 | 9680 | 53.8 |
| 1st pass | 30% | 3.67 | 1544 | 56.7 |
| 2nd pass | 30% | 3.60 | 1263 | 53.4 |
| 3rd pass | 30% | 2.80 | 524 | 51.3 |

Example 17

Preparation of SAE-CD Derivatives in Organic Liquid

Sulfobutyl ether cyclodextrin derivatives are prepared by combining an underivatized cyclodextrin starting material, a sulfoalkylating agent, and a catalyst in an organic liquid.

In this example, pyridine is both a catalyst and an organic liquid medium for the reaction. Pyridine and underivatized cyclodextrin starting material are combined to form a reactant mixture supply. The molar ration of pyridine to cyclodextrin can be 1:1, to 10,000:1, 1:1 to 1,000:1, 1:1 to 100:1, 1:1 to 10:1, or 1:1. A butane sultone supply is provided. Portions of the reactant mixture and portions of the butane sultone are combined and conducted through an in-line reactor (having an internal volume of 1 mL) at a temperature of 50° C. to 180° C. at a residence time of 0.1 min to 2 hrs. The molar ratio of butane sultone to cyclodextrin is 1:1 to 12:1. After passing through the in-line reactor, the raw product containing the sulfobutyl ether cyclodextrin derivative-containing solution is combined with water and the pH is lowered with acid to 5 to 8. The sulfobutyl ether cyclodextrin derivative is isolated according to processes described herein.

Alternatively, pyridine and dimethylaminopyridine (DMAP) can serve as the reaction catalysts. The above process can be modified by adding DMAP to the reactant mixture of pyridine and cyclodextrin prior to contacting the solution with the butane sultone. The molar ratio of DMAP:CD is 0.1:1 to 25:1, or 1:1 to 10:1.

The pyridine can be added to the butane sultone feed prior to reacting the butane sultone with the cyclodextrin mixture. The molar ratio of pyridine to butane sultone is in the range of 0.1:1 to 10:1, or 1:1 to 5:1. In some embodiments, the concentration of pyridine in the butane sultone feed is minimized to prevent solidification in the reaction lines due to the formation of salt mixture. In some embodiments, the reaction lines are heated to ensure even flow of the reaction feedstocks.

In some embodiments, when DMAP is utilized, the DMAP can be added to the butane sultone feedstock prior to reacting butane sultone with the cyclodextrin. The molar ratio of DMAP to the butane sultone can be 0.1:1 to 10:1, 0.5:1 to 2:1, 0.5:1 to 1.5:1, or 0.9:1 to 1.1:1. If the DMAP-butane sultone mixture forms a solid salt, the salt can be melted by heating the lines of the reactor and/or a polar organic liquid (e.g., pyridine) can be added to the DMAP-butane sultone mixture.

Example 18

Preparation of Mixed Ether Cyclodextrin Derivatives

The equipment assembly of FIG. 13 is employed. The following combinations of substituent precursors are employed to prepare the specified mixed ether cyclodextrin derivatives.

TABLE 20

| Reaction No. | First substituent precursor | Second substituent precursor | Mixed ether CD derivative |
| --- | --- | --- | --- |
| ME-1 | Butane sultone | Propylene oxide | SBE-HPE-CD |
| ME-2 | Butane sultone | Ethylene oxide | SBE-HEE-CD |
| ME-3 | Propane sultone | 3,4-epoxy-1-butene | SPE-HBNE-CD |
| ME-4 | Butane sultone | 3,4-epoxy-1-butene | SBE-HBNE-CD |
| ME-5 | Butane sultone | Diethyl sulfate | SBE-EE-CD |
| ME-6 | Propylene oxide | Diethyl sulfate | HP-EE-CD |
| ME-7 | Propylene oxide | 3,4-epoxy-1-butene | HPE-HBNE-CD |
| ME-8 | Diethyl sulfate | Dimethyl sulfate | EE-ME-CD |

Any cyclodextrin starting material can be used. Any suitable catalyst can be used. The molar ratio of catalyst to cyclodextrin starting material is generally in the range of 0.05:1 to 30:1 or as otherwise defined herein. In some embodiments, the molar ratio of catalyst to cyclodextrin starting material approximates or exceeds the molar ratio of total substituent precursor (sum of both substituent precursors) to cyclodextrin starting material.

The ADS for each substituent of the mixed ether can be determined by capillary electrophoresis or NMR as described herein or other known methods. Mixed ether cyclodextrin derivatives differing in the ADS of each substituent can be prepared by varying the molar ratio of first substituent precursor to second substituent precursor, the molar ratio of the first substituent precursor to cyclodextrin starting material, and/or the molar ratio of second substituent precursor to cyclodextrin starting material. The molar ratio of first substituent precursor to second substituent precursor generally ranges from 0.05:1 to 1:0.05 or 0.1:1 to 1:0.1. Generally, the molar ratio of each substituent precursor to cyclodextrin starting material independently ranges from 0.05:1 to 100:1, 0.05:1 to 75:1, 0.05:1 to 50:1 or 0.05:1 to 30:1: however, the sum total of the molar ratios of first substituent precursor to cyclodextrin starting material and second substituent precursor to cyclodextrin starting material will generally range from 1:1 to 100:1, e.g., 0.1:1 (molar ratio of first substituent precursor to cyclodextrin starting material)+0.9:1 (molar ratio of second substituent precursor to cyclodextrin starting material)=1:1, at a minimum.

Generally, the higher the concentration of substituent precursor in the feedstock milieu, the higher its corresponding ADS in the cyclodextrin derivative.

Example 19

Preparation of a Metal Salt of a Cyclodextrin Starting Material

The metal salt of an underivatized cyclodextrin starting material can be prepared by dissolving the underivatized cyclodextrin in water and adding an alkalinizing agent thereto to form an aqueous solution of the metal salt of the cyclodextrin starting material. The aqueous liquid is added to a water miscible organic solvent (such as an alcohol, an ether such as tetrahydrofuran, or another suitable solvent) to affect precipitation of the salt, which can be separated from the supernatant by filtration, centrifugation, settling and decanting or other known means. The molar ratio of alkalinizing agent to the cyclodextrin starting material generally ranges as specified herein.

To 3 moles of β-cyclodextrin in 12 L of demineralized water is added 66 moles of NaOH or KOH pellets. The sodium (or potassium) salt Na-β-CD is isolated by slowly adding the resulting solution to 20 L of stirred anhydrous ethanol at room temperature which results in the precipitation of the product. The slurry can be stirred overnight, optionally with cooling, to crystallize the product. The product is optionally isolated by filtration and the filter cake washed with ethanol (optionally anhydrous). The Na-β-CD is optionally dried.

A metal salt of a cyclodextrin can be prepared in organic solvent liquid medium instead of in aqueous liquid medium by following Method 1 above except that the underivatized cyclodextrin is placed in an organic solvent liquid medium rather than an aqueous liquid medium. In this case, the metal salt of the cyclodextrin will precipitate directly out of the organic solvent liquid medium.

Example 20

Preparation of a Cyclodextrin Derivative from Alkali Metal Salt of Cyclodextrin Starting Material The alkali metal salt of a cyclodextrin starting material prepared according to Example 19 is reacted with one or more substituent precursors, optionally in the presence of a liquid carrier and optionally in the presence of a catalyst, to form the cyclodextrin derivative, which is further treated as described herein. A liquid phase or gaseous phase comprising substituent precursor is employed. The liquid phase can be neat substituent precursor, a combination of substituent precursor and liquid carrier. A liquid carrier can be an organic or non-organic solvent liquid carrier and it can be aqueous or non-aqueous. The gaseous phase generally comprises a low-boiling or gaseous substituent precursor. Any of the equipment assemblies described herein can be employed in this process.

The molar ratio of total substituent precursor to cyclodextrin starting material can be varied as described herein.

Example 21

Preparation of SPE-CD Derivative from Na-γ-Cyclodextrin Starting Material

Method 1

Na-γ-CD starting material prepared according to Example 20 is placed in organic solvent to form a cyclodextrin supply. Portions of 1,3-propane sultone and cyclodextrin supply are mixed in line to form a flowing feedstock milieu, which is passed portionwise through an in-line reactor to form a raw product comprising SPE-γ-CD sodium salt. The product can be further processed as described herein.

Method 2.

Na-γ-CD (50 mmoles) is placed in an organic solvent (e.g., ethanol, tetrahydrofuran, butanol, dimethylsulfoxide, dimethylformamide, N-methylpyrrolidone, poly(ethylene glycol), propylene glycol, other water miscible or immiscible organic solvent, or a mixture thereof) to form a cyclodextrin supply. The organic solvent can optionally contain water (generally 20% or less, 15% or less, 10%/0 or less, 7.5% or less, 5% or less, 2.5% or less, or 1% or less water, by weight). 1,3-Propane sultone (500 mmoles) is provided. Portions of the cyclodextrin supply and propane sultone are mixed in-line to form a flowing feedstock and passed portionwise through an in-line reactor to form raw product comprising SPE-γ-CD sodium salt. The product can be isolated in crude form by addition of a water immiscible organic solvent (e.g., diethyl ether, hexane), optionally containing an acidifying agent. Alternatively, the product can be isolated by placing it in an aqueous solution and adjusting the pH to less than 8 by addition of an acidifying agent or buffer. Unreacted propane sultone and other by-products can be removed as described herein.

Example 22

Preparation of SBE-β-CD Derivative from Na-β-Cyclodextrin Starting Material Method 1.

Na-β-CD starting material prepared according to Example 28 is placed in organic solvent to form a cyclodextrin supply. Portions of 1,4-butane sultone and cyclodextrin supply are mixed in line to form a flowing feedstock milieu, which is passed portionwise through an in-line reactor to form a raw product comprising SBE-β-CD sodium salt. The product can be further processed as described herein.

Method 2.

Na-β-CD (100 mmoles) containing a sodium to cyclodextrin molar ratio of 6:1 to 10:1 (or 6.5:1 to 10:1, 6:1 to 7:1, 6:1 to 9.5:1, 6:1 to 9:1, 6:1 to 8.5:1, 6.5:1 to 8:1, 7:1 to 10:1, 7:1 to 9:1, 7:1 to 8.5:1, 7:1 to 8:1) is placed in sufficient organic solvent (e.g., ethanol, tetrahydrofuran, butanol, dimethylsulfoxide, dimethylformamide, N-methylpyrrolidone, poly(ethylene glycol), propylene glycol, other water miscible or immiscible organic solvent, or a mixture thereof) to form a cyclodextrin supply containing a Na-β-CD concentration of 10% to 95%/wt. (or 10% to 90% wt., 15% to 85% wt., 20% to 85% wt., 25% to 85%, 30% to 85% wt., 40% to 85% wt., 50% to 85% wt., or 60% to 85% wt.). The organic solvent optionally contains water (generally 20% or less, 15% or less, 10% or less, 7.5% or less, 5% or less, 2.5% or less, or 1% or less by weight). Then, 1,4-butane sultone (600 to 1200 mmoles, 600 to 1100 mmoles, 650 to 1100 mmoles, 650 to 1000 mmoles, 650 to 950 mmoles, 650 to 900 mmoles, 650 to 850 mmoles, 650 to 800 mmoles, 650 to 750 mmoles, or 700 to 800 mmoles) is provided. Portions of the cyclodextrin supply and butane sultone are mixed in-line to form a flowing feedstock (having a butane sultone to Na-β-CD molar ratio of 6:1 to 12:1, 6:1 to 11:1, 6.5:1 to 10:1, 6.5:1 to 9.5:1, 6.5:1 to 9:1, 6.5:1 to 8.5:1, 6.5:1 to 8:1, 6.5:1 to 7:1, or 7:1 to 8:1) and passed portionwise continuously or semicontinuously through an in-line reactor to form raw product comprising SBE-β-CD sodium salt having a degree of substitution in the range of 6 to 11 (or 6 to 7, 6 to 10.5, 6 to 10, 6 to 9.5, 6 to 9, 6 to 8.5, 6 to 8, 6.5 to 8, 6.5 to 7.5, 6.5 to 7, or 6 to 7). The product can be isolated in crude form by addition of a water immiscible organic solvent (e.g., diethyl ether, hexane), optionally containing an acidifying agent. Alternatively, the product can be isolated by placing it in an aqueous solution and adjusting the pH to less than 8 by addition of an acidifying agent or buffer. Unreacted 1,4-butane sultone and other by-products can be removed as described herein.

Example 23

Preparation of SBE$_{6.1}$-β-CD Derivative

A sulfobutyl ether β-cyclodextrin (SBE-β-CD) having an average degree of substitution of 6.1 was synthesized by the following procedure. An aqueous solution comprising underivatized β-cyclodextrin (β-CD) was prepared by dissolving β-CD (100 g) in water (140 eq), along with NaOH (9.4 eq) to provide a 30% w/w 3-CD solution. A second solution was prepared by rapidly mixing 1,4-butate sultone (neat) with an equal amount of water to provide a 50% w/w homogenous mixture. The S-CD solution and the 1,4-butane sultone solution were flowed into a tube reactor (having an internal volume of 16 mL) adjusted to a temperature of 100° C.-110° C. by immersion in an oil bath. The flow rate of the β-CD solution was 0.64 mL/min and the flow rate of 1,4-butane sultone solution was 0.36 mL/min (to provide a total flow of 1 mL/min and a residence time of 16 minutes). The flow rates of the two solutions into the reactor provided a reaction stoichiometry of 8 eq of 1,4-butane sultone and 1 eq. of β-CD. The raw product comprising SBE-β-CD was collected as it exited the tube reactor, and the ADS was analyzed by Capillary Electrophoresis (CE). The CE data indicated an ADS for the SBE-β-CD product of about 6.1.

This, and other examples demonstrate it is possible to synthesize derivatized cyclodextrins by rapidly reacting a cyclodextrin starting material with a substituent precursor under conditions in which a minimum amount of solvent is utilized, and the substituent precursor either reacts rapidly with the cyclodextrin derivative or is rapidly decomposed. Furthermore, these examples show that a cyclodextrin derivative can be purified by continuous ultrafiltration and spray dry processes.

Example 24

Preparation of SBE$_6$-β-CD Derivative by a Batch Reaction Process

A SBE-β-CD was synthesized by using a batch process under the following conditions. An aqueous solution comprising underivatized 3-CD was prepared by dissolving 3-CD (100 g, adjusted for a water content of 13.3%) in water (157 eq) that contained NaOH (11 eq). The resulting solution was heated to 70° C., and a single charge of 1,4-butane sultone (8 eq) was delivered to the heated β-CD solution. The resulting reaction solution was sampled 5, 10, 30, 60, 120, and 360 minutes after addition of the 1,4-butane sultone. The samples were analyzed Gas Chromatography (GC), the results of which are provided in Table 21.

TABLE 21

| Time (mm) | 1,4-butane sultone (ppm) |
| --- | --- |
| 5 | 32,000 |
| 10 | 52,200 |
| 30 | 7,000 |
| 60 | 3,530 |
| 120 | 72 |
| 360 | 7 |

Samples from the reaction solution at 1, 20, 30, and 60 minutes were analyzed using CE to determine the ADS of the cyclodextrin derivative versus time. The reaction solution provided a cyclodextrin derivative having an ADS of about 2.9, about 5, about 5, and about 5.1, after a period of 1, 20, 30, and 60 minutes, respectively.

After the sampling, the reaction solution was stirred overnight and the temperature was maintained above 70° C. The following morning the reaction solution was cooled to room temperature (about 25° C.) and HCl was added until the solution had a pH of about 7. The neutralized solution was then purified by ultrafiltration and carbon treatment, and then concentrated to provide a 50% w/w. The concentrated solution was then freeze dried to provide a dry product comprising a derivatized cyclodextrin (SBE-β-CD, 127 g). The final product had an ADS of about 6, as determined by CE.

Na-β-CD starting material prepared according to Example 28 is placed in organic solvent to form a cyclodextrin supply. Portions of 1,4-butane sultone and cyclodextrin supply are mixed in line to form a flowing feedstock milieu, which is passed portionwise through an in-line reactor to form a raw product comprising SBE-β-CD sodium salt. The product can be further processed as described herein.

CONCLUSION

These examples illustrate possible embodiments of the present invention. While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A process for preparing a derivatized cyclodextrin, the process comprising: reacting a cyclodextrin starting material, a substituent precursor, and an optional catalyst to provide a raw product comprising a derivatized cyclodextrin, wherein:
   the raw product comprises 1% or less of an initial amount of the substituent precursor, and
   the reacting is performed in a continuous or semi-continuous manner comprising:
   providing a feedstock comprising a liquid or gas medium, the cyclodextrin starting material, the substituent precursor, and the optional catalyst; and
   continuously or semi-continuously flowing the feedstock into a flow-through reactor and simultaneously flowing out of the flow-through reactor the raw product comprising a derivatized cyclodextrin;
   wherein the feedstock has a residence time in the flow-through reactor of 0.5 sec to 30 minutes, and the flow-through reactor temperature is 70° C. to 200° C.

2. The process of claim 1, wherein the process does not include after the reacting, adding a reagent to the raw product in order to degrade the substituent precursor.

3. The process of claim 1, wherein the cyclodextrin starting material comprises an unsubstituted cyclodextrin selected from the group consisting of: an α-cyclodextrin, a β cyclodextrin, a γcyclodextrin, and combinations thereof.

4. The process of claim 1, wherein the substituent precursor and the cyclodextrin starting material are present in a molar ratio of 1:1 to 50:1.

5. The process of claim 1, wherein the substituent precursor is selected from the group consisting of: a sulfoalkylating agent, an alkylating agent, and combinations thereof.

6. The process of claim 5, wherein the substituent precursor is selected from the group consisting of: butane sultone, diethyl sulfate, and combinations thereof.

7. The process of claim 1, wherein the substituent precursor comprises a mixture of two or more substituent precursors.

8. The process of claim 1, wherein the optional catalyst is present in molar excess relative to the substituent precursor.

9. The process of claim 1, wherein the optional catalyst is selected from the group consisting of: an alkalinizing agent, an acidifying agent, a phase transfer agent, an enzyme, a transition metal compound, and combinations thereof.

10. The process of claim 1, wherein the optional catalyst comprises an alkalinizing agent, and the substituent precursor is selected from the group consisting of: a sulfoalkylating agent, an alkylating agent, a hydroxyalkylating agent, and combinations thereof.

11. The process of claim 1, further comprising pre-heating at least one of the cyclodextrin starting material, the substituent precursor, or a combination thereof.

12. The process of claim 1, wherein the feedstock comprises a medium selected from the group consisting of: water, an alcohol, an ether, a ketone, a sulfoxide, a nitrile, an amide, an ester, an oil, a chlorinated solvent, a water-soluble polymer, and combinations thereof.

13. The process of claim 1, wherein the providing comprises a process selected from the group consisting of:
   (i) mixing the cyclodextrin starting material with the optional catalyst to form a mixture, and mixing portions of the mixture with portions of the substituent precursor to form the feedstock;
   (ii) mixing the cyclodextrin starting material with the substituent precursor to form a mixture, and mixing portions of the mixture with portions of the optional catalyst to form the feedstock;
   (iii) mixing the optional catalyst with the substituent precursor to form a mixture, and mixing the mixture with portions of the cyclodextrin starting material to form the feedstock; and
   (iv) mixing portions of the cyclodextrin starting material, the substituent precursor, and the optional catalyst substantially simultaneously to form the feedstock.

14. The process of claim 13, wherein the mixing comprises flowing any of the mixtures through a flow-through mixer.

15. The process of claim 1, wherein the feedstock has a pH of 9 to 14, the feedstock has a residence time in the flow-through reactor of 0.5 sec to 20 minutes, and the temperature of the flow-through reactor is 90° C. to 160° C.

16. The process of claim 1, further comprising quenching any unreacted substituent precursor present in the raw product.

17. The process of claim 1, further comprising neutralizing the raw product.

18. The process of claim 1, further comprising separating the derivatized cyclodextrin from the raw product, wherein the separating includes at least one of filtering, centrifuging, decanting, or a combination thereof.

19. The process of claim 1, further comprising isolating the derivatized cyclodextrin, wherein the isolating includes at least one of drying, sterile filtering, concentrating, and combinations thereof.

20. The process of claim 1, further comprising purifying the derivatized cyclodextrin, wherein the purifying includes at least one of extracting, diafiltrating, dialyzing, treating with a carbon medium, treating with an adsorption medium, treating with a color-removal medium, and combinations thereof.

21. The process of claim 1, wherein the derivatized cyclodextrin is present in the raw product in a yield of 70% or higher based upon the amount of the cyclodextrin starting material.

22. The process of claim 1, wherein a molar ratio of the substituent precursor to the cyclodextrin starting material of 3:1 to 18:1 provides a derivatized cyclodextrin having an average degree of substitution of 2 to 12.

23. The process of claim 1, wherein a molar ratio of the substituent precursor to the cyclodextrin starting material of 1:1 to 5:1 provides a derivatized cyclodextrin having an average degree of substitution of 4 or less.

24. The process of claim 1, wherein a molar ratio of the substituent precursor to the cyclodextrin starting material of 5:1 to 14:1 provides a derivatized cyclodextrin having an average degree of substitution of 3 to 7.

25. The process of claim 1, wherein the derivatized cyclodextrin has a solubility in water of 100 mg/mL or higher.

26. The process of claim 1, wherein the derivatized cyclodextrin includes a cationic substituent, an anionic substituent, or a combination thereof.

27. The process of claim 1, wherein the derivatized cyclodextrin includes a substituent selected from the group consisting of: a sulfoalkyl ether group, an ether group, an alkyl ether group, an alkenyl ether group, a hydroxyalkyl ether group, a hydroxyalkenyl ether group, a thioalkyl ether group, an aminoalklyl ether group, a mercapto group, an amino group, an alkylamino group, a carboxyl group, an ester group, a nitro group, a halo group, an aldehyde group, a 2,3-epoxypropyl group, and combinations thereof.

28. A process for preparing a derivatized cyclodextrin, the process comprising:
  combining in a liquid or gas medium a cyclodextrin starting material, a sulfoalkylating agent present in a molar excess relative to the cyclodextrin starting material, and an alkalinizing agent present in a molar excess relative to the one or more sulfoalkylating agents to form a feedstock; and
  reacting the feedstock by continuously or semi-continuously flowing the feedstock into and out of a flow-through reactor for a residence time of 0.5 sec to 30 minutes, at a temperature of 70° C. to 200° C., and at a pressure of 1 bar or higher to form a raw product comprising the derivatized cyclodextrin and 1% or less of an initial amount of the substituent precursor.

* * * * *